(12) United States Patent
Naidu et al.

(10) Patent No.: US 7,419,969 B2
(45) Date of Patent: *Sep. 2, 2008

(54) HIV INTEGRASE INHIBITORS: CYCLIC PYRIMIDINONE COMPOUNDS

(75) Inventors: B. Narasimhulu Naidu, Durham, CT (US); Timothy P. Connolly, Portland, CT (US); Yasutsugu Ueda, Clinton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/273,671

(22) Filed: Nov. 14, 2005

(65) Prior Publication Data

US 2006/0106007 A1 May 18, 2006

Related U.S. Application Data

(63) Continuation-in-part of application No. 11/110,589, filed on Apr. 20, 2005, now Pat. No. 7,273,859.

(60) Provisional application No. 60/570,348, filed on May 12, 2004.

(51) Int. Cl.
*C07F 9/40* (2006.01)
*C07D 267/08* (2006.01)
*C07D 487/10* (2006.01)
*C07D 265/28* (2006.01)
*A61K 31/665* (2006.01)
*A61K 31/553* (2006.01)
*A61K 31/505* (2006.01)
*A61K 31/527* (2006.01)
*A61K 31/535* (2006.01)
*A61K 31/537* (2006.01)

(52) U.S. Cl. .................. 514/81; 514/211.12; 514/267; 514/230.2; 544/230; 544/70; 544/71; 540/542; 540/543

(58) Field of Classification Search .................. 540/542, 540/543; 514/211.1, 211.12, 267, 230.2; 544/230, 70, 71
See application file for complete search history.

(56) References Cited

U.S. PATENT DOCUMENTS

2004/0006065 A1   1/2004   Giunz

FOREIGN PATENT DOCUMENTS

| WO | WO 03/035076 A1 | 5/2003 |
| WO | WO 03/035077 A1 | 5/2003 |
| WO | WO 2004/058756 A1 | 7/2004 |
| WO | WO 2004/058757 A1 | 7/2004 |
| WO | WO 2005/061490 A1 | 7/2005 |
| WO | WO 2005/061501 A2 | 7/2005 |
| WO | WO 2005/070901 A2 | 8/2005 |

OTHER PUBLICATIONS

U.S. Appl. No. 10/755,642, filed Jan. 12, 2004, Michael A. Walker et al.

*Primary Examiner*—James O. Wilson
*Assistant Examiner*—Susanna Moore
(74) *Attorney, Agent, or Firm*—James Epperson

(57) ABSTRACT

The invention encompasses a series of pyrimidinone compounds which inhibit HIV integrase and thereby prevent viral integration into human DNA. This action makes the compounds useful for treating HIV infection and AIDS. The invention also encompasses intermediates useful for making the pyrimidone compounds. Additionally, pharmaceutical compositions and methods for treating those infected with HIV are encompassed.

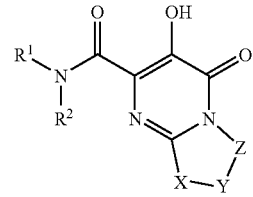

6 Claims, No Drawings

HIV INTEGRASE INHIBITORS: CYCLIC PYRIMIDINONE COMPOUNDS

CROSS REFERENCE TO RELATED APPLICATIONS

This application is a continuation-in-part of U.S. non-provisional application Ser. No. 11/110,589, filed Apr. 20, 2005, now U.S. Pat. No. 7,273,859 and claims the benefit of U.S. provisional application No. 60/570,348, filed May 12, 2004.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. And nevaripine, delavirdine and efavirenz are non-nucleoside reverse transcriptase inhibitors, which inhibit the synthesis of viral cDNA via a non-competitive (or uncompetitive) mechanism. When used alone these drugs are effective in reducing viral replication. The effect, however, is only temporary as the virus readily develops resistance to all known agents. Currently, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance due to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly there is a need for new antiviral agents, preferably targeting other viral enzymes to reduce the rate of resistance and suppress viral replication even further.

HIV expresses three enzymes: reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses a series of pyrimidinone compounds which inhibit HIV integrase and thereby prevent viral integration into human DNA. This action makes the compounds useful for treating HIV infection and AIDS. The invention also encompasses intermediates useful for making the pyrimidone compounds. Additionally, pharmaceutical compositions and methods for treating those infected with HIV are encompassed.

One aspect of the invention is a compound of Formula I

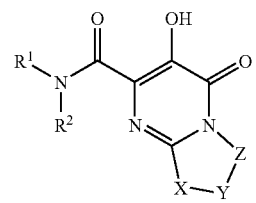

where:

$R^1$ is $C_{1-6}(Ar^1)$alkyl;

$R^2$ is hydrogen, $C_{1-6}$alkyl, or $OR^6$;

$R^3$ is hydrogen, halo, hydroxy, cyano, $C_{1-6}$alkyl, $C_{3-7}$cycloalkyl, $C_{1-6}$haloalkyl, $C_{1-6}$alkoxy, $C_{1-6}$alkylthio, $C_{1-6}$haloalkoxy, $CON(R^6)(R^6)$, $SOR^7$, $SO_2R^7$, $SO_2N(R^6)(R^6)$, or $Ar^2$;

$R^4$ is hydrogen, halo, hydroxy, cyano, $C_{1-6}$alkyl, $C_{1-6}$alkoxy, $C_{1-6}$haloalkyl, or $C_{1-6}$haloalkoxy;

$R^5$ is hydrogen, halo, hydroxy, cyano, $C_{1-6}$alkyl, $C_{1-6}$alkoxy, $C_{1-6}$haloalkyl, or $C_{1-6}$haloalkoxy;

$R^6$ is hydrogen or $C_{1-6}$alkyl;

$R^7$ is $C_{1-6}$alkyl;

$R^8$ and $R^9$ taken together are $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $OCH_2CH_2$, $CH_2OCH_2$, $OCH_2CH_2CH_2$, $CH_2OCH_2CH_2$, $OCH_2CH_2CH_2CH_2$, $CH_2OCH_2CH_2CH_2$, $CH_2CH_2OCH_2CH_2$, $OCH_2CH_2CH_2CH_2CH_2$, $CH_2OCH_2CH_2CH_2CH_2$, $CH_2CH_2OCH_2CH_2CH_2$, $N(R^6)CH_2CH_2$, $CH_2N(R^6)CH_2$, $N(R^6)CH_2CH_2CH_2$, $CH_2N(R^6)CH_2CH_2$, $N(R^6)CH_2CH_2CH_2CH_2$, $CH_2N(R^6)CH_2CH_2CH_2$, $CH_2CH_2N(R^6)CH_2CH_2$, $N(R^6)CH_2CH_2CH_2CH_2CH_2$, $CH_2N(R^6)CH_2CH_2CH_2CH_2$, or $CH_2CH_2N(R^6)CH_2CH_2CH_2$;

Ar¹ is

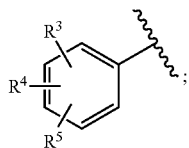

Ar² is tetrazolyl, triazolyl, imidazolyl, pyrazolyl, pyrrolyl, or dioxothiazinyl, and is substituted with 0-2 substituents selected from the group consisting of amino, oxo, halo, cyano, and $C_{1-6}$alkyl; and X—Y-Z is $C(R^8)(R^9)CH_2CH_2$, $C(R^8)(R^9)CH_2CH_2CH_2$, $C(R^8)(R^9)CH_2CH_2CH_2CH_2$, $C(R^8)(R^9)OCH_2$, $C(R^8)(R^9)OCH_2CH_2$, or $C(R^8)(R^9)OCH_2CH_2CH_2$;

or a pharmaceutically acceptable salt or solvate thereof.

Another aspect of the invention is a compound of Formula I where X—Y-Z is $C(R^8)(R^9)CH_2CH_2$, $C(R^8)(R^9)CH_2CH_2CH_2$, or $C(R^8)(R^9)CH_2CH_2CH_2CH_2$.

Another aspect of the invention is a compound of Formula I according to the following structures.

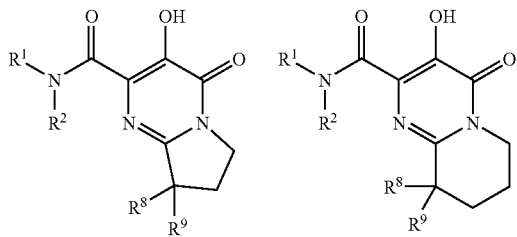

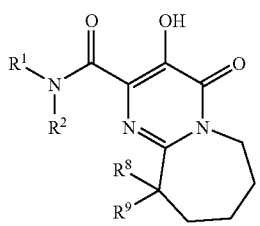

Another aspect of the invention is a compound of Formula I where X—Y-Z is $C(R^8)(R^9)OCH_2$, $C(R^8)(R^9)OCH_2CH_2$, or $C(R^8)(R^9)OCH_2CH_2CH_2$.

Another aspect of the invention is a compound of Formula I according to the following structures.

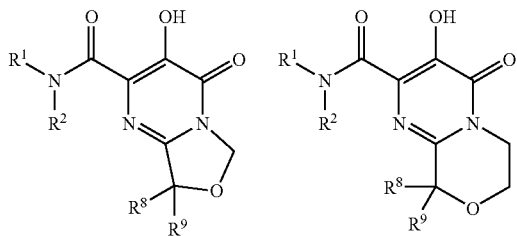

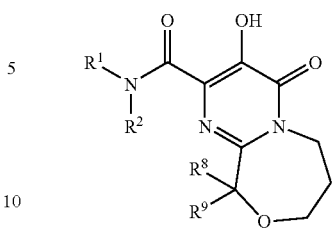

Another aspect of the invention is a compound of Formula I where $R^8$ and $R^9$ taken together are $CH_2CH_2CH_2$, $CH_2CH_2CH_2CH_2$, $CH_2CH_2CH_2CH_2CH_2$, $CH_2CH_2CH_2CH_2CH_2CH_2$, $CH_2OCH_2CH_2$, $CH_2CH_2OCH_2CH_2$, $CH_2N(R^6)CH_2CH_2$, or $CH_2CH_2N(R^6)CH_2CH_2$.

Another aspect of the invention is a compound of Formula I where $R^1$ is (Ar¹)methyl.

Another aspect of the invention is a compound of Formula I where $R^2$ is hydrogen.

Another aspect of the invention is a compound of Formula I where $R^3$ is fluoro, chloro, methyl, $CON(R^6)(R^6)$, or Ar².

Another aspect of the invention is a compound of Formula I where $R^4$ is hydrogen, fluoro, chloro, or methyl.

Another aspect of the invention is a compound of Formula I where $R^5$ is hydrogen.

Another aspect of the invention is a compound of Formula I where Ar¹ is

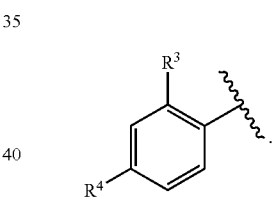

For a compound of Formula I, any scope of $R^1$, $R^2$, $R^3$, $R^4$, $R^5$, $R^6$, $R^7$, $R^8$ and $R^9$ taken together, and X—Y-Z can be used independently with any scope of any other substituent.

Another aspect of the invention is a compound of Formula II.

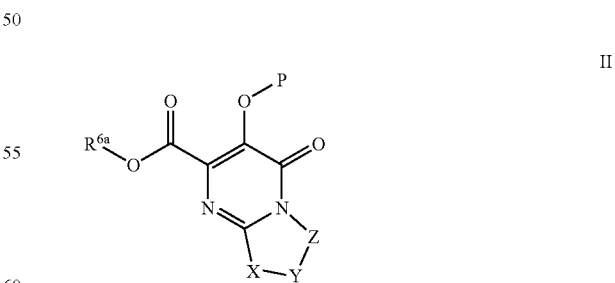

where
$R^{6a}$ is hydrogen, $C_{1-6}$alkyl, $C_{1-6}$(Ar¹)alkyl, ArC$_{1-6}$, C—(C≡C)n-C, $C_{1-6}$—O—$C_{1-6}$—O—$C_{1-6}$, $C_{1-6}$—O—$C_{1-6}$—Ar, $C(Ar)_{2-3}$, $CO(C_{1-6})_{1-3}$, or COAr; and P is hydrogen, mesyl, tosyl, allyl, benzyl, fluorenylmethyl, allyloxycarbonyl, benzyloxycarbonyl, fluorenylmethoxycarbonyl, tri($C_{1-6}$alkyl)silyl, $C_{1-6}$alkyl, $C_{1-6}$alkylcarbonyl, or $C_{1-6}$alkoxycarbonyl, $ArC_{1-6}$, C—(C═C)n-C, $C_{1-6}$—O—$C_{1-6}$—O—$C_{1-6}$, $C_{1-6}$—O—$C_{1-6}$—Ar, $CO(C_{1-6})_{1-3}$, COAr, or $C(Ar)_{2-3}$.

Another aspect of the invention is a compound of Formula II where $R^{6a}$ is hydrogen, $C_{1-6}$alkyl, or $C_{1-6}(Ar^1)$alkyl; and P is hydrogen, mesyl, tosyl, allyl, benzyl, fluorenylmethyl, allyloxycarbonyl, benzyloxycarbonyl, fluorenylmethoxycarbonyl, tri($C_{1-6}$alkyl)silyl $C_{1-6}$alkyl, $C_{1-6}$alkylcarbonyl, or $C_{1-6}$alkoxycarbonyl.

Some compounds of the invention are

N-[(4-fluorophenyl)methyl]-7',8'-dihydro-3'-hydroxy-4'-oxo-spiro[cyclopentane-1,9'(6'H)-[4H]pyrido[1,2-a]pyrimidine]-2'-carboxamide;

N-[(4-fluoro-3-methylphenyl)methyl]-7',8'-dihydro-3'-hydroxy-4'-oxo-spiro[cyclopentane-1,9'(6'H)-[4H]pyrido[1,2-a]pyrimidine]-2'-carboxamide;

N-[[2-(1H-1,2,4-triazol-1-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[4-fluoro-2-(1H-1,2,4-triazol-1-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[5-fluoro-2-(1H-1,2,4-triazol-1-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[4-fluoro-2-(2H-1,2,3-triazol-2-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[4-fluoro-2-(1H-imidazol-1-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[2-(tetrahydro-1,1-dioxido-2H-1,2-thiazin-2-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[4-fluoro-2-(tetrahydro-1,1-dioxido-2H-1,2-thiazin-2-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[2-[(dimethylamino)sulfonyl]-4-fluorophenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[4-fluoro-2-(methylsulfonyl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-[[3-fluoro-2-(1H-1,2,4-triazol-1-yl)phenyl]methyl]-7',8'-dihydro-3'-hydroxy-4'-oxo-spiro[cyclopentane-1,9'(6'H)-[4H]pyrido[1,2-α]pyrimidine]-2'-carboxamide;

N-(phenylmethyl)-7',8'-dihydro-3'-hydroxy-4'-oxo-spiro[cyclobutane-1,9'(6'H)-[4H]pyrido[1,2-α]pyrimidine]-2'-carboxamide;

N-[(4-methylphenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(4-methoxyphenyl)methyl]-7',8'-dihydro-3'-hydroxy-4'-oxo-spiro[cyclobutane-1,9'(6H)$^1$-[4H]pyrido[1,2-α]pyrimidine]-2'-carboxamide;

N-[(4-chlorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(4-fluorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(3-fluorophenyl)methyl]-7',8'-dihydro-3'-hydroxy-4'-oxo-spiro[cyclobutane-1,9'(6'H-[4H]pyrido[1,2-α]pyrimidine]-2'-carboxamide;

N-[(2-fluorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(3,4-dimethylphenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(3,4-dichlorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(2,4-dimethoxyphenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(4-fluoro-3-methylphenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(3-fluoro-4-methylphenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[1-(4-fluorophenyl)ethyl]-7',8'-dihydro-3'-hydroxy-4'-oxo-spiro[cyclobutane-1,9'(6'H)-[4H]pyrido[1,2-α]pyrimidine]-2'-carboxamide;

N-[(2,5-difluorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[(2,5-dichlorophenyl)methyl]-7',8'-dihydro-3'-hydroxy-4'-oxo-spiro[cyclobutane-1,9'(6'H)-[4H]pyrido[1,2-α]pyrimidine]-2'-carboxamide;

N-[[5-fluoro-2-(1H-1,2,4-triazol-1-yl)phenyl]methyl]-7',8'-dihydro-3'-hydroxy-4'-oxo-spiro[cyclobutane-1,9'(6'H)-[4H]pyrido[1,2-α]pyrimidine]-2'-carboxamide;

N-[[4-fluoro-2-(1H-1,2,4-triazol-1-yl)phenyl]methyl]-7',8'-dihydro-3'-hydroxy-4'-oxo-spiro[cyclobutane-1,9'(6'$^1$'H)-[4H]pyrido[1,2-α]pyrimidine]-2'-carboxamide;

N-[[4-fluoro-2-(tetrahydro-1,1-dioxido-2H-1,2-thiazin-2-yl)phenyl]methyl]-7',8'-dihydro-3'-hydroxy-4'-oxo-spiro[cyclobutane-1,9'(6'H)-[4H]pyrido[1,2-α]pyrimidine]-2'-carboxamide;

N-[[2-(1H-1,2,4-triazol-1-yl)phenyl]methyl]-7',8'-dihydro-3'-hydroxy-4'-oxo-spiro[cyclobutane-1,9'(6'H)-[4H]pyrido[1,2-α]pyrimidine]-2'-carboxamide;

N-[[4-fluoro-2-(methylsulfonyl)phenyl]methyl]-7',8'-dihydro-3'-hydroxy-4'-oxo-spiro[cyclobutane-1,9'(6'H)-[4H]pyrido[1,2-α]pyrimidine]-2'-carboxamide;

N-[[2-[(dimethylamino)sulfonyl]-4-fluorophenyl]methyl]-7',8'-dihydro-3'-hydroxy-4'-oxo-spiro[cyclobutane-1,9'(6'H)-[4H]pyrido[1,2-α]pyrimidine]-2'-carboxamide;

7',8'-dihydro-3'-hydroxy-4'-oxo-N-[[2-(tetrahydro-1,1-dioxido-2H-1,2-thiazin-2-yl)phenyl]methyl]-spiro[cyclobutane-1,9'(6'H)-[4H]pyrido[1,2-α]pyrimidine]-2'-carboxamide;

N-[(4-fluorophenyl)methyl]-6',7'-dihydro-3'-hydroxy-4'-oxo-spiro[cyclopentane-1,8'(4'H)-pyrrole[1,2-α]pyrimidine]-2'-carboxamide;

N-[[4-fluoro-2-(methylsulfonyl)phenyl]methyl]-6',7'-dihydro-3'-hydroxy-4'-oxo-spiro[cyclopentane-1,8'(4'H)-pyrrolo[1,2-α]pyrimidine]-2'-carboxamide;

N-[[2-[(dimethylamino)sulfonyl]-4-fluorophenyl]methyl]-6',7'-dihydro-3'-hydroxy-4'-oxo-spiro[cyclopentane-1,8'(4'H)-pyrrolo[1,2-α]pyrimidine]-2'-carboxamide;

N-[[4-fluoro-2-(1H-1,2,4-triazol-1-yl)phenyl]methyl]-6',7'-dihydro-3'-hydroxy-4'-oxo-spiro[cyclopentane-1,8'(4'H)-pyrrolo[1,2-α]pyrimidine]-2'-carboxamide;

N-[(4-fluorophenyl)methyl]-2,3,5,6,7',8'-hexahydro-3'-hydroxy-4'-oxo-spiro[4H-pyran-4,9'(6'H)-[4H]pyrido[1,2-a]pyrimidine]-2'-carboxamide;

N-(phenylmethyl)-6',7'-dihydro-3'-hydroxy-4'-oxo-spiro[cyclopentane-1,9'(4'H)-pyrimido[2,1-c][1,4]oxazine]-2'-carboxamide;

N-[(4-fluorophenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[(4-fluoro-3-methylphenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(1 H-1,2,4-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(methylthio)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

6',7'-dihydro-3'-hydroxy-N-[(4-methylphenyl)methyl]-4'-oxo-spiro[cyclopentane-1,9'(4'H)-pyrimido[2,1-c][1,4]oxazine]-2'-carboxamide;

N-[(4-chlorophenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[(3,4-dichlorophenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[(3,4-dimethylphenyl)methyl]-6',7'-dihydro-3'-hydroxy-4'-oxo-spiro[cyclopentane-1,9'(4'H)-pyrimido[2,1-c][1,4]oxazine]-2'-carboxamide;

6',7'-dihydro-3'-hydroxy-N-[(4-methoxyphenyl)methyl]-4'-oxo-spiro[cyclopentane-1,9'(4'H)-pyrimido[2,1-c][1,4]oxazine]-2'-carboxamide;

N-[(2-fluorophenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[(2,4-dimethoxyphenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[(3-fluorophenyl)methyl]-6',7'-dihydro-3 '-hydroxy-4'-oxo-spiro[cyclopentane-1,9'(4'H)-pyrimido[2,1-c][1,4]oxazine]-2'-carboxamide;

N-[(3-fluoro-4-methylphenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[[(2-(dimethylamino)sulfonyl]-4-fluorophenyl)methyl]-6',7'-dihydro-3'-hydroxy-4'-oxo-spiro[cyclopentane-1,9'(4'H)-pyrimido[2,1-c][1,4]oxazine]-2'-carboxamide;

N-[[5-fluoro-2-(1H-1,2,4-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[2-(4-fluorophenyl)ethyl]-6',7'-dihydro-3'-hydroxy-4'-oxo-spiro[cyclopentane-1,9'(4H)-pyrimido[2,1-c][1,4]oxazine]-2'-carboxamide;

N-[3-(4-fluorophenyl)propyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(5-methyl-1H-1,2,4-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

6',7'-dihydro-3'-hydroxy-4'-oxo-N-[[2-(1H-1,2,4-triazol-1-yl)phenyl]methyl]-spiro[cyclopentane-1,9'(4'H)-pyrimido[2,1-c][1,4]oxazine]-2'-carboxamide;

N-[[4-fluoro-2-(tetrahydro-1,1-dioxido-2H-1,2-thiazin-2-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

6',7'-dihydro-3'-hydroxy-4'-oxo-N-[[2-(tetrahydro-1,1-dioxido-2H-1,2-thiazin-2-yl)phenyl]methyl]-spiro[cyclopentane-1,9'(4'H)-pyrimido[2,1-c][1,4]oxazine]-2'-carboxamide;

N-[(4-fluorophenyl)methyl]-4,5,6',7'-tetrahydro-3'-hydroxy-4'-oxo-spiro[furan-3(2H),9'(4'H)-pyrimido[2,1-c][1,4]oxazine]-2'-carboxamide;

N-[(4-fluoro-3-methylphenyl)methyl]-4,5,6',7'-tetrahydro-3'-hydroxy-4'-oxo-spiro[furan-3(2H),9'(4'H)-pyrimido[2,1-c][1,4]oxazine]-2'-carboxamide;

N-[[4-fluoro-2-(1 H-1,2,4-triazol-1-yl)phenyl]methyl]-4,5,6',7'-tetrahydro-3'-hydroxy-4'-oxo-spiro[furan-3(2H),9'(4'H)-pyrimido[2,1-c][1,4]oxazine-2')-carboxamide;

N-[[4-fluoro-2-(methylthio)phenyl]methyl]-4,5,6',7'-tetrahydro-3'-hydroxy-4'-oxo-spiro[furan-3(2H),9'(4'H)-pyrimido[2,1-c][1,4]oxazine]-2'-carboxamide;

N-[(4-fluorophenyl)methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(1 H-1,2,4-triazol-1-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine-2')-carboxamide;

N-[[4-fluoro-2-(tetrahydro-1,1-dioxido-2H-1,2-thiazin-2-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[2-(tetrahydro-1,1-dioxido-2H-1,2-thiazin-2-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(methylsulfonyl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[(4-fluoro-3-methylphenyl)methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[(2,4-dimethoxyphenyl)methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[2-[(dimethylamino)sulfonyl]-4-fluorophenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide N-[(3,4-dimethylphenyl)methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(5-methyl-1H-1,2,4-triazol-1-yl)phenyl]methyl]-2,3,5,6,6', 7-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(3-methyl-1H-1,2,4-triazol-1-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(1H-1,2,4-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[(4-fluorophenyl)methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(methylsulfonyl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-[(dimethylamino)sulfonyl]-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(tetrahydro-1,1-dioxido-2H-1,2-thiazin-2-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(tetrahydro-1,1-dioxido-2H-1,2-thiazin-2-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(5-methyl-1H-1,2,4-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(methylsulfonyl)phenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[(4-fluorophenyl)methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(1 H-1,2,4-triazol-1-yl)phenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[2-[(dimethylamino)sulfonyl]-4-fluorophenyl]methyl]-7',8'-dihydro-3'-hydroxy-4'-oxo-spiro[cyclobutane-1,10'(4'H)-[6H]pyrimido[2,1-c][1,4]oxazepine]-2-carboxamide;

N-[(4-fluorophenyl)methyl]-6',7'-dihydro-3'-hydroxy-4'-oxo-spiro[piperidine-4,9'(4'H)-pyrimido[2,1-c][1,4]oxazine]-2'-carboxamide N-[[4-fluoro-2-(methylsulfonyl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(methylsulfonyl)phenyl]methyl]-4,5,6',7'-tetrahydro-3'-hydroxy-4'-oxo-spiro[furan-3(2H),9'(4'H)-pyrimido[2,1-c][1,4]oxazine]-2'-carboxamide; and N-[[4-fluoro-2-[(methylamino)carbonyl]phenyl]methyl]-6',7'-dihydro-3'-hydroxy-4'-oxo-spiro[cyclobutane-1,9'(4'H)-pyrimido[2,1-c][1,4]oxazine]-2'-carboxamide;

and salts and solvates of these compounds.

Some other compounds of Formula I include

N-[(4-fluorophenyl)methyl]-7',8'-dihydro-3'-hydroxy-8'-methyl-4'-oxo-spiro[cyclopentane-1,9'(6'H)-[4H]pyrazino[1,2-a]pyrimidine]-2'-carboxamide;

N-[[4-fluoro-2-(1H-1,2,4-triazol-1-yl)phenyl]methyl]-7',8'-dihydro-3'-hydroxy-8'-methyl-4'-oxo-spiro[cyclopentane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8'-methyl-4'-oxo-spiro[cyclopentane-1,9'(6'H)-[4H]pyrazino[1,2-a]pyrimidine]-2'-carboxamide;

N-[(4-fluorophenyl)methyl]-7',8'-dihydro-3'-hydroxy-8'-methyl-4'-oxo-spiro[cyclohexane-1,9'(6'H)-[4H]pyrazino[1,2-a]pyrimidine]-2'-carboxamide;

N-[[4-fluoro-2-(1H-1,2,4-triazol-1-yl)phenyl]methyl]-7',8'-dihydro-3'-hydroxy-8'-methyl-4'-oxo-spiro[cyclohexane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8'-methyl-4'-oxo-spiro[cyclohexane-1,9'(6'H)-[4H]pyrazino[1,2-a]pyrimidine]-2'-carboxamide;

N-[(4-fluorophenyl)methyl]-7',8'-dihydro-3'-hydroxy-8'-methyl-4'-oxo-spiro[cyclobutane-1,9'(6'H)-[4H]pyrazino[1,2-a]pyrimidine]-2'-carboxamide;

N-[[4-fluoro-2-(1H-1,2,4-triazol-1-yl)phenyl]methyl]-7',8'-dihydro-3'-hydroxy-8'-methyl-4'-oxo-spiro[cyclobutane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8'-methyl-4'-oxo-spiro[cyclobutane-1,9'(6'H)-[4H]pyrazino[1,2-a]pyrimidine]-2'-carboxamide;

N-[[4-fluoro-2-(1H-1,2,3-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(4,5-dimethyl-1H-1,2,3-triazol-1-yl)-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-[4-(1,1-dimethylethyl)-1H-1,2,3-triazol-1-yl]-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(5-methyl-1H-1,2,3-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(2-oxo-3-oxazolidinyl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(2-oxo-1-azetidinyl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(4,5-dimethyl-1H-1,2,3-triazol-1-yl)-4-fluorophenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[(4-fluorophenyl)methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(1H-1,2,4-triazol-1-yl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(methylsulfonyl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(1H-1,2,3-triazol-1-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(1H-1,2,3-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[(4-fluorophenyl)methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-[(methylamino)carbonyl]phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(methylsulfonyl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

[5-fluoro-2-[[[(2,3,5,6,7',8'-hexahydro-3 '-hydroxy-4'-oxospiro[4H-pyran-4,10'(4'H)-[6H]pyrimido[2,1-c][1,4]oxazepin]-2'-yl)carbonyl]amino]methyl]phenyl]-phosphonic acid, dimethyl ester;

N-[[4-fluoro-2-(1H-1,2,4-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(5-methyl-1H-1,2,4-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

2,3,5,6,7',8'-hexahydro-3'-hydroxy-N-[[2-(3-methyl-1H-1,2,4-triazol-1-yl)phenyl]methyl]-4'-oxo-spiro[4H-pyran-4,10'(4'H)-[6H]pyrimido[2,1-c][1,4]oxazepine]-2'-carboxamide;

N-[[4-fluoro-2-(1H-1,2,3-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

6',7'-dihydro-3'-hydroxy-4'-oxo-N-[[2-(2-oxo-1-azetidinyl)phenyl]methyl]-spiro[cyclobutane-1,9'(4'H)-pyrimido[2,1-c][1,4]oxazine]-2'-carboxamide;

6',7'-dihydro-3'-hydroxy-4'-oxo-N-[[2-(2-oxo-3-oxazolidinyl)phenyl]methyl]-spiro[cyclobutane-1,9'(4'H)-pyrimido[2,1-c][1,4]oxazine]-2'-carboxamide;

N-[[2-(3,5-dimethyl-1H-1,2,4-triazol-1-yl)-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(3,5-dimethyl-1H-1,2,4-triazol-1-yl)-4-fluorophenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[cyclopentane-1,9'(4'H)-pyrimido[2,1--c][1,4]oxazine]-2'-carboxamide;

N-[[2-(3,5-dimethyl-1H-1,2,4-triazol-1-yl)-4-fluorophenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(1H-1,2,4-triazol-1-yl)phenyl]methyl]-7',8'-dihydro-3'-hydroxy-4'-oxo-spiro[cyclobutane-1,9'(6'H)-[4H]pyrazino[1,2-a]pyrimidine]-2'-carboxamide;

N-[(4-fluorophenyl)methyl]-7',8'-dihydro-3'-hydroxy-4'-oxo-spiro[cyclobutane-1,9'(6'H)-[4H]pyrazino[1,2-a]pyrimidine]-2'-carboxamide;

and pharmaceutically acceptable salts and solvates of these compounds.

"Alkyl," "alkoxy," "haloalkyl," and related terms for other hydrocarbon and substituted hydrocarbon substituents include straight and branched isomeric configurations. A term such as "$C_{1-6}$(R)alkyl" means a straight or branched alkyl group of 1 to 6 carbons substituted with the substituent R. "Haloalkyl" and related terms for halogenated substituents include all permutations of halogenation, from monohaloalkyl to perhaloalkyl. "Aryl" means an aromatic ring system and includes carbocyclic and heterocyclic systems. Some substituents are divalent, for example, X—Y-Z. Divalent substituents which are asymmetric can be attached to the parent molecule in either of the configurations.

"Dioxothiazinyl" means

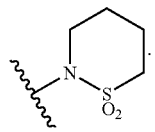

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

The invention includes all tautomeric forms of the compounds. An example of a tautomeric pair is shown below.

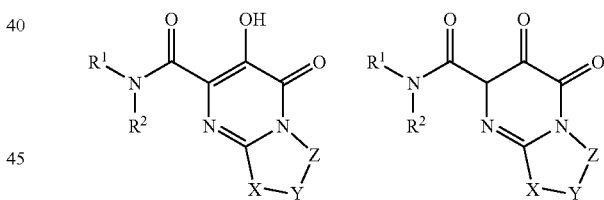

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

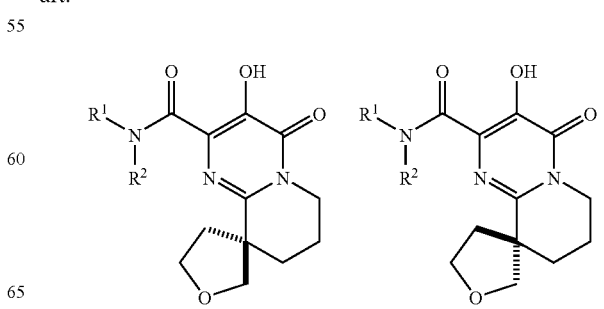

Synthetic Methods

The compounds of this invention can be made by various methods known in the art including those of the following schemes and in the specific embodiments section. The variables shown in the schemes (for example, X, n, and P) are separate from and should not be confused with the variables in the claims or the rest of the specification. The variables in the schemes are meant only to illustrate how to make some of the compounds of this invention. "X" and "n" include alkylene spacers which may contain ether or amino functionalities. "P" may include an appropriate protecting group. Starting materials can be made using methods known in the art.

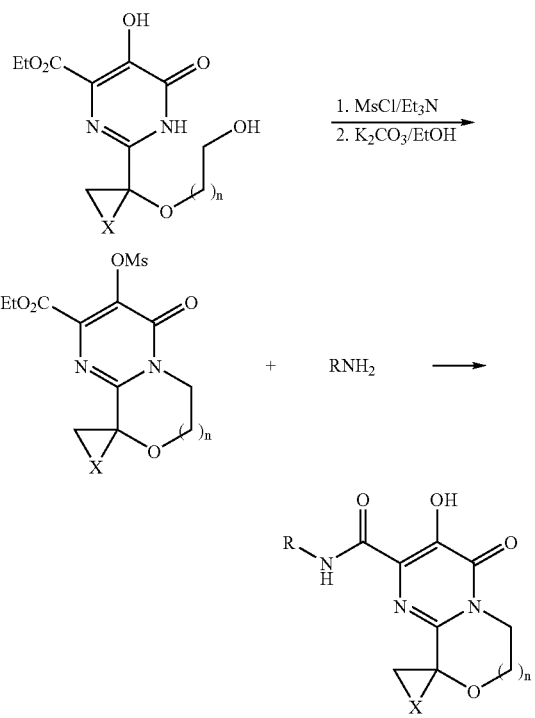

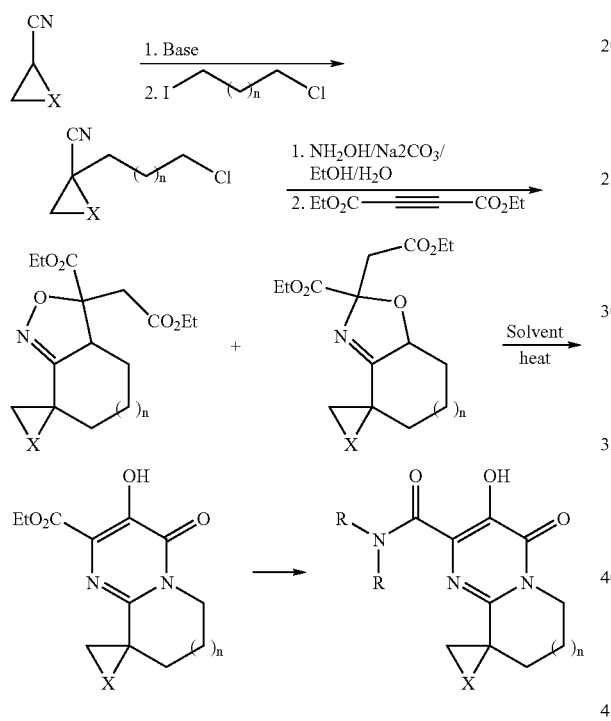

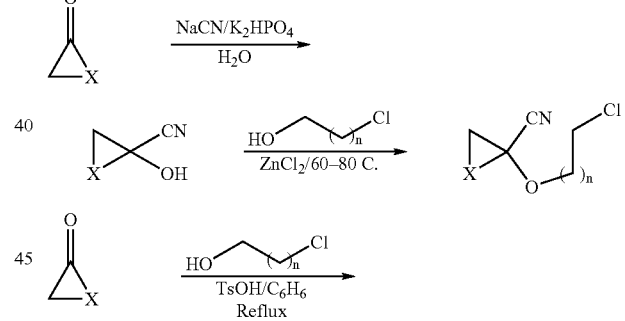

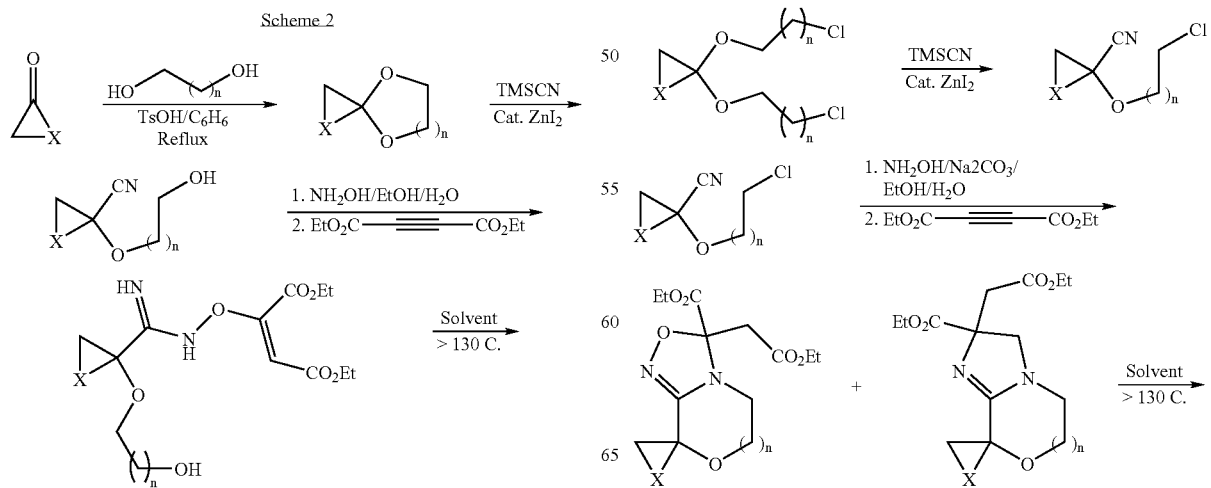

-continued

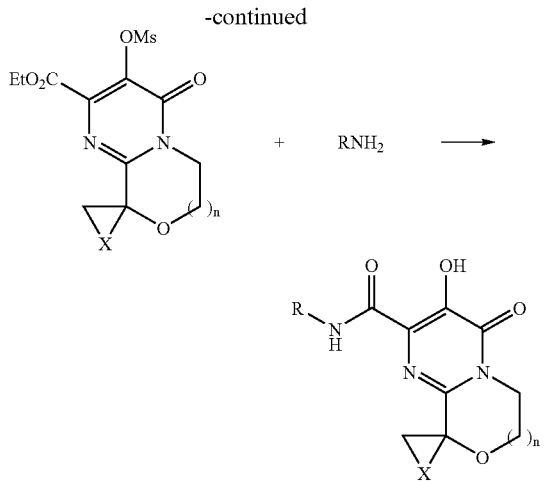

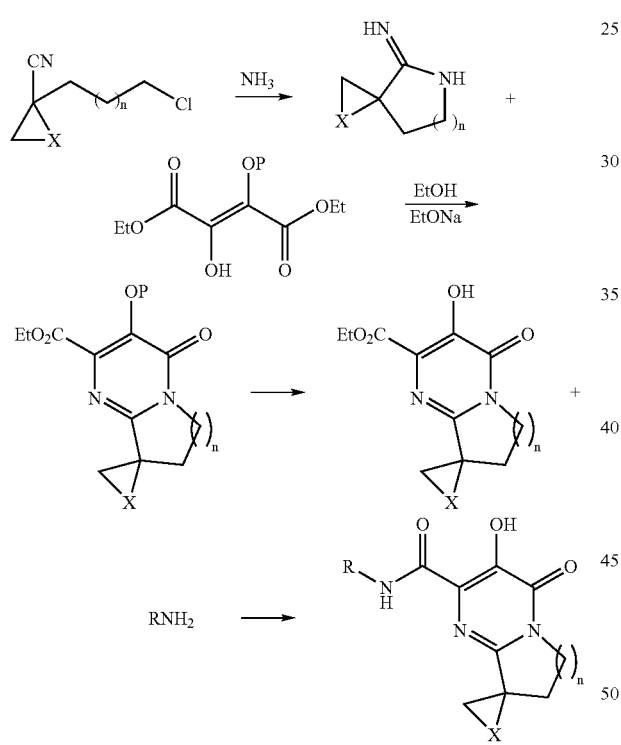

Biological Methods

To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 mmol of P33 labeled target DNA. The reaction was stopped by adding EDTA to a final concentration of 10 mM. Samples were counted in TopCountNXT (Packard) and the CPM was used as a measure of integration. The reaction condition was as described in Engelman, A. and Craigie, R. *J. Vitrol.* 1996, 69, 5908. The sequences of substrate and target DNA were described in *Nucleic Acid Research* 1994, 22, 1121. Using this assay, the compound of this invention were found to have an $IC_{50}$ from less than 0.1 μM (see Tables 1 and 1a).

TABLE 1

| HIV Integrase Inhibition | |
|---|---|
| Example | $IC_{50}$ |
| 1 | A |
| 2 | A |
| 3 | A |
| 4 | A |
| 5 | A |
| 6 | A |
| 7 | A |
| 8 | B |
| 9 | A |
| 10 | A |
| 11 | A |
| 12 | A |
| 13 | A |
| 14 | A |
| 15 | A |
| 16 | A |
| 17 | A |
| 18 | A |
| 19 | B |
| 20 | A |
| 21 | A |
| 22 | B |
| 23 | B |
| 24 | B |
| 25 | B |
| 26 | B |
| 27 | A |
| 28 | A |
| 29 | A |
| 30 | B |
| 31 | B |
| 32 | A |
| 33 | A |
| 34 | A |
| 35 | B |
| 36 | A |
| 37 | A |
| 38 | A |
| 39 | A |
| 40 | A |
| 41 | A |
| 42 | A |
| 43 | B |
| 44 | A |
| 45 | A |
| 46 | B |
| 47 | B |
| 48 | A |
| 49 | A |
| 50 | A |
| 51 | A |
| 52 | A |
| 53 | A |
| 54 | A |
| 55 | A |
| 56 | B |
| 57 | A |
| 58 | B |
| 59 | A |
| 60 | A |
| 61 | B |
| 62 | A |
| 63 | B |
| 64 | B |
| 65 | A |
| 66 | A |
| 67 | A |
| 68 | B |

TABLE 1-continued

HIV Integrase Inhibition

| Example | IC$_{50}$ |
|---|---|
| 69 | A |
| 70 | A |
| 71 | B |
| 72 | A |
| 73 | A |
| 74 | B |
| 75 | B |
| 76 | A |
| 77 | A |
| 78 | A |
| 79 | A |
| 80 | A |
| 81 | A |
| 82 | A |
| 83 | B |
| 84 | A |
| 85 | A |
| 86 | B |
| 87 | A |
| 88 | B |
| 89 | A |
| 90 | B |
| 91 | A |

Activity. A: 0.001-0.01 µM;
B: 0.01-0.1 µM.

TABLE 1a

HIV Integrase Inhibition

| Example | IC$_{50}$ |
|---|---|
| 92 | A |
| 93 | A |
| 94 | B |
| 95 | A |
| 96 | A |
| 97 | B |
| 98 | A |
| 99 | A |
| 100 | B |
| 101 | A |
| 102 | B |
| 103 | B |
| 104 | A |
| 105 | A |
| 106 | A |
| 107 | B |
| 108 | A |
| 109 | A |
| 110 | A |
| 111 | B |
| 112 | A |
| 113 | A |
| 114 | A |
| 115 | A |
| 116 | B |
| 117 | B |
| 118 | A |
| 119 | A |
| 120 | B |
| 121 | B |
| 122 | A |
| 123 | A |
| 124 | A |
| 125 | A |
| 126 | A |
| 127 | B |
| 128 | B |
| 129 | A |
| 130 | A |
| 131 | A |
| 132 | A |

Activity. A: 0.001-0.01 µM;
B: 0.01-0.1 µM

Pharmaceutical Composition and Methods of Use

The compounds of this invention inhibit HIV integrase. HIV integrase inhibitors have been reported to prevent viral integration and inhibited HIV-1 replication in cells (Hazuda et al. *Science* 2000, 287, 646). Recently, HIV integrase inhibitors have been accepted into clinical trials for treating AIDS and HIV infection (Neamati Expert. *Opin. Ther. Patents* 2002, 12, 709, Pais and Burke *Drugs Fut.* 2002, 27, 1101).

Accordingly, another aspect of the invention is a method for treating HIV infection in a patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a patient comprising administering a therapeutically effective amount of a compound of Formula I, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition comprising a therapeutically effective amount of a compound of Formula I, or a pharmaceutically acceptable salt or solvate thereof, with a pharmaceutically acceptable carrier.

"Combination," "coadministration," "concurrent," and similar terms referring to the administration of compounds of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional exipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgment.

Table 2 lists some agents useful in treating AIDS and HIV infection which are suitable for this method.

TABLE 2

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse | Hoechst Marion Roussel | HIV infection, AIDS, ARC |

TABLE 2-continued

| DRUG NAME | MANUFACTURER | INDICATION |
|---|---|---|
| transcriptase inhibitor) | | |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |

IMMUNOMODULATORS

| DRUG NAME | MANUFACTURER | INDICATION |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, in combination w/AZT ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| DRUG NAME | MANUFACTURER | INDICATION |
|---|---|---|
| Clindamycin with Primaquine | Pharmacia Upjohn | PCP |

TABLE 2-continued

| DRUG NAME | MANUFACTURER | INDICATION |
|---|---|---|
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Intermediate 1

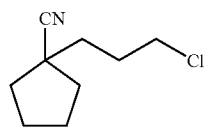

1-(3-chloropropyl)cyclopentanecarbonitrile. To a stirred solution of cyclopentanecarbonitrile (1.04 mL, 10 mmol) in THF (20 mL) at −78° C. was added LiHMDS (1M in THF, 11 mL) via syringe. After 30 min, 1-chloro-3-iodopropane (1.6 mL, 15 mmol) was added at once and slowly warmed to room temperature. After 20 h, the reaction mixture was quenched with saturated ammonium chloride (1 mL), diluted with EtOAc (100 mL), dried (MgSO$_4$), filtered and concentrated to give intermediate 1 as yellow oil which was used in the next step without further purification.

Intermediate 2

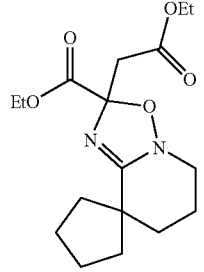

To a stirred mixture of intermediate 1 from previous experiment and hydroxylamine hydrochloride (1.39 g, 20 mmol) in 1:1 EtOH/water (30 mL) was added sodium carbonate (1.6 g, 15 mmol) over 5 min. Then, the reaction mixture was stirred to 80° C. for 15 h and concentrated to dryness. The resulting white residue was re-dissolved into 1:1 EtOH/water (30 mL) and diethyl acetylenedicarboxylate (2.4 mL, 15 mmol) was added. After 1 h, the reaction mixture was diluted with water (50 mL) and extracted with EtOAc (3×50 mL). The combined EtOAc extracts dried (Na$_2$SO$_4$), filtered and concentrated to give brown oil. Flash chromatography using 9:1, 4:1 and 7:1 Hexanes/EtOAc mixtures afforded intermediate 2 as pale yellow oil (1.03 g, 30%). $^1$H NMR (500 MHz, CDCl$_3$) δ: 4.34-4.11 (4H, m), 3.50-3.46 (1H, m), 3.38-3.34 (1H, m), 3.31 (1H, d, J=16.2 Hz), 2.91 (1H, d, J=16.2 Hz), 2.23-2.13 (2H, m), 1.95-1.89 (2H, m), 1.74-1.69 (2H, m), 1.62 (2H, t, J=5.9 Hz), 1.54-1.48 (2H, m), 1.34-1.23 (8H, m). HRMS (M+H) calcd for C$_{17}$H$_{27}$N$_2$O$_5$: 339.1920; found: 339.1923.

Intermediate 3

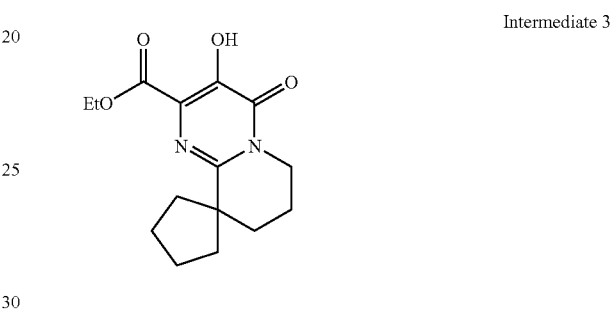

A solution of intermediate 2 (1.0 g, 2.955 mmol) in 3,4-dichlorotoluene (10 mL) was heated at 210° C. for 15 h. Then, the reaction mixture was concentrated under vacuum and the residue was purified by preparative HPLC using MeOH/water containing 0.1% TFA (gradient elution). The fractions containing the product were combined and concentrated to afford intermediate 3 as a dark paste (0.8639 g, 28.6%). $^1$H NMR (500 MHz, CDCl$_3$) δ: 10.75 (1H, br s), 4.43 (2H, q, J=7.0 Hz), 4.03 (2H, t, J=5.8 Hz), 2.25-2.20 (2H, m), 1.99-1.93 (4H, m), 1.79-1.64 (6H, m), 1.42 (3H, t, J=7.0 Hz),. HRMS (M+H) calcd for C$_{15}$H$_{21}$N$_2$O$_4$: 293.1501; found: 293.1513.

Intermediate 4

Tetrahydro-2H-pyran-4-carbonitrile. A solution of tetrahydro-4H-pyran-4-one (25 g, 250 mmol) and toluenesulfonylmethyl cyanide (53.7 g, 275 mmol) dissolved in ethylene glycol dimethylether (1 L) was cooled to 0° C. Added dropwise over 30 min was a solution of potassium t-butoxide (56 g, 500 mmol) dissolved in t-butanol (350 mL) and ethylene glycol dimethylether (150 mL). After stirring the resulting mixture for 3 h at room temp, diethyl ether (1 L) was added and the organic phase was washed with saturated aqueous NaHCO$_3$. The organic phase was dried (Na$_2$SO$_4$) and concentrated. The residue was distilled at 39° C. 1.7 mm Hg to give the title compound as a colorless oil (10.87 g, 39% yield).

¹H NMR (300 MHz, CDCl₃) δ: 3.91-3.83 (2H, m), 3.61-3.54 (2H, m), 2.89-2.80 (1H, m), 1.97-1.78 (4H, m).

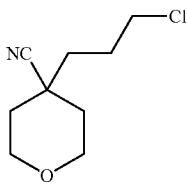

Intermediate 5

4-(3-chloropropyl)-tetrahydro-2H-pyran-4-carbonitrile. To a stirred solution of 1 M LiHMDS (25 mL, 25 mmol) in THF (10 mL) at −78° C. was added dropwise a solution of intermediate 4 (2.23 g, 20 mmol) in THF (15 mL) over 10 minutes. After 40 min, 1-chloro-3-iodopropane (2.7 mL, 25 mmol) was added at once, stirred at −78° C. for 1 h and 4 h room temperature. Then the reaction mixture was diluted with ether (100 mL), washed with water (20 mL) and brine (20 mL), dried (Na₂SO₄), filtered and concentrated to give yellow oil which was purified by flash column chromatography using 10-30% EtOAc/Hexanes to afford the product intermediate 5 as a colorless liquid (3.737 g, 99%). ¹H NMR (500 MHz, CDCl₃) δ: 3.97 (2H, dd, J=11.3, 3.7 Hz), 3.71 (2H, td, J=12.2, 1.8 Hz), 3.61 (2H, t, J=6.3 Hz), 2.05-1.98 (2H, m), 1.88 (2H, dd, J=13.4, 1.8 Hz), 1.77-1.74 (2H, m), 1.65-1.59 (2H, m).

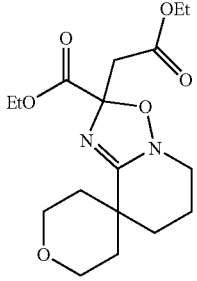

Intermediate 6

A mixture of intermediate 5 (1.83 g, 9.75 mmol) and NaI (3.0 g, 20 mmol) was stirred at ambient temperature for 1 h. To this reaction mixture was added 50% aqueous hydroxylamine (1 mL, 10.87 mmol mmol) and stirred for three-days at ambient temperature. To this was added diethyl acetylenedicarboxylate (1.6 mL, 10 mmol) and stirred for 1 h. Then, the reaction mixture was diluted with EtOAc (100 mL) washed with water (50 mL), brine (10 mL), dried (Na₂SO₄), filtered and concentrated to give yellow oil. Flash chromatography using 10-50% EtOAc/Hexanes afforded the desired intermediate 6 as pale yellow oil (0.627 g, 18% %). ¹H NMR (500 MHz, CDCl₃) δ: HRMS (M+H) calcd for C₁₇H₂₇N₂O₅;: found. ¹H NMR (500 MHz, CDCl₃) δ: 4.32-4.20 (2H, m), 4.14 (2H, q, J=7.0 Hz), 3.86 (1H, td, J=11.0, 2.7 Hz), 3.79-3.70 (3H, m), 3.52-3.46 (1H, m), 3.38-3.34 (1H, m), 3.26 (1H, d, J$_{AB}$=16.2 Hz), 2.97 (1H, d, J$_{AB}$=16.2 Hz), 2.06-1.89 (4H, m), 1.66-1.66 (2H, m), 1.60-1.53 (2H, m), 1.30 (3H, t, J=7.0 Hz), 1.24 (3H, t, J=7.0 Hz).

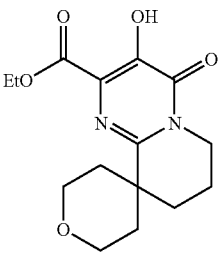

Intermediate 7

A solution of intermediate 6 (1.0 g, 2.955 mmol) in cyclohexylbenzene (25 mL) was heated at 200° C. for 15 h. Then, the reaction mixture was concentrated under vacuum and the residue was purified by preparative HPLC using MeOH/water containing 0.1% TFA (gradient elution). The fractions containing the product were combined and concentrated to afford intermediate 7 as an off-white solid (0.1263 g, 23%).¹H NMR (500 MHz, CDCl₃) δ: 10.35 (1H, br s), 4.45 (2H, q, J=7.0 Hz), 4.09-4.05 (2H, m), 4.01-3.99 (2H, m), 3.74-3.69 (2H, m), 2.35-2.29 (2H, m), 2.02-1.93 (4H, m), 1.59-1.54 (2H, m), 1.44 (3H, t, J=7.0 Hz). HRMS (M+H) calcd for C₁₅H₂₁N₂O₄: 309.1451; found: 309.1463.

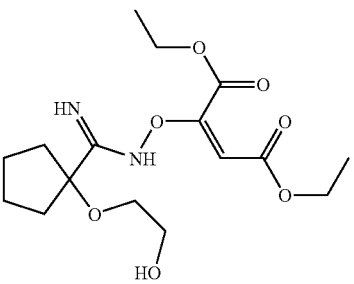

Intermediate 8

(E)-2-{[1-(2-Hydroxyethoxy)cyclopentanecarboximidoyl]-aminooxy}but-2-enedioic acid diethyl ester. A stirred mixture of cyclopentanone ethylene ketal (12.82 g, 100 mmol) and ZnI₂ (45 mg, catalytic) was placed in water bath and to this was added trimethylsilyl cyanide (13.35 mL, 100 mmol) via syringe over 10 min. After 16 h, EtOH (100 mL) followed by 50% aqueous hydroxylamine (6.43 mL, 100 mmol) was added and stirred at 80° C. for 2 h. Then, the reaction mixture was cooled in ice-water bath and diethyl acetylenedicarboxylate (16 mL, 100 mmol) was added over 5 min. Then, cooled bath removed, stirred for 4 h at room temperature and concentrated to give intermediate 8 as a dark-brown oil which was used in the next step without purification. LRMS (M+H) calcd for C₁₆H₂₇N₂O₇: 359.2; found: 359.2.

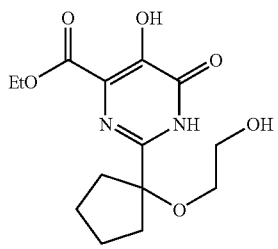

Intermediate 9

5-Hydroxy-2-[3-(2-hydroxy-ethoxy)tetrahydrofuran-3-yl]-6-oxo-1,6-dihydropyrimidine-4-carboxylic acid ethyl ester. A xylenes (200 ml) solution of crude intermediate 8 (100 mmol) was heated at reflux for 24 h, cooled and concentrated. The resulting dark-residue was stirred with 0.5 M $Na_2CO_3$ (150 mL) for 30 min and extracted with EtOAc (3×50 mL). The combined organic phases were re-extracted with 0.5 M $Na_2CO_3$ (50 mL) and EtOAc extracts discarded. The combined aqueous layers was carefully acidified with conc. HCl (20 mL) and extracted with $CH_2Cl_2$ (4×50 mL). The combined $CH_2Cl_2$ layers dried ($Na_2SO_4$/activated charcoal), filtered and concentrated to give brown solid which triturated with ether and filtered to afford intermediate 9 as a light brown powder (11.81 g, 38%). This material is contaminated with about 15% of an identified impurity whose M+1=295. LRMS (M+H) calcd for $C_{14}H_{21}N_2O_6$: 313.32; found: 313.27.

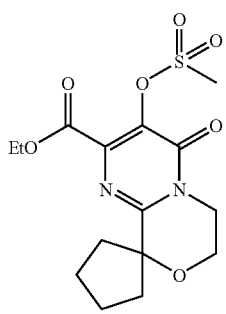

Intermediate 10

To a stirred solution of crude intermediate 9 (11.67 g) in THF (100 mL) at 5° C. was added MsCl (8.7 mL, 112.4 mmol) followed by Et3N (15.8 mL, 112.5 mmol). The resulting turbid reaction mixture was stirred for 4 h while allowing it to warm to room temperature. Then diluted with EtOAc (200 mL), washed with water (2×50 mL), brine (50 mL), dried ($Na_2SO_4$), filtered and concentrated to give viscous yellow oil. This oil was re-dissolved in anhydrous EtOH (100 mL) and stirred with $K_2CO_3$ (4.15 g, 30 mmol). After 4 h, the viscous slurry was diluted with EtOAc (150 mL) and continued stirring for additional 1 h. Then, the reaction mixture was filtered and concentrated to give white solid which was triturated with ether, and filtered to afford intermediate 10 as a white fluffy solid (8.284 g, 64%). $^1$H NMR (500 MHz, $CDCl_3$) δ: 4.43 (2H, q, J=7.0 Hz), 3.99 (4H, s), 3.53 (3H, s), 2.33-2.28 (2H, m), 2.09-2.05 (2H, m), 1.93-1.82 (4H, m), 1.40 (3H, t, J=7.0 Hz). HRMS (M+H) calcd for $C_{15}H_{21}N_2O_7S$: 373.1069; found: 373.1053.

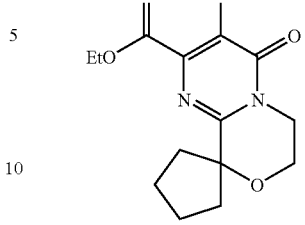

Intermediate 11

To a stirred suspension of intermediate 10 (0.6861 g, 1.84 mmol) in THF (50 mL) was added 1M EtONa/EtOH (10 mL). After 1 h, the resulting yellow solution was concentrated, acidified with 1 M aq. HCl (20 mL), extracted with $CH_2Cl_2$ (3×35 mL). The combined organic layers dried ($Na_2SO_4$), filtered and concentrated to give intermediate 11 as a brown solid (0.4668 g, 86%). $^1$H NMR (500 MHz, $CDCl_3$) δ: 10.49 (1H, s), 4.44 (2H, q, J=7.0 Hz), 4.03-3.97 (4H, m), 2.28-2.22 (2H, m) 2.06-2.01 (2H, m), 1.93-1.81 (4H, m), 1.42 (3H, t, J=7.0 Hz). HRMS (M+H) calcd for $C_{14}H_{19}N_2O_5$: 295.1294; found: 295.1293.

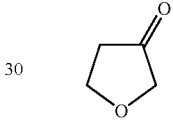

Intermediate 12

Dihydrofuran-3(2H)-one. A mixture of 3-hydroxyfuran (24 g, 272 mmol) and TEMPO (0.86 g, 5.5 mmol) in $CH_2Cl_2$ (175 mL) and KBr (7.141 g, 60 mmol) in water was vigorously stirred and cooled in an ice-water bath. The pH of NaOCl (commercial grade bleach, 600 mL, 806 mmol) was adjusted to 9.5 by dissolving $NaHCO_3$ (8.632 g, 102.75 mmol) immediately before use. This NaOCl solution was added over 40 min while keeping the internal temperature of the reaction mixture between 0° C. and 5° C. After 2 h, the greenish-yellow organic phase was separated and aqueous phase was saturated with NaCl and extracted with $CH_2Cl_2$ (4×100 mL). The combined organic phases was washed with 10% HCl aq. (1×300 mL) containing KI (12 g) and 10% aq. $Na_2CO_3$ (2×150 mL). The organic layer dried ($Na_2SO_4$), filtered and concentrated to give intermediate 12 as a pale yellow liquid (15.79 g, 67%) which was used without purification. $^1$H NMR (500 MHz, $CDCl_3$) δ: 4.24 (2H, t, J=7.3 Hz), 3.86 (2H, s), 2.49 (2H, t, J=7.3 Hz).

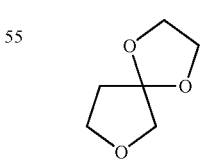

Intermediate 13

1,4,7-Trioxaspiro[4.4]nonane. A mixture of intermediate 12 (15.79 g, 183.5 mmol), ethylene glycol (16.7 mL, 300 mmol) and cat. $TsOH.H_2O$ (100 mg) in benzene (100 mL) was heated at reflux using Dean-Stark trap. After 17 h, the reaction mixture was cooled, diluted with ether (150 mL), washed with sat. $Na_2CO_3$ and brine (50 mL each), dried (Na₂SO₄), filtered and concentrated to give yellow liquid. Distillation under reduced pressure afforded intermediate 13 as a yellow liquid (19.13 g, 80%). ¹H NMR (500 MHz, CDCl₃) δ: 3.9.4 (2H, t, J=7.0 Hz), 3.94-3.90 (4H, m), 3.68 (2H, s), 2.09 (2H, t, J=7.0 Hz).

Intermediate 14

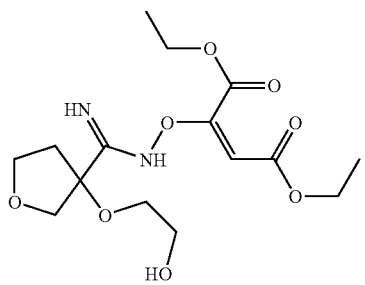

(E)-2-{[3-(2-Hydroxy-ethoxy)tetrahydrofuran-3-carboximidoyl]-aminooxy}but-2-enedioic acid diethyl ester. Prepared according to the procedure for intermediate 8. Yield: 38%; viscous yellow paste. 1H NMR (500 MHz, CDCl₃) δ: 5.78 (1H, d, J=7.6 Hz), 5.59 (1H, br s), 5.38 (1H, s), 4.37-4.27 (2H, m), 4.20-4.13 (2H, m), 4.03-3.87 (4H, m), 3.79-3.75 (2H, m), 3.53-3.45 (2H, m), 1.60 (1H, br s), 1.38-1.23 (6H, m). HRMS (M+H) calcd for $C_{15}H_{25}N_2O_8$: 361.1611; found: 361.1620.

Intermediate 15

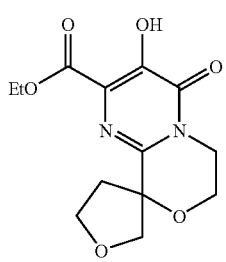

Prepared according to the procedure for intermediate 11. Yield: 29%; brown solid. ¹H NMR (500 MHz, CDCl₃) δ: 10.63 (1H, br s), 4.44 (2H, q, J=7.0 Hz), 4.18-4.11 (4H, m), 4.08-4.01 (4H, m), 2.66-2.60 (1H, m), 2.35-2.30 (1H, m), 1.41 (3H, t, J=7.0 Hz). HRMS (M+H) calcd for $C_{13}H_{17}N_2O_6$: 297.1087; found: 297.1071.

Intermediate 16

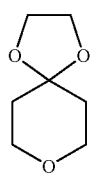

1,4,8-Trioxa-spiro[4.5]decane. A mixture of tetrahydro-4-pyranone (10 g, 99.9 mmol), ethylene glycol (20 mL, 150 mmol) and catalytic toluene sulfonic acid was refluxed in benzene (120 mL) for 5 h. After cooling to room temp, the benzene layer was decanted from the dark oil in the bottom of the flask and was concentrated. The resulting oil was taken up in methylene chloride and shaken in a separatory funnel. The CH₂Cl₂ layer was decanted from the insoluble oil. The CH₂Cl₂ layer was concentrated to give the intermediate 16 as a pale yellow oil (11.62 g, 81% yield). ¹H-NMR (300 MHz, CDCl₃) δ: 3.91 (4H, s), 3.71 (4H, t, J=5.5 Hz), 1.68 (4H, t, J=5.7 Hz).

Intermediate 17

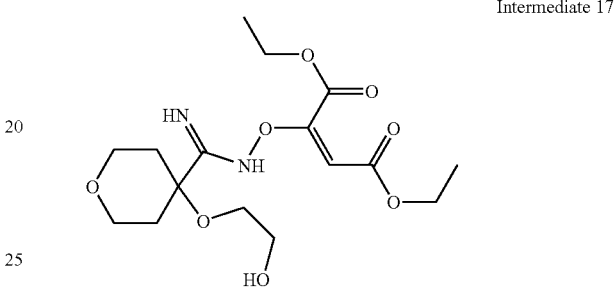

(E)-2-{[4-(2-Hydroxyethoxy)tetrahydropyran-4-carboximidoyl]-aminooxy}but-2-enedioic acid diethyl ester. Prepared according to the procedure for intermediate 8. Yield: 60%; yellow oil. ¹H-NMR (300 MHz, CDCl₃) δ: 5.72 (1H, d, J=22.7 Hz), 5.50 (1H, bs), 5.29 (1H, bs), 4.33-4.23 (2H, m), 4.19-4.04 (2H, m), 3.95-3.87 (1H, m), 3.79-3.63 (6H, m), 3.43-3.39 (2H, m), 2.15-1.74 (4H, m), 1.35-1.19 (6H, m). LCMS [M+H]+calcd for $C_{16}H_{27}N_2O_8$: 375.17; found: 375.19.

Intermediate 18

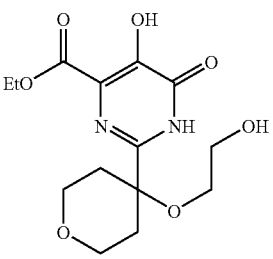

5-Hydroxy-2-[4-(2-hydroxyethoxy)tetrahydropyran-4-yl]-6-oxo-1,6-dihydropyrimidine-4-carboxylic acid ethyl ester. A solution of an intermediate 17 (9.3 g, 25 mmol) in xylenes (150 mL) was refluxed for 18 h. After cooling to room temp, the mixture was shaken with 0.2 M Na₂CO₃. The aqueous phase was washed with EtOAc, made acidic with conc'd HCl and extracted with CH₂Cl₂. The organic phase was dried (Na₂SO₄) and concentrated. The resulting residue was triturated with ether to give the intermediate 18 as a brown solid (0.87 g, 10% yield) and impure product (2.36 g). LCMS [M+H]+ calcd for $C_{14}H_{21}N_2O_7$: 329.13; found: 329.15.

Intermediate 19

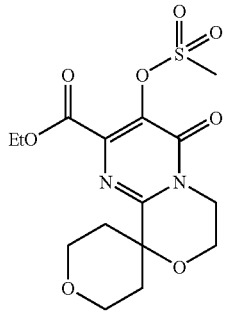

A solution of intermediate 18 (0.86 g, 2.6 mmol) in THF (10 mL) was cooled to 0° C. Added to this was methanesulfonyl chloride (0.613 mL, 7.9 mmol) followed by slow addition of triethylamine (1.07 mL, 7.9 mmol). The mixture stirred for 4 h while gradually warming to room temp. before diluting with EtOAc. The mixture was washed with water and brine and dried ($Na_2SO_4$) before concentrating to give a dark oil. This was dissolved in EtOH (20 mL) and THF (10 mL) and added potassium carbonate (0.56 g, 4.04 mmol). The mixture was stirred at room temp for 18 h, diluted with EtOAc (200 mL) and the solids were removed by filtration. The solution was concentrated and the residue was triturated with methanol. Filtration gave the intermediate 19 as a white solid (0.23 g, 23%). $^1$H-NMR (300 MHz, $CDCl_3$) δ: 4.41 (2H, q, J=7.2 Hz), 4.03-3.98 (4H, m), 3.88-3.82 (2H, m), 3.74 (2H, t, J=11.2 Hz), 3.50 (3H, s), 2.44 (2H, dt, J=13.1, 4.9 Hz), 1.76 (2H, d, J=13.9 Hz), 1.38 (3H, t, J=7.1 Hz). LCMS [M+H]+ calcd for $C_{15}H_{21}N_2O_8S_3$: 389.10; found: 389.13.

Intermediate 20

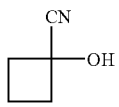

1-Hydroxycyclobutanecarbonitrile. To a flask containing cyclobutanone (13.41 g, 191 mmol) was added a solution of potassium phosphate monobasic (29.10 g, 214 mmol) in water (50 mL), followed by a solution of sodium cyanide (10.39 g, 210 mmol) in water (50 mL), and the reaction was stirred for 16 hours. The reaction was treated with diethyl ether (100 mL) and stirred for 30 minutes. The separated aqueous layer was washed with ether (2×100 mL), and the combined extracts were concentrated to an oil. The oil was dissolved in dichloromethane, dried (sodium sulfate), filtered, and concentrated to give an amber oil (15.10 g), which contained approximately 15% of intermediate 20. The intermediate was used without further purification or treatment. $^1$H NMR (500 MHz, $CDCl_3$) δ: 3.15 (1H, br s), 2.60-2.68 (2H, m), 2.29-2.38 (2H, m), 1.89-2.03 (2H, m).

Intermediate 21

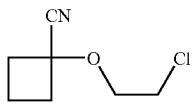

1-(2-Chloroethoxy)cyclobutanecarbonitrile. Zinc chloride (36.03 g, 264 mmol) was fused using a propane torch while under vacuum. The molten zinc was cooled and the evacuated flask was flushed with nitrogen. The flask was loaded with intermediate 2 (15.10 g,) and 2-chloroethanol (17.7 g, 218 mmol) and stirred with heating (90° C.) for 20 hours. The reaction mixture was diluted with water (200 mL) and extracted with ethyl acetate (1×150 mL, 4×100 mL). The combined organic layers were dried (sodium sulfate), filtered, and concentrated to an oil in-vacuo. The crude product was purified by vacuum distillation (b.p.$_{12}$ 85° C.) to give intermediate 21 (5.00 g, 31.3 mmol, 16.4% over two steps) as a clear liquid. $^1$H NMR (500 MHz, $CDCl_3$) δ: 3.75 (2H, t, J=5.5 Hz), 3.65 (2H, t, J=5.6 Hz), 2.52-2.61 (2H, m), 2.31-2.43 (2H, m), 1.91-2.06 (2H, m).

Intermediate 22

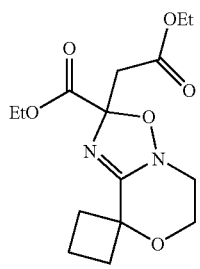

A solution of intermediate 21 (2.64 g, 16.5 mmol) in ethanol (10 mL) was treated with a 50 weight-percent aqueous. solution of hydroxylamine (3.34 g, 50 mmol), and stirred with heating (60° C.) for 16 hours. The solvent was removed in vacuo, and the residue was dried from ethanol-water (1:1, 10 mL) twice, to give as an oily solid. This was used immediately in the following step.

A cold (0° C.) solution of the above oily solid in ethanol (5 mL) and water (10 mL) was treated with a solution of diethyl acetylenedicarboxylate (4.22 g, 25 mmol) in ethanol (50 mL). The reaction was stirred for 5 minutes, then warmed to room temperature, and stirred for 2 hours. The reaction was diluted with water (50 mL) and extracted with ethyl acetate (3×50 mL). The combined extracts were dried (sodium sulfate), filtered, and concentrated in vacuo. The crude was partially purified by flash silica gel column chromatography, eluting with 10% to 35% ethyl acetate in hexanes. Product fractions were pooled and concentrated in vacuo to give intermediate 22 (2.58 g, 48%) as a yellow oil, which was used immediately in the following step. LC/MS [M+H]+=327.14.

Intermediate 23

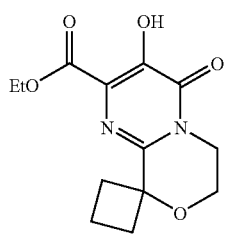

A solution of intermediate 22 (2.51 g, 7.7 mmol) in 1,2,4-trimethyl benzene (25 mL) was heated at reflux (180° C.) for 3 hours, then cooled to room temperature. The solvent was removed in vacuo, and the crude was dissolved in ethyl acetate (75 mL) and extracted with a saturated aqueous solution of sodium bicarbonate (4×75 mL). The combined extracts were brought to pH 1-2 using 6N hydrochloric acid, and the resultant solid was extracted with ethyl acetate (4×50 mL). The combined extract was dried (sodium sulfate), filtered, and concentrated in vacuo to give intermediate 23 (0.235 g, 5.2% over two steps) as a brown solid. $^1$H NMR (500 MHz, CDCl$_3$) δ: 10.54 (1H, s), 4.46 (2H, q, J=7.1 Hz), 3.95-4.00 (4H, m), 2.67-2.74 (2H, m), 2.30 (2H, ddd, J=12.4, 9.9, 7.3 Hz), 2.09-2.19 (1H, m), 1.97-2.06 (1H, m), 1.44 (3H, t, J=7.2 Hz). LC/MS [M+H]$^+$=281.11.

Alternative preparation of intermediate 23 from cyclobutanone.

Intermediate 24

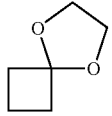

5,8-Dioxa-spiro[3.4]octane. A solution of cyclobutanone (7.7 g, 0.11 mol), ethylene glycol (6.82 g, 0.11 mol) and p-toluenesulfonic acid mono hydrate (200 mg, 1 mmol) in benzene (200 mL) was heated at reflux with a Dean-Stark trap for 14 hrs. After cooling, the mixture was washed with aqueous sodium bicarbonate solution (saturated, 15 mL), then with brine and dried (magnesium sulfate), filtered and concentrated to obtain 9.37 g (82%) of intermediate 24 as a colorless liquid: $^1$H NMR (CDCl$_3$, 500 MHz) δppm 3.87 (4H, s, CH$_2$), 2.31 (4H, t, J=8 Hz, CH$_2$), 1.67 (2H, qt, J=8 Hz, CH$_2$); $^{13}$C NMR (CDCl$_3$, 125.77 Hz) δ: 109.08 (C), 63.87 (CH$_2$), 35.58 (CH$_2$), 11.42 (CH$_2$).

Intermediate 25

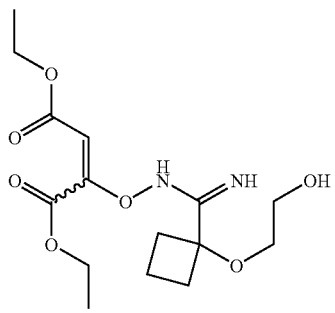

2-{[1-(2-hydroxyethoxy)cyclobutanecarboximidoyl]-aminooxy}but-2-enedioic acid diethyl ester. To a mixture of intermediate 24 (5.70 g, 50 mmol) and trimethylsilyl cyanide (5.05 g, 50 mmol) was added a catalytic amount of ZnI$_2$ (12 mg) in a cool water bath of ~10° C. and the mixture stirred at room temperature for 5 hrs to obtain 10.7 g of 1-(2-trimethylsilanyloxyethoxy)cyclobutanecarbonitrile as a mobile oil: $^1$H NMR (CDCl$_3$, 500 MHz) δ: 3.75 (2H, t, J=5 Hz, OCH$_2$), 3.55 (2H, t, J=5 Hz, OCH$_2$), 2.51-2.56 (2H, m, CH$_2$), 2.30-2.37 (2H, m, CH$_2$), 1.91-1.98 (2H, m, CH$_2$), 0.124 (9H, s, SiCH$_3$); $^{13}$C NMR (CDCl$_3$, 125.77 Hz) δppm 120.43 (CN), 72.05 (C), 67.71 (CH$_2$), 61.49 (CH$_2$), 34.02 (CH$_2$), 12.91 (CH$_2$), −0.29 (CH$_3$). LC/MS m/z 142 (M+H—SiMe$_3$).

A solution of 1-(2-trimethylsilanyloxyethoxy)cyclobutanecarbonitrile (3.5 g, 16.4 mmol) and 50% aqueous hydroxylamine (1.08 g, 16.4 mmol) in EtOH (16 mL) was stirred in an oil bath heated at 80° C. for 2.5 hrs and then cooled to room temperature. To a solution was added drop-wise diethyl acetylenedicarboxylate (2.93 g, 17.2 mmol) in an ice-bath and the mixture stirred at room temperature for 5 hrs. This mixture was concentrated in vacuo to obtain 6.16 g of a crude brownish oil containing intermediate 25: $^1$H NMR (500 MHz, CDCl$_3$) δ: 1.19-1.38 (6 H, m) 1.72-1.86 (2 H, m) 2.06-2.24 (2 H, m) 2.29-2.49 (2 H, m) 3.26-3.38 (2 H, m) 3.65-3.76 (2H, m) 4.11-4.19(2 H, m) 4.24-4.38(2 H, m) 5.67(0.25 H, s) 5.85 (0.5 H, s). HRMS (M+H) calcd for C$_{15}$H$_{25}$N$_2$O$_7$ 345.1662, found 345.1648.

Intermediate 26

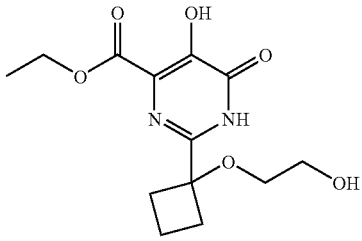

5-hydroxy-2-[-1-(2-hydroxy-ethoxy)-cyclobutyl]-6-oxo-1,6-dihydro-pyrimidine-4-carboxylic acid ethyl ester. A solution of a crude intermediate 25 (5.9 g) in xylenes (30 mL) was heated at 150-155° C. for 20 h. The mixture was concentrated in vacuo and the residue re-dissolved in EtOAc (30 mL) was extracted with 1M aq. sodium carbonate solution (3×20 mL). The aqueous extracts were acidified with careful addition of concentrated HCl, and this mixture was extracted with CH$_2$Cl$_2$ (2×20 ml). The combined organic extracts were dried (Na$_2$SO$_4$), filtered and concentrated to obtain intermediate 26 (1.19 g, 24% over three steps) as brownish oil: LC/MS m/z 299 (M+H).

Intermediate 27

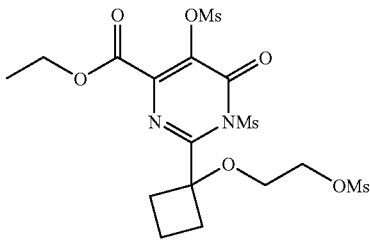

Ethyl 1-(methylsulfonyl)-5-(methylsulfonyloxy)-2-(1-(2-(methylsulfonyloxy)ethoxy)cyclobutyl)-6-oxo-1,6-dihydro-pyrimidine-4-carboxylate (27): A cold (0° C.) solution of intermediate 26 (7.23 g, 25 mmol) in anhydrous tetrahydrofuran was treated with methanesulfonylchloride (Aldrich) by dropwise addition. The solution was warmed to room temperature and stirred for 4 hrs. The reaction was concentrated in-vacuo, and the crude product was dissolved in ethyl acetate (75 mL) and washed with saturated sodium bicarbonate solution. The organic solution was dried (sodium sulfate), filtered to remove solids, and concentrated in vacuo to give intermediate 27 as a brown oil. This was used in the subsequent reaction without further purification. $^1$H NMR (500 MHz, CDCl$_3$) δ: 4.49 (2H, q, J=7.0 Hz), 4.35-4.38 (2H, m), 3.93-4.00 (1H, m), 3.66-3.67 (3H, s), 3.62-3.65 (2H, m), 3.44-3.46 (3H, m), 3.05-3.07 (3H, s), 2.74-2.82 (1H, m), 2.60-2.67 (2H, m), 2.41-2.49 (2H, m), 1.43 (3H, t, J=7.0 Hz). LCMS (M+H): 532.94.

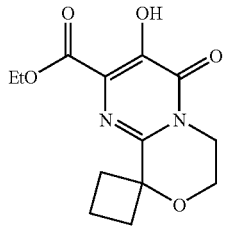

Intermediate 28

To a solution of intermediate 27 obtained above in absolute ethanol (50 mL) and anhydrous tetrahydrofuran (75 mL) was added anhydrous potassium carbonate (3.46 g, 25 mmol), and the reaction was stirred with heating (65° C.) for 20 hrs. Solvent was removed in-vacuo and the crude product was dissolved in water (150 mL) and extracted with ethyl acetate (2×100 mL). The aqueous layer was made acidic (pH 1-2) using 6.0 N hydrochloric acid, and the resulting solid was extracted with ethyl acetate (2×75 mL). The combined extract was dried (sodium sulfate), filtered to remove solids, and concentrated to give intermediate 28 (4.30 g, 61%) as a light brown solid. $^1$H NMR (500 MHz, CDCl$_3$) δ: 10.57 (1H, s), 4.46 (2H, q, J=7.2 Hz), 3.97 (4H, s), 2.67-2.73 (2H, m), 2.27-2.33 (2H, m), 2.10-2.18 (1H, m), 1.98-2.06 (1H, m), 1.44 (3H, t, J=7.2 Hz). $^{13}$C NMR (126 MHz, CDCl$_3$) δ: 169.56, 157.68, 150.41, 148.19, 125.24, 79.09, 62.63, 58.52, 42.66, 34.72, 14.18, 13.87; LC/MS (M+H): 281.13.

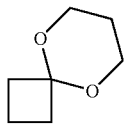

Intermediate 29

Intermediate 29 was prepared (50% yield) according to the procedure for intermediate 24. $^1$H NMR (500 MHz, C$_6$D$_6$) δ: 3.49 (4H, t, J=5.5 Hz), 2.23 (4H, t, J=8 Hz), 1.63 (2H, qt, J=8 Hz), 1.24 (2H, qt, J=5.5 Hz).

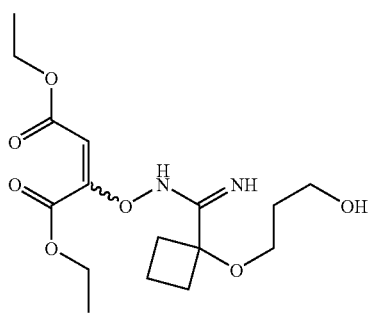

Intermediate 30

Intermediate 30 was prepared (52% yield) according to the procedure for intermediate 25. $^1$H NMR (500 MHz, C$_6$D$_6$) δ: 3.54 (2H, t, J=6.1 Hz), 3.45 (2H, t, J=6.1 Hz), 2.06-2.12 (2H, m), 1.87 (2H, dq, J=9.7, 2.6 Hz), 1.68 (2H, qt, J=6.1 Hz), 1.43-1.51 (1H, m), 1.26-1.34 (1H, m), 0.10 (9H, s). LC/MS [M+H]$^+$=359.20

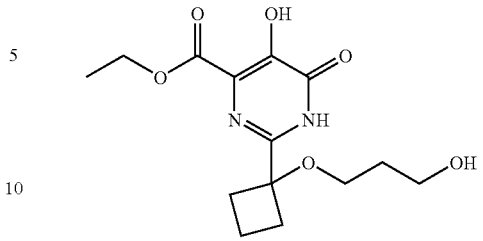

Intermediate 31

Intermediate 31 was prepared (69% yield) according to the procedure for intermediate 26. $^1$H NMR (500 MHz, CDCl$_3$) δ: 4.46 (2H, q, J=7.0 Hz), 3.84 (2H, t, J=5.5 Hz), 3.41 (2H, t, J=5.5 Hz), 2.51-2.58 (2H, m), 2.29-2.38 (2H, m), 1.89-1.99 (2H, m), 1.82-1.90 (3H, m), 1.45-(3H, t, J=7.0 Hz), 1.31-1.41 (1H, m). LC/MS (ESI) [M+H]$^+$=313.05.

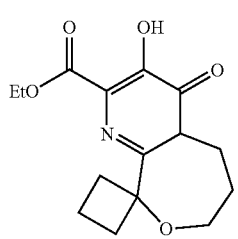

Intermediate 32

A cold (0° C.) solution of intermediate 31 (3.0 g, 9.6 mmol) in tetrahydrofuran (25 mL) was treated with methanesulfony chloride (3.30 g, 29 mmol) followed by dropwise addition of triethylamine (4.7 mL, 33.6 mmol). The reaction was stirred for 16 hours at room temperature. The solvent was removed in vacuo and the mixture was dissolved in ethanol (50 mL) and dimethylformamide (25 mL). To the slurry was added potassium carbonate (1.36 g, 9.7 mmol) and the reaction was stirred at room temperature for 16 hours, followed by heating (80° C.) for 3 hours. The solvent was removed in vacuo. The crude product was diluted with ethyl acetate (50 mL) and washed with 1N hydrochloric acid (2×50 mL), extracted with ethyl acetate (2×25 mL) then brine ((50 mL). The solution was then dried (sodium sulfate), filtered and concentrated to give intermediate 32 (0.534 g, 19%) as a brown solid. $^1$H NMR (500 MHz, CDCl$_3$) δ: 10.64 (1H, br s), 4.45 (2H, q, J=7.0 Hz), 4.38 (2H, br), 3.91 (2H, t, J=5.0 Hz), 2.81 (2H, br), 2.36-2.44 (2H, m), 1.87-1.97 (1H, m), 1.82-1.86 (2H, m), 1.67-1.75 (1H, m), 1.43 (3H, t, J=7.2 Hz).

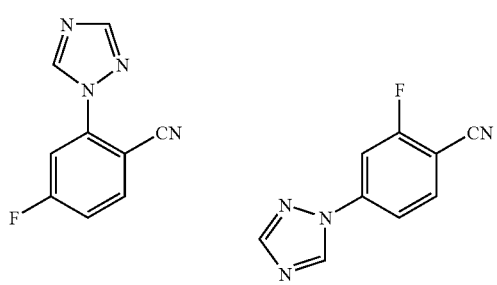

Intermediates 33 and 34

4-Fluoro-2-(1H-1,2,4-triazol-1-yl)benzonitrile (33) and 4-(1H-1,2,4-triazol-1-yl)-2-fluorobenzonitrile. To a solution of 2,4-difluorobenzonitrile (10 g, 72 mmol) dissolved in THF (20 mL), and DMF (40 mL) was added 1,2,4-triazole sodium derivative (6.3 g, 70 mmol) and the mixture was stirred at 90° C. for 3 h, filtered and concentrated. The residue was adsorbed onto Silica gel and purified by flash chromatography eluting with 0%-10%-30% EtOAc/hexanes to give intermediate 33 as colorless needles (2.46 g, 18%) and intermediate 34 was obtained as a white solid (0.7455 g, 6%).

Intermediate 33: $^1$H NMR (500 MHz, CDCl$_3$) δ: 8.89 (1H, s), 8.19 (1H, s), 7.85 (1H, dd, J=8.7, 5.6 Hz), 7.60 (1H, dd, J=8.8, 2.4 Hz), 7.28-7.24 (1H, m). LCMS (M+H) calcd for C$_9$H$_6$N$_4$F: 189.05; found: 189.13.

Intermediate 34: $^1$H NMR (500 MHz, CDCl$_3$) δ: 8.66 (1H, s), 8.15 (1H, s), 7.79 (1H, dd, J=8.5, 6.7 Hz), 7.69 (1H, dd, J=9.5, 1.8 Hz), 7.65-7.63 (1H, m). LCMS (M+H) calcd for C$_9$H$_6$N$_4$F: 189.05; found: 189.13.

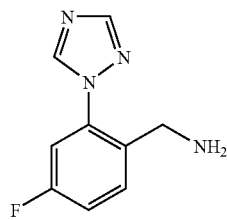

Intermediate 35

(4-Fluoro-2-(1H-1,2,4-triazol-1-yl)phenyl)methanamine hydrochloride. Nitrile 33 (2.46 g, 13.13 mmol) was dissolved in hot ethanol (150 mL). Aqueous HCl (15 mL, 1N) was added followed by 10% Pd/C (200 mg). The mixture was shaken under H$_2$ at 55 psi for 4 h., filtered over celite and concentrated. The residue was partitioned between EtOAc and water. The aqueous phase was lyophilized to give intermediate 35 as a white powder (2.96 g, 99%). $^1$H NMR (500 MHz, CD$_3$OD) δ: 9.51 (1H, s), 8.63 (1H, s), 7.85 (1H, dd, J=8.5, 5.8 Hz), 7.68 (1H, dd, J=8.8, 2.4 Hz), 7.49 (1H, td, J=8.3, 2.4 Hz), 4.20 (2H, s). LCMS (M+H) calcd for C$_9$H$_{10}$N$_4$F: 193.08; found: 193.16.

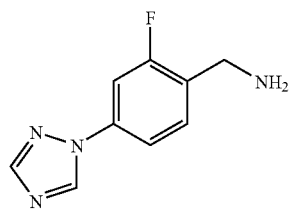

Intermediate 36

(4-Fluoro-2-(1H-1,2,4-triazol-1-yl)phenyl)methanamine hydrochloride. Intermediate 36 was prepared (79% yield) following the procedure for intermediate 35 using intermediate 34. $^1$H NMR (500 MHz, CD$_3$OD) δ: 9.25 (1 H, s), 8.46 (1H, s), 7.80 (1H, dd, J=8.6, 5.8 Hz), 7.64 (1H, dd, J=8.8, 2.4 Hz), 7.44 (1H, td, J=8.3, 2.6 Hz), 4.17 (2H, s). LCMS (M+H) calcd for C$_9$H$_{10}$N$_4$F: 193.08; found: 193.16.

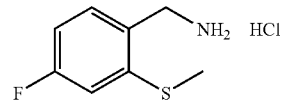

Intermediate 37

4-Fluoro-2-methylsulfanyl-benzylamine. 4-Fluoro-2-(methylthio)benzonitrile (prepared as in Anthony, N. J. et al. PCT Appl. WO 02/30931, 2002) (1.67 g, 0.1 mol) was dissolved in 20 mL THF and under N$_2$ treated with 10 mL 2M BH$_3$.Me$_2$S. This was heated at 60° C. for 2 hrs. Heating was discontinued and 5 mL MeOH was cautiously added, followed by the cautious addition of 4 mL 6N HCl. Then 20 mL more H$_2$O added and EtOAc and the layers were separated. The aqueous layer was made basic with 1N NaOH and extracted with CH$_2$Cl$_2$. The extracts were dried (MgSO$_4$), filtered, concentrated and dried in vacuum to give intermediate 37 (1.3 g, 76%) as a solid. $^1$H NMR (500 MHz, CDCl$_3$) δ: 7.20-7.31 (1 H, m) 6.90 (1 H, dd, J=2.4 Hz) 6.75-6.86 (1 H, m) 3.86 (2 H, s) 2.47 (3 H, s). LC/MS (M+H): 172.

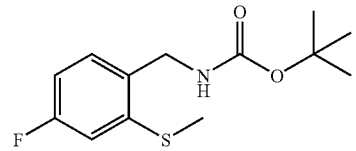

Intermediate 38

N-t-Butoxycarbonyl-(4-fluoro-2-(methylthio)phenyl) methanamine. A stirred solution of intermediate 37 (5.1 g, 0.03 mol) and 3.3 g triethylamine in 100 mL CH$_2$Cl$_2$ under N2 was treated with di-t-butyl dicarbonate (7.2 g, 0.033 mol) portionwise and stirred at room temperature for 30 min. Then, the reaction mixture was washed with dil HCl and water. The organic layer was dried over MgSO$_4$, filtered and concentrated to leave 8.1 g (100%) of intermediate 38 as a clear oil. $^1$H NMR (500 MHz, CDCl$_3$) δ: 7.22-7.29 (1 H, m) 6.89 (1 H, dd, J=9.61, 2.29 Hz) 6.75-6.83 (1H, m) 4.93 (1 H, s) 4.31 (2 H, d, J=5.49 Hz) 2.47 (3 H, s) 1.44 (9 H, s). LC/MS (M+H): 272.

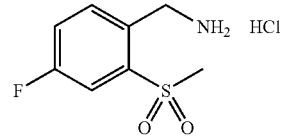

Intermediate 39

(4-Fluoro-2-(methylsulfonyl)phenyl)methanamine hydrochloride. A solution of intermediate 38 (8.1 g, 0.03 mol) in 100 mL acetone and 50 mL water was treated with oxone (18.5 g, 0.03 mol) and stirred for 10 min. Then an additional 18.5 g oxone was added and the mixture was warmed at 60° C. for 1.5 hrs. This was cooled, concentrated to remove acetone and extracted with CH$_2$Cl$_2$. This was concentrated to an oil, dissolved in 20 mL ethanol and treated with 10 mL 6N HCl and warmed at 60° C. for 2 h. Removal of solvents gave a gum which was crystallized from ethanol to give intermediate 39 (2.0 g) as crystals. The aqueous layer was made basic with ammonium hydroxide and extracted further with $CH_2Cl_2$ and concentration of the extracts gave a gum which was treated with HCl in ethanol to give an additional 0.9 g of intermediate 39. $^1$H NMR (500 MHz, DMSO-$D_6$) δ: 8.54 (3 H, s) 7.89 (1 H, dd, J=8.54, 5.19 Hz) 7.67-7.85 (2 H, m) 4.40 (2 H, s) 3.41 (3 H, s). LC/MS (M+H)=204.

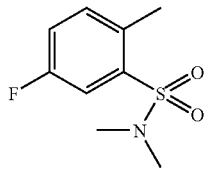

Intermediate 40

5-Fluoro-2,N,N-trimethyl-benzenesulfonamide. To a solution of 5-fluoro-2-methyl-benzenesulfonyl chloride (4.18 g, 20 mmol) in THF (25 mL) was added drop-wise in 15 min a solution of dimethylamine in THF (2M, 25 mL, 50 mmol) under nitrogen and the mixture stirred for 5 min. The insoluble materials formed were filtered and the filtrate concentrated. The residue was purified by column chromatography ($SiO_2$, 5% $Et_2O$ in $CH_2Cl_2$) to obtain intermediate 40 (4.3 g, 90%) as a clear oil. $^1$HNMR (500 MHz, CDCl$_3$) δ: 2.57 (3 H, s) 2.82 (3 H, s) 2.82 (3 H, s) 7.12-7.18 (1 H, m) 7.28 (1 H, dd, J=8.2, 5.5 Hz) 7.59 (1 H, dd, J=8.2, 2.1 Hz). LC/MC (M+H): 218.

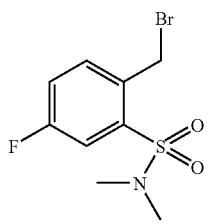

Intermediate 41

2-Bromomethyl-5-fluoro-N,N-dimethyl-benzenesulfonamide. A mixture of intermediate 40 (435 mg, 2.0 mmol) and N-bromosuccinimide (391 mg, 2.2 mmol) in $CCl_4$ (20 mL) was stirred in an oil bath heated at 80-90° C. under nitrogen for 5 min. To this mixture was added 2,2'-azobisisobutyronitrile (AIBN,100 mg) and the mixture continued to heat at 80-90° C. for 30 min. After cooling, the insoluble precipitates were filtered and the filtrate concentrated and purified by column chromatography ($SiO_2$, $CH_2Cl_2$) to obtain intermediate 41 (440 mg, 74%). $^1$HNMR (500 MHz, CDCl$_3$) δ: 2.87 (6 H, s) 4.86 (2 H, s) 7.28 (1 H, dd, J=8.55, 2.75 Hz) 7.61-7.65 (2 H, m). LC/MC (M+H): 296/298.

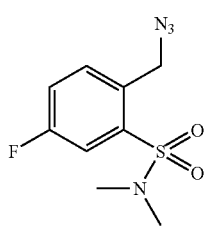

Intermediate 42

2-Azidomethyl-5-fluoro-N,N-dimethyl-benzenesulfonamide. A mixture of intermediate 41 (880 mg, 2.97 mmol) and sodium azide (200 mg, 3 mmol) in DMF (4 mL) was stirred under nitrogen in an oil bath heated at 55-60° C. for 30 min and the solvent was removed in vacuo. The residue was partitioned between $CH_2Cl_2$ and water, and the organic phase was washed with water, dried ($Na_2SO_4$), filtered and concentrated to obtain intermediate 42 (670 mg, 87%) of as a yellow oil. $^1$HNMR (500 MHz, CDCl$_3$) δ: 2.84 (6 H, s) 4.78 (2 H, s) 7.29-7.34 (1 H, m) 7.59-7.64 (2 H, m).

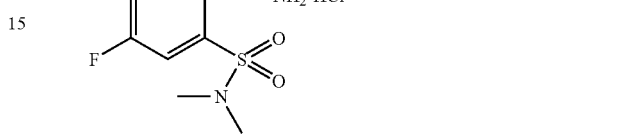

Intermediate 43

2-(aminomethyl)-5-fluoro-N,N-dimethylbenzenesulfonamide hydrochloride. To a solution of intermediate 42 (660 mg, 2.6 mmol) in THF (10 mL) and water (2 mL) was added triphenylphosphine (740 mg, 2.8 mmol), and the mixture stirred under nitrogen for 1 h. The THF was evaporated in vacuo and a mixture of the residue and 6N HCl (3 mL) in MeOH (5 mL) was heated in an oil bath at 80° C. for 20 h. This was washed with $CH_2Cl_2$, and the aqueous phase basified with dilute $NH_4OH$ and extracted with $CH_2Cl_2$. The organic extract was dried ($Na_2SO_4$), filtered and concentrated to obtain free amine 43 (210 mg, 35%) as an oil. $^1$H NMR (500 MHz, CDCl$_3$) δ: 2.84 (6 H, s) 4.10 (2 H, s) 7.23-7.29 (1 H, m) 7.53-7.60 (2 H, m); LC/MS (M+H): 233.

Alternatively, a solution of intermediate 42 (23.6 g, 91.37 mmOl) in EtOH (100 mL) and 5M aq. HCl (22 mL) was degassed by bubbling N2 through it for 5 min. and 10%Pd/carbon (2.0 g) was added. This mixture was evacuated and vented to $H_2$ (repeated three times) and left on Parr shaker for 20 h under H2 (40 psi) atmosphere. The reaction mixture was filtered, concentrated and resulting residue was taken up in water (200 mL). This was extracted with EtOAc (3×50 mL). The organic layer discarded and aqueous layer freeze dried to afford 43 (16.3 g, 66%) as pale yellow powder.

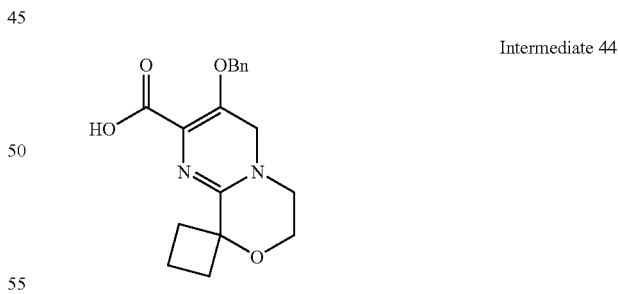

Intermediate 44

To a solution of intermediate 28 (0.103 g, 0.367 mmol) in anhydrous dimethylformamide (4 mL) was added anhydrous potassium carbonate (0.206 g, 1.47 mmol) and benzyl bromide (0.071 g, 0.39 mmol), and the reaction was stirred with heating (60° C.) for 18 hours under nitrogen atmosphere. To the reaction mixture was added lithium hydroxide (0.024 g, 0.92 mmol), water (5 mL) and ethanol (5 mL). The reaction was stirred (60° C.) for 2 hours, after which HPLC indicated reaction was complete. The solvent was removed in vacuo, and the crude product was dissolved in water (~10 mL) and brought to pH 1-2 using 6 N hydrochloric acid. The product was extracted with ethyl acetate (3×30 mL), dried (Na$_2$SO$_4$), filtered and concentrated to give 0.13 g (100%) of intermediate 44 as an oil which solidified upon standing. The intermediate was used in the following reaction without further purification: $^1$H NMR (500 MHz, CDCl$_3$) δ: 7.54 (2H, d, J=7.3 Hz), 7.30-7.38 (3H, m), 5.49 (2H, s), 3.95-4.01 (4H, m), 2.67-2.74 (2H, m), 2.33-2.41 (2H, m), 2.06-2.14 (2H, m).

Intermediate 45

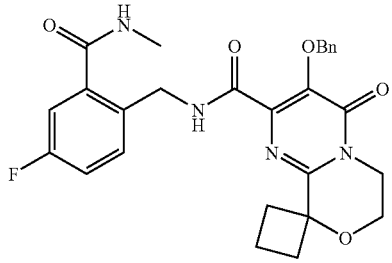

To a solution of intermediate 44 (obtained above) in dimethylformamide (3 mL) was added O-(7-azabenzotriazol-1-yl)-N,N,N',N'-tetramethyluronium hexafluorophosphate (HATU, 0.167 g, 0.44 mmol) and the mixture was stirred for 20 minutes. To this was added 2-(aminomethyl)-5-fluoro-N-methylbenzamide hydrochloride (prepared according to M. Egbertson et al PCT Appl. WO 03077850) and N,N-dimethylaminopyridine (0.068 g, 0.55 mmol) and the reaction was stirred for 16 hours. The solvent was removed in vacuo and the crude product in ethyl acetate (25 mL) was washed with 1.0 N hydrochloric acid (25 mL), then dried (Na$_2$SO$_4$), filtered, and concentrated to give an orange-brown solid. This was purified by flash silica gel column chromatography, eluting with 30% to 60% ethyl acetate in hexanes, to give a colorless oil. The oil was triturated with diethyl ether and dried in-vacuo to give intermediate 45 (0.101 g, 54% over two steps) as a white glassy solid: $^1$H NMR (500 MHz, CDCl$_3$) δ: 8.62 (1H, t, J=6.1 Hz), 7.44-7.51 (3H, m), 7.27-7.33 (3H, m), 7.13 (1H, dd, J=8.9, 2.7 Hz), 7.08 (1 H, dt, J=8.2, 2.7 Hz), 6.49-6.58 (1H, m), 5.28 (2H, s), 4.56 (2H, d, J=6.4 Hz), 3.90-4.00 (4H, m), 2.98 (3H, d, J=4.9 Hz), 2.71-2.79 (2H, m), 2.26-2.36 (2H, m), 2.14-2.24 (1H, m), 2.04-2.11 (1H, m). LC/MS (M+H) 507.13.

Intermediate 46

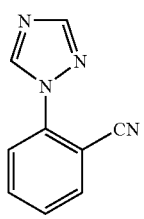

2-(1H-1,2,4-triazol-1-yl)benzonitrile: A suspension of 2-fluorobenzylnitrile (3.0 g, 25 mmol) and 1,2,4-triazole sodium complex (2.4 g, 27 mmol) were stirred in THF (7 mL) and DMF (14 mL) at 95° C. for 18 h. After cooling and concentrating, the product was crystallized from hot CH$_2$Cl$_2$/hexane (1:1) to give the title compound as a white solid (4.25 g, 100% yield). $^1$H-NMR (300 MHz, CDCl$_3$) δ: 8.74 (1H, s), 8.16 (1H, s), 7.82 (1H, dd, J=4.9,1.3 Hz), 7.77-7.25 (2H, m), 7.57-7.51 (1H, m). LCMS [M+H]$^+$ calcd for C$_9$H$_7$N$_4$: 171.06; found: 171.12.

Intermediate 47

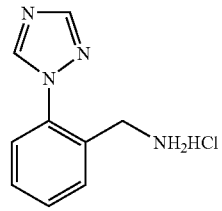

2-(1H-1,2,4-triazol-1-yl)phenyl)methanamine hydrochloride: Intermediate 46 (4.25 g, 25 mmol) was dissolved in EtOH (50 mL) and 1N HCl (25 mL). Added Pd/C (1 g) and mixture was shaken under H$_2$ for 2 h at 50 psi. After filtration over celite and concentration, the residue was triturated with diethyl ether and the title compound was collected as a white solid (3.94 g, 75% yield). $^1$H-NMR (300 MHz, CD$_3$OD) δ: 9.01 (1H, s), 8.32 (1H, s), 7.78-7.64 (4H, m), 4.15 (2H, s). LCMS [M+H]$^+$ calcd for C$_9$H$_{11}$N$_4$: 175.09; found: 175.17.

Intermediate 48

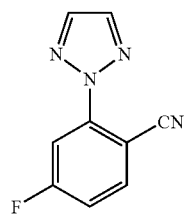

4-Fluoro-2(2H-1,2,3-triazol-2-yl)benzonitrile: To a solution of 1H-1,2,3-triazole (3.5 g, 50.7 mmol) in THF (10 mL) and DMF (20 mL) was added portionwise, NaH (1.3 g, 51 mmol, 95%). The mixture was stirred at room temp for 30 min. Added to this was 2,4-difluorobenzonitrile (7.6 g, 55 mmol) and the mixture was stirred at 85° C. for 3 h. The white mixture was concentrated and purified by flash chromatography eluting with 0%-5%-10% EtOAc/hexane to give the title compound as white needles (0.34 g, 3% yield). $^1$H-NMR (300 MHz, CDCl$_3$) δ: 7.92 (2H, s), 7.88-7.79 (2H, m), 7.19-7.12 (1H, m). LCMS [M+H]$^+$ calcd for C$_9$H$_6$N$_4$F: 189.05; found: 189.12.

Intermediate 49

4-Fluoro-2-(2H-1,2,3-triazol-2-yl)phenyl)methanamine hydrochloride: Intermediate 48 (0.34 g, 1.8 mmol) was dissolved in EtOH (50 mL). Added to this solution was 1N HCl (10 mL) and catalytic Pd/C. The mixture was shaken under H$_2$ at 55 psi for 4 h, filtered over celite and concentrated to give the title compound as a yellow solid (0.4021 g, 98% yield). $^1$H-NMR (500 MHz, CD$_3$OD) δ: 8.13 (2H, s), 7.87 (1H, dd, J=4.9, 2.6 Hz), 7.73 (1H, dd, J=4.9, 2.6 Hz), 7.34 (1H, td, J=8.2, 2.7 Hz), 4.35 (2H, s). LCMS [M+H]$^+$ calcd for C$_9$H$_{10}$N$_4$F: 193.08; found: 193.16.

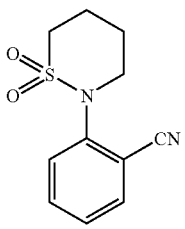

Intermediate 50

2-(1,1-dioxo-1λ6-[1,2]thiazinan-2-yl)benonitrile: Added to a solution of 1,1-dioxo[1,2]thiazinane (3.37 g, 25 mmol) in DMF (35 mL) was sodium hydride (0.675 g, 25 mmol, 95%) and the mixture was stirred at room temp for 15 min. 2-Fluorobenzonitrile (3.37 mL, 31.3 mmol) was added and the mixture was stirred at 80° C. for 18 h. The mixture was cooled, diluted with water and extracted with EtOAc. The organic phase was washed with water and brine, dried (Na$_2$SO$_4$) and concentrated. The residue was purified by flash chromatography eluting with 10%-100% EtOAc/hexane. The isolated solid was recrystalized from hot EtOAc/hexane (2:1) to give the title compound as white crystals (4.15 g, 70% yield). 1H-NMR (300 MHz, CDCl$_3$) δ: 7.70 (1H, dd, J=7.7,1.1 Hz), 7.64-7.53 (2H, m), 7.41 (1H, td, J=7.3, 1.6 Hz), 3.72 (2H, t, J=5.5 Hz), 3.32 (2H, t, J=6.0 Hz), 2.40-2.32 (2H, m), 2.05-1.97 (2H, m). LCMS [M+H]$^+$ calcd for C$_{11}$H$_{12}$N$_2$O$_2$S: 237.06; found: 237.10.

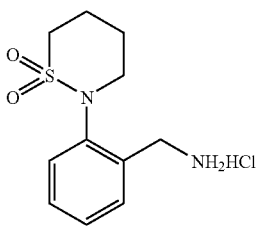

Intermediate 51

2-(1,1-dioxo-1λ6-[1,2]thiazinan-2-yl)benzylamine hydrochloride: Intermediate 50 (2.63 g, 11.14 mmol) was dissolved in EtOH (150 mL) and 1N HCl (13 mL). Added to this was Pd/C (0.5 g) and the mixture was shaken under H$_2$ at 55 psi for 24 h. Filtration over celite and concentration gave the title compound as a white solid (2.93 g, 95% yield). $^1$H-NMR (300 MHz, CD$_3$OD) δ: 7.61-7.47 (4H, m), 4.30 (2H, q, J=13.7 Hz), 3.96-3.87 (1H, m), 3.49-3.36 (3H, m), 2.40-2.31 (2H, m), 2.05-1.96 (2H, m). LCMS [M+H]$^+$ calcd for C$_{11}$H$_{17}$N$_2$SO$_2$: 241.10; found: 241.10.

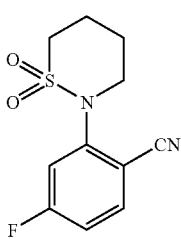

Intermediate 52

4-Fluoro-2-(1,1-dioxo-1 λ6-[1,2]thiazinan-2-yl)benzonitrile: To a solution of 1,1-dioxo[1,2]thiazinane (8.84 g, 65.4 mmol) in DMF (20 mL) and THF (10 mL) was added portionwise sodium hydride (1.65 g, 65.5 mmol, 95%). After stirring for 30 min, 2,4-difluorobenzonitrile (10.0 g, 72 mmol) was added and the mixture was stirred at 90° C. for 2.5 h. The mixture was cooled and concentrated and the residue was purified by flash chromatography eluting with 0%-10% EtOAc/hexane to give the title compound as white needles (1.37 g, 8% yield). $^1$H-NMR (500 MHz, CDCl$_3$) δ: 7.70 (1H, dd, J=8.8, 5.8 Hz), 7.30 (1H, dd, J=8.8, 2.4 Hz), 7.15-7.12 (1H, m), 3.72 (2H, t, J=5.3 Hz), 3.33 (2H, t, J=6.1 Hz), 2.40-2.35 (2H, m), 2.05-2.01 (2H, m). LCMS [M+H]$^+$ calcd for C$_{11}$H$_{12}$N$_2$FO$_2$S: 255.06; found: 255.19.

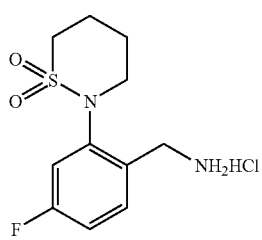

Intermediate 53

4-Fluoro-2-(1,1-dioxo-1λ6-[1,2]thiazinan-2-yl)benzylamine hydrochloride: Following the procedure for Intermediate 51 using Intermediate 52 (1.37 g, 5.4 mmol) gave the title compound as a white solid (1.58 g, 100% yield). $^1$H-NMR (300 MHz, CD$_3$OD) δ: 7.61 (1H, dd, J=8.4, 6.2 Hz), 7.38 (1H, dd, J=9.3, 2.7 Hz), 7.28 (1H, td, J=8.2, 2.7 Hz), 7.26 (2H, dd, J=21.4, 13.7 Hz), 3.93-3.84 (1H, m), 3.50-3.41 (3H, m), 2.40-2.31 (2H, m), 2.04-1.96 (2H, m). LCMS [M+H]$^+$ calcd for C$_{11}$H$_{16}$N$_2$FO$_2$S: 259.09; found: 259.24.

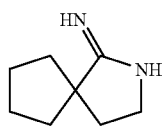

Intermediate 54

To a solution of 1-(2-chloroethyl)cyclopentanecarbonitrile (1.38 g, 8.73 mmol; prepared according to R. M. Burk et al Heterocycles 1993, 35, 205) in 40 mL MeOH was added 1 mmol sodium iodide and the solution was saturated with ammonia. The reaction bottle was sealed and warmed at 90° C. with stirring for 20 h. After cooling the reaction bottle was opened and solvents were evaporated under vacuum. LC/MS (M+H): 139. $^1$H NMR (500 MHz, CDCl$_3$) δ: 1.50-2.33 (10H, m), 3.53-3.78 (2H, m).

Intermediate 55

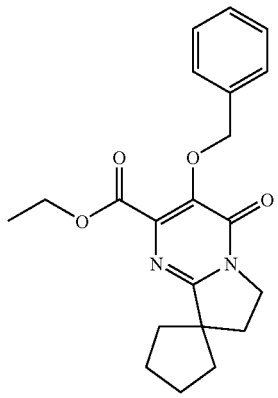

To a solution of diethyl-2-(benzyloxy)-3-hydroxyfumarate [prepared from benzyloxy ethylacetate (2.91 g, 0.015 mol) and diethyloxalate (2.19 g, 0.015 mol) with an equivalent amount of sodium hydride in 40 mL THF and 2 drops EtOH by stirring for 30 min] in 20 mL EtOH was added intermediate 54 in 10 mL EtOH and with stirring 60% NaH (300 mg, 0.0075 mol) was added portionwise. This was stirred for 3 h at rt and concentrated. The residue was dissolved in $CH_2Cl_2$ and washed with water. The CH2Cl2 layer was dried over $MgSO_4$, filtered and concentrated. Chromatography on silica and elution with 9:1 $CH_2Cl_2:Et_2O$ gave 600 mg of the title compound 55 (Yield=19%). LC/MS (M+H): 369. $^1$H NMR (500 MHz, $CDCl_3$) δ: 1.29 (3H, t, J=7.2 Hz), 1.56 (1H, s), 1.68-1.80 (3H, m), 1.85-1.96 (1H, m) 2.04-2.17 (3H, m), 4.03-4.08 (1H, m), 4.03-4.10 (2H, m), 4.22 (1H, q, J=7.0 Hz), 4.32 (1H, q, J=7.0 Hz), 4.63 (1H, s), 5.24 (2H, s), 7.28-7.40 (3H, m), 7.47 (2H, d, J=6.7 Hz).

Intermediate 56

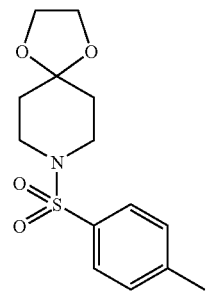

Intermediate 55 was dissolved in 15 mL TFA and stirred at rt for 16 h. The TFA was removed and the crude chromatographed on C1 8 using 10% $CH_3CN/H_2O$ initially as eluant. Product eluted with 20% $CH_3CN$. Pure fractions were concentrated and extracted with $CH_2Cl_2$. Evaporation of the solvent left 300 mg (Yield=51%) of the title compound 56. LC/MS (M+H): 279. $^1$H NMR (300 MHz, $CDCl_3$) δ: 1.41 (3H, t, J=7.1 Hz), 1.65-1.79 (4H, m), 1.84-1.97 (2H, m), 2.00-2.12 (4H, m), 3.98-4.08 (2H, m), 4.44 (2H, q, J=7.0 Hz), 10.78 (1H, s).

Intermediate 57

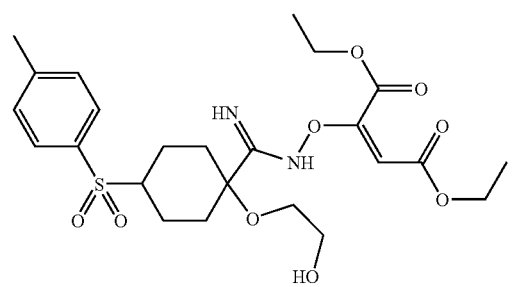

To a solution of 1,4-dioxa-8-azaspiro[4,5]decane (10.0 g, 70 mmol) and triethylamine (20 mL, 142 mmol) in diethylether (50 mL) cooled to 0° C. was added dropwise tosyl chloride (13.5 g, 71 mmol) dissolved in $CH_2Cl_2$. The resulting suspension was stirred at room temperature 5 h. and washed with saturated aqueous $NaHCO_3$, water and dried ($Na_2SO_4$). Concentration gave the Intermediate 57 as a white solid (20.20 g, 97%). $^1$H-NMR (300 MHz, $CDCl_3$) δ: 7.61 (2H, d, J=8.0 Hz), 7.28 (2H, d, J=8.0 Hz), 3.86 (4H, s), 3.11 (4H, t, J=5.8 Hz), 2.40 (3H, s), 1.75 (4H, t, J=5.8 Hz). LCMS (M+H) calcd for $C_{14}H_{20}NO_4S$: 298.1 1; found: 298.16.

Intermediate 58

To a stirred solution of zinc iodide (2.05 g, 6.26 mmol) and Intermediate 57 (9.3 g, 31.3 mmol) in dichloromethane (10 mL) was added trimethylsilylcyanide (4.29 mL, 31.3 mmol) with water bath cooling. The resulting mixture was stirred at room temp for 2 h and concentrated. The amber oil was used in the next step without purification.

To solution of above crude in EtOH (60 mL) was added hydroxylamine (2.1 mL, 31.3 mmol, 50wt % in water) and the resulting mixture was stirred at room temperature. After 18 h diethylacetylenedicarboxylate (6.0 mL, 37.5 mmol) was added and stirred for additional 3 days and concentrated. The residue was purified by flash chromatography eluting with 0%-25%-50% EtOAc/Hexane to give the Intermediate 58 as a yellow foam (11.72 g, 71%). $^1$H-NMR (300 MHz, $CDCl_3$) δ: 7.62 (2H, t, J=7.7 Hz), 7.30 (2H, t, J=8.2, 2.0 Hz), 5.27 (1H, s), 4.34-4.23 (2H, m), 4.19-4.05 (2H, m), 3.68-3.66 (2H, m), 3.54-3.49 (2H, m), 3.34-3.28 (2H, m), 2.72 (1H, dt, J=11.4, 2.5 Hz), 2.66-2.57 (1H, m), 2.40 (3H, d, J=1.6 Hz), 2.05-1.89

(4H, m), 1.35-1.22 (6H, m). LCMS (M+H) calcd for C$_{23}$H$_{34}$N$_3$O$_9$S: 528.20; found: 528.13.

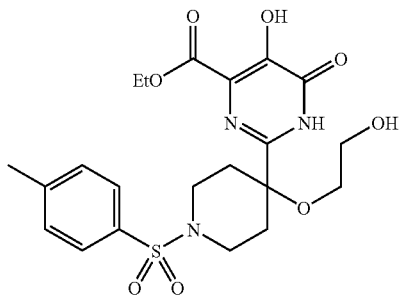

Intermediate 59

1,2,4-trimethylbenzene (100 mL) was added to Intermediate 58 (11.7 g, 22 mmol) and the mixture was stirred at 140° C. for 3 h. The mixture was cooled to room temp and concentrated. Residue dissolved in CH$_2$Cl$_2$ and insoluble solids removed by filtration and discarded. Concentration gave the Intermediate 59 as a brown foam (5.02 g, 47% yield). LCMS (M+H) calcd for C$_{21}$H$_{28}$N$_3$O$_8$S: 482.16; found: 482.11.

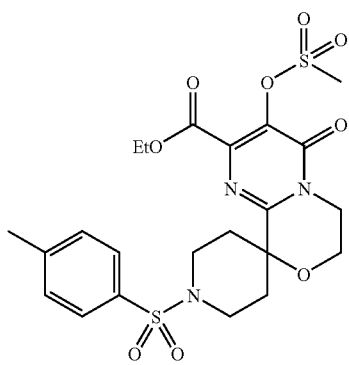

Intermediate 60

A solution of Intermediate 59 (3.0 g, 6.2 mmol) and triethylamine (2.5 mL, 18.7 mmol) in CH$_2$Cl$_2$ (8 mL) was cooled to 0° C. To this was added to methanesulfonylchloride (0.47 mL), 6.3 mmol) and the resulting mixture was stirred while gradually warming to room temperature for 18 h. The mixture was washed with water and the organic phase was dried (Na$_2$SO$_4$) to give a brown foam that was purified by flash chromatography eluting with 10%-50% EtOAc/hexane to give the Intermediate 60 as a yellow foam (0.477 g, 14% yield). $^1$H-NMR (300 MHz, CDCl$_3$) δ: 7.63 (2H, d, J=8.4 Hz), 7.31 (2H, d, J=8.0 Hz), 4.41 (2H, q, J=7.3 Hz), 3.92-3.89 (2H, m), 3.73-3.68 (1H, m), 3.49 (3H, s), 3.49-3.42 (1H, m), 2.63-2.48 (2H, m), 2.43-2.41 (4H, m), 1.94-1.90 (2H, d, J=13.5 Hz), 1.39 (3H, t, J=7.1 Hz). LCMS (M+H) calcd for C$_{22}$H$_{28}$N$_3$O$_9$S$_2$: 542.12; found: 542.03.

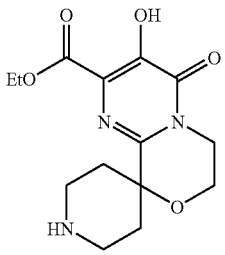

Intermediate 61

To a stirred solution of Intermediate 60 (0.411 g, 0.76 mmol) in THF (10 mL) at cooled to −78° C. was added dropwise a freshly prepared mixture of sodium (0.42 g, 20 mmol) dissolved in Naphthaline (2.56 g, 20 mmol) and THF (20 mL) until the blue color persisted. The resulting mixture stirred an additional 1 h and was quenched with 1N HCl. The aqueous layer was washed with EtOAc and freeze dried. The solids were purified by preparative HPLC (YMC Combiprep ODS-A, 30 mm×50 mm, MeOH/H2O/0.1% TFA), to give the Intermediate 61 as a white solid (0.024 g, 10% yield). LCMS (M+H) calcd for C$_{14}$H$_{20}$N$_3$O$_5$: 310.14; found: 310.10.

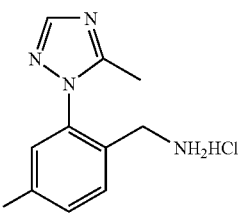

Intermediate 62

(4-fluoro-2-(5-methyl-1H-1,2,4-triazol-1-yl)phenyl) methanamine hydrochloride: Intermediate 62 was prepared according to procedure for intermediate 35. LCMS (M+H): 207.2.

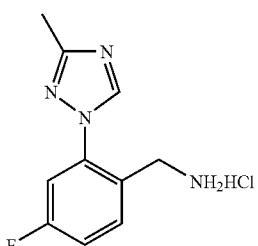

Intermediate 63

(4-fluoro-2-(3-methyl-1H-1,2,4-triazol-1-yl)phenyl) methanamine hydrochloride: Intermediate 63 was prepared according to procedure for intermediate 35. LCMS (M+H): 207.2.

Intermediate 64 and 65

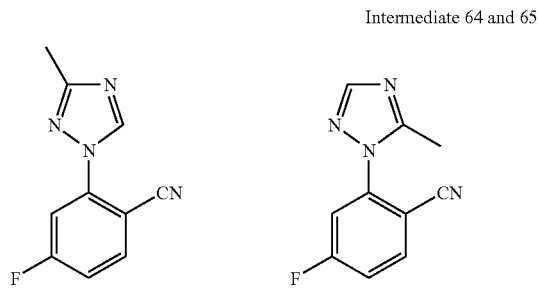

Intermediate 67

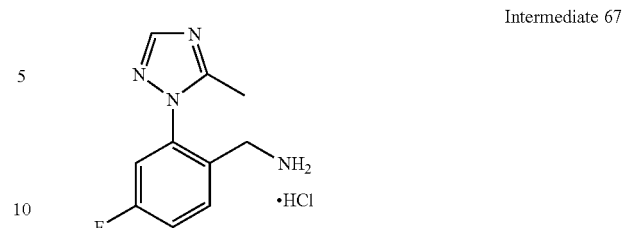

4-Fluoro-2-(3-methyl-1H-1,2,4-triazol-1-yl)benzonitrile and 4-fluoro-2-(5-methyl-1H-1,2,4-triazol-1-yl)benzonitrile. A solution of 2,4-difluorobenzonitrile (7.07 g, 50.8 mmol) and 3-methyl-1H-1,2,4-triazole (4.22 g, 50.8 mmol) in N,N-dimethylformamide (45 ml) was treated with powdered anhydrous potassium carbonate (10 g) and the resulting mixture was stirred at 22° C. for 18 h. The solid was then filtered and the filtrate was concentrated in vacuo. The residue was diluted with ethyl acetate, washed with water and brine, dried over anhydrous magnesium sulfate and concentrated. The mixture containing the 2 and 4-triazolyl-benzonitriles was purified by a combination of chromatography on silica gel ( elution gradient of ethyl acetate in hexane) and on reversed phase silica gel to give 1.86 g (18% yield) of Intermediate 64 and 0.526 g (5% yield) of Intermediate 65.

4-Fluoro-2-(3-methyl-1H-1,2,4-triazol-1-yl)benzonitrile white crystals (ethyl acetate-hexane); mp 117-118° C. $^1$HNMR 400 MHz (CDCl$_3$) δ (ppm): 2.54 (3H, s, CH$_3$), 7.24 (1H, m, CH), 7.62 (1H, dd, J=2.5 Hz and J=9.1 Hz, CH), 7.84 (1H, dd, J=5.6 Hz and J=8.6 Hz, CH), 8.82 (1H, s, CH). Anal. Calcd for C$_{10}$H$_7$FN$_4$: C 59.40, H 3.49, N 27.71; Found: C 59.25, H 3.32, N 27.81.

4-fluoro-2-(5-methyl-1H-1,2,4-triazol-1-yl)benzonitrile. white crystals (ethyl acetate-hexane); mp 120-121° C. $^1$HNMR 400 MHz (CDCl$_3$) δ (ppm): 2.56 (3H, s, CH$_3$), 7.30 (1H, dd, J=2.5 Hz and J=8.1 Hz, CH), 7.39 (1H, m, CH), 7.91 (1H, dd, J=5.5 Hz and J=8.6 Hz, CH), 8.06 (1H, s, CH). Anal. Calcd for C$_{10}$H$_7$FN$_4$: C 59.40, H 3.49, N 27.71; Found: C 59.35, H 3.70, N 27.77.

Intermediate 66

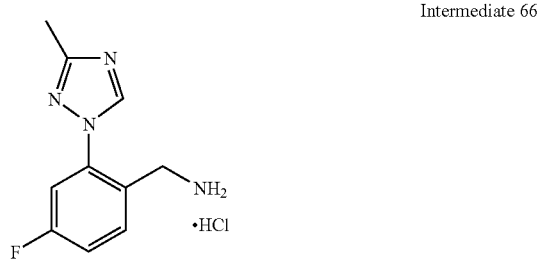

(4-Fluoro-2-(3-methyl-1H-1,2,4-triazol-1-yl)phenyl) methanamine hydrochloride salt. Hydrogenation of 4-fluoro-2-(3-methyl-1H-1,2,4-triazol-1-yl)benzonitrile (0.680 g, 3.36 mmol) gave 0.720 g (88% yield) of the title hydrochloride salt as a white solid. $^1$HNMR 400 MHz (DMSO-d$_6$) δ (ppm): 2.40 (3H, s, CH$_3$), 4.02 (2H, m, NCH$_2$), 7.50 (1H, m, CH), 7.62 (1H, dd, J=2.8 Hz and J=9.3Hz, CH), 7.84 (1H, dd, J=6.1 Hz and J=9.1 Hz, CH), 9.00 (1H, s, CH). HRMS (ESI$^+$) calculated for C$_{10}$H$_{12}$FN$_4$ [M+H$^+$]: 207.1046; found: 207.1047.

(4-Fluoro-2-(5-methyl-1H-1,2,4-triazol-1-yl)phenyl) methanamine hydrochloride salt. Hydrogenation of 4-fluoro-2-(5-methyl-1H-1,2,4-triazol-1-yl)benzonitrile (0.244 g, 1.20 mmol) gave 0.290 g (100% yield) of the title hydrochloride salt as a white solid. $^1$HNMR 400 MHz (DMSO-d$_6$) δ (ppm): 2.42 (3H, s, CH$_3$), 3.78 (2H, m, NCH$_2$), 7.58 (1H, m, CH), 7.67 (1H, dd, J=2.8 Hz and J=9.3 Hz, CH), 7.90 (1H, dd, J=6.0 Hz and J=8.6 Hz, CH), 8.22 (1H, s, CH). HRMS (ESI$^+$) calculated for C$_{10}$H$_{12}$FN$_4$ [M+H$^+$]: 207.1046; found: 207.1041.

Intermediate 68

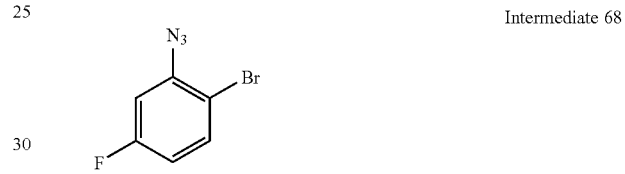

2-Azido-1-bromo-4-fluorobenzene. 2-Bromo-5-fluoro aniline (2.00 g, 10.53 mmol) was dissolved in concentrated HCl (10 mL) and water (10 mL) and cooled to 0° C. Aqueous NaNO$_2$ solution (1.09 g, 15.8 mmol of NaNO$_2$ in 10 mL of water) was added dropwise at such a rate that the temperature did not exceed 5° C. This mixture was stirred at 0° C. for 1.5 h. A solution of NaN$_3$ (1.027 g, 15.8 mmol) and NaOAc (12.95 g, 158 mmol) in water (50 mL) was then added at 0-5° C. and the mixture was stirred for an additional 1 h at this temperature. The mixture was extracted with ethyl acetate and the combined extracts were washed with brine and dried over Na$_2$SO$_4$. The filtrate was concentrated to afford the title compound as a tan solid (2.19 g, 96% yield): $^1$H NMR (400 MHz, CDCl$_3$): 7.53 (1 H, dd, J=8.8, 5.6 Hz), 6.94 (1 H, dd, J=8.8, 2.8 Hz), 6.79 (1 H, ddd, J=8.8, 7.6, 2.8 Hz).

Intermediate 69

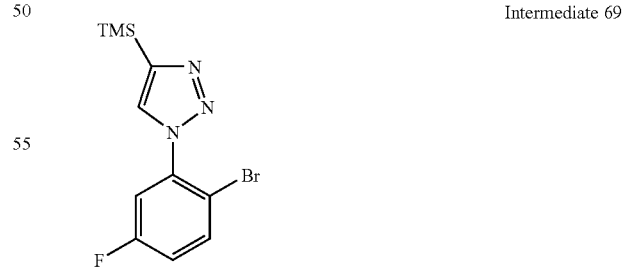

1-(2-Bromo-5-fluorophenyl)-4-(trimethylsilyl)-1H-1,2,3-triazole. A mixture of 2-azido-1-bromo-4-fluorobenzene (1.047 g, 4.85 mmol) and trimethylsilylacetylene (2.01 mL, 14.54 mmol) in toluene (5 mL) was heated in a pressure vessel at 110° C. for 21.5 h. The reaction mixture was concentrated in vacuo and the residue was purified with a Biotage system on silica gel with hexanes:ethyl acetate (9:1) gradient as the eluent to afford the title compound as a colorless oil (1.451 g, 95% yield): $^1$H NMR (400 MHz, CDCl$_3$) δ ppm: 7.97 (1H, s), 7.74 (1H, dd, J=9.0, 5.4 Hz), 7.37 (1H, dd, J=8.5, 2.9 Hz), 7.16 (1 H, ddd, J=8.8, 7.6, 3.0 Hz), 0.40 (9 H, s), LCMS ($^+$ESI, M+H$^+$) m/z 314/316.

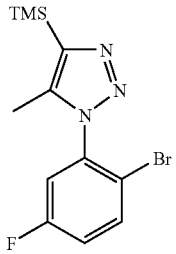

Intermediate 70

1-(2-Bromo-5-fluorophenyl)-5-methyl-4-(trimethylsilyl)-1H-1,2,3-triazole. The title compound can be prepared according to the procedure provided for 1-(2-bromo-5-fluorophenyl)-4-(trimethylsilyl)-1H-1,2,3-triazole $^1$H NMR (400 MHz, CDCl$_3$) δ ppm: 7.73-7.69 (1H, m), 7.20-7.16 (2H, m), 2.22 (3H, s), 0.39 (9H, s); LCMS ($^+$ESI, M+H$^+$) m/z 328/330.

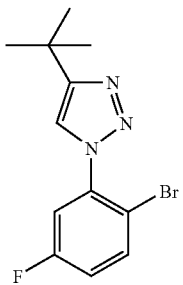

Intermediate 71

1-(2-Bromo-5-fluorophenyl)-4-tert-butyl-1H-1,2,3-triazole. The title compound can be prepared according to the procedure provided for 1-(2-bromo-5-fluorophenyl)-4-(trimethylsilyl)-1H-1,2,3-triazole $^1$H NMR (400 MHz, CDCl$_3$) δ ppm: 7.68-7.75 (2 H, m), 7.38 (1 H, dd, J=8.5, 2.9 Hz), 7.14 (1 H, ddd, J=8.8, 7.6, 3.0 Hz), 1.43 (9 H, s), LCMS ($^+$ESI, M+H$^+$) m/z 298/300.

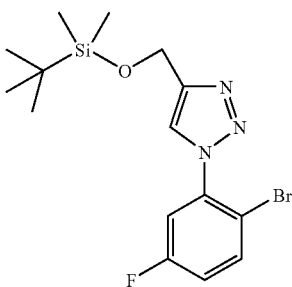

Intermediate 72

1-(2-Bromo-5-fluorophenyl)-4-((tert-butyldimethylsilyloxy)methyl)-1H-1,2,3-triazole. The title compound can be prepared according to the procedure provided for 1-(2-bromo-5-fluorophenyl)-4-(trimethylsilyl)-1H-1,2,3-triazole $^1$H NMR (400 MHz, CDCl$_3$) δ ppm: 7.95 (1 H, s), 7.75 (1 H, dd, J=9.0, 5.4 Hz), 7.38 (1 H, dd, J=8.3, 3.0 Hz), 7.17 (1 H, ddd, J=9.0, 7.5, 2.8 Hz), 4.96 (2 H, s), 0.93 (9 H, s), 0.13 (6 H, s), LCMS ($^+$ESI, M+H$^+$) m/z 386/388.

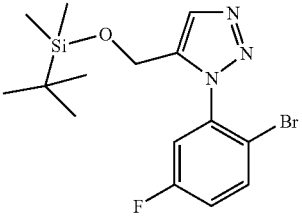

Intermediate 73

1-(2-Bromo-5-fluorophenyl)-5-((tert-butyldimethylsilyloxy)methyl)-1H-1,2,3-triazole. The title compound can be prepared according to the procedure provided for 1-(2-bromo-5-fluorophenyl)-4-(trimethylsilyl)-1H-1,2,3-triazole 1H NMR (400 MHz, CDCl$_3$) δ ppm: 7.70-7.78 (2 H, m), 7.19-7.30 (2 H, m), 4.67 (2 H, s), 0.82 (9H, s), −0.03 (6 H, s), LCMS ($^+$ESI, M+H$^+$) m/z 386/388.

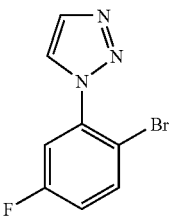

Intermediate 74

1-(2-Bromo-5-fluorophenyl)-1H-1,2,3-triazole. 1-(2-Bromo-5-fluorophenyl)-4-(trimethylsilyl)-1H-1,2,3-triazole (0.80 g, 2.55 mmol) was dissolved in tetrahydrofuran (10 mL) and tetrabutylammonium fluoride (2.8 mL, 2.80 mmol, 1.0 M in tetrahydrofuran) was added dropwise and the reaction mixture was stirred at 25° C. for 4 h. The resulting mixture was concentrated in vacuo and the residue was purified with a Biotage system on silica gel with hexanes:ethyl acetate (8:2 to 7:3) gradient as the eluent to afford the title compound as a white solid (0.36 g, 58% yield): $^1$H NMR (400 MHz, CDCl$_3$) δ ppm: 8.06 (1 H, d, J=1.0 Hz), 7.90 (1 H, d, J=1.3 Hz), 7.76 (1 H, dd, J=8.8, 5.3 Hz), 7.39 (1 H, dd, J=8.3, 2.8 Hz), 7.19 (1 H, ddd, J=8.9, 7.5, 3.0 Hz), LCMS (+ESI, M+H$^+$) m/z 242/244.

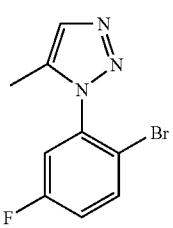

Intermediate 75

1-(2-Bromo-5-fluorophenyl)-5-methyl-1H-1,2,3-triazole. The title compound can be prepared according to the procedure provided for 1-(2-bromo-5-fluorophenyl)-1H-1,2,3-triazole $^1$H NMR (400 MHz, CDCl$_3$) δ ppm: 7.76 (1 H, dd, J=9.1, 5.3 Hz), 7.62 (1 H, s), 7.19-7.26 (2 H, m), 2.25 (3 H, s), LCMS ($^+$ESI, M+H$^+$) m/z 256/258.

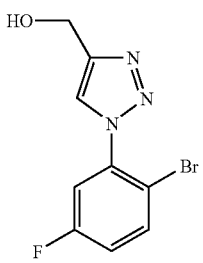

Intermediate 76

(1-(2-Bromo-5-fluorophenyl)-1H-1,2,3-triazol-4-yl)methanol. The title compound can be prepared according to the procedure provided for 1-(2-bromo-5-fluorophenyl)-1H-1,2,3-triazole $^1$H NMR (400 MHz, CDCl$_3$) δ ppm: 8.02 (1 H, s), 7.75 (1 H, dd, J=8.8, 5.3 Hz), 7.38 (1 H, dd, J=8.2, 2.9 Hz), 7.19 (1 H, ddd, J=8.9, 7.5, 3.0 Hz), 4.94 (2 H, s), LCMS ($^+$ESI, M+H$^+$) m/z 270/272.

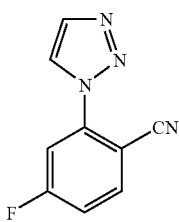

Intermediate 77

4-Fluoro-2-(1H-1,2,3-triazol-1-yl)benzonitrile. A mixture of 1-(2-bromo-5-fluorophenyl)-1H-1,2,3-triazole (0.603 g, 2.49 mmol), CuCN (0.245 g, 2.74 mmol), and 15 mL of NMP was subjected to microwave irradiation at 150° C. for 0.5 h. The brown mixture was filtered over celite and washed with dimethylfomamide. This solution was treated with 10% aqueous NH$_4$OH (28-30% solution) and extracted with ethyl acetate. The combined organic layers were successively washed with 10% aqueous NH$_4$OH (28-30% solution), sat. NH$_4$Cl aq., water, brine and dried over Na$_2$SO$_4$. The resulting mixture was concentrated in vacuo and the residue was purified with a Biotage system on silica gel with hexanes:ethyl acetate (7:3 to 6:4) gradient as the eluent to afford the title compound as a light yellow solid (0.285 g, 61% yield): $^1$H NMR (400 MHz, CDCl$_3$) δ ppm: 8.40 (1 H, d, J=1.0 Hz), 7.96 (1 H, s), 7.91 (1 H, dd, J=8.6, 5.6 Hz), 7.77 (1 H, dd, J=8.7, 2.4 Hz), 7.31-7.39 (1 H, m).

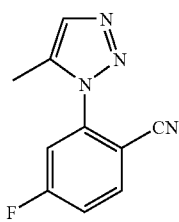

Intermediate 78

4-Fluoro-2-(5-methyl-1H-1,2,3-triazol-1-yl)benzonitrile. The title compound can be prepared according to the procedure provided for 4-fluoro-2-(1H-1,2,3-triazol-1-yl)benzonitrile $^1$H NMR (400 MHz, CDCl$_3$) δ ppm: 7.93 (1 H, dd, J=8.7, 5.4 Hz), 7.67 (1 H, s), 7.44 (1 H, ddd, J=8.6, 7.6, 2.5 Hz), 7.35 (1 H, dd, J=8.1, 2.5 Hz), 2.39 (3 H, s), LCMS ($^+$ESI, M+H$^+$) m/z 203.

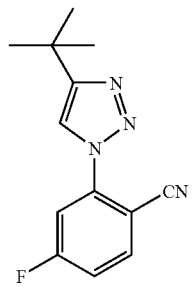

Intermediate 79

2-(4-tert-Butyl-1H-1,2,3-triazol-1-yl)-4-fluorobenzonitrile. The title compound can be prepared according to the procedure provided for 4-fluoro-2-(1H-1,2,3-triazol-1-yl)benzonitrile $^1$H NMR (400 MHz, CDCl$_3$) δ ppm: 8.07 (1 H, s), 7.87 (1 H, dd, J=8.8, 5.6 Hz), 7.74 (1 H, dd, J=8.8, 2.5 Hz), 7.25-7.33 (1 H, m), 1.45 (9 H, s), LCMS ($^+$ESI, M+H$^+$) m/z 245.

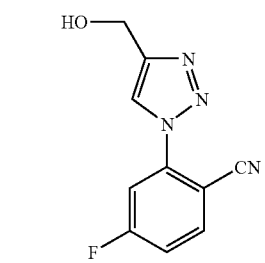

Intermediate 80

4-Fluoro-2-(4-(hydroxymethyl)-1H-1,2,3-triazol-1-yl)benzonitrile. The title compound can be prepared according to the procedure provided for 4-fluoro-2-(1H-1,2,3-triazol-1-yl)benzonitrile $^1$H NMR (400 MHz, CDCl$_3$) δ ppm: 8.34 (1 H, s), 7.91 (1 H, dd, J=8.7, 5.4 Hz), 7.74 (1 H, dd, J=8.6, 2.5 Hz), 7.35 (1 H, ddd, J=8.8, 7.3, 2.5 Hz), 4.96 (2 H, s), LCMS ($^+$ESI, M+H$^+$) m/z 219.

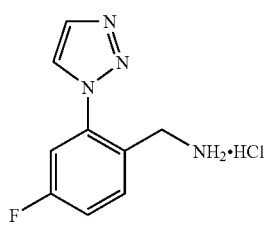

Intermediate 81

(4-Fluoro-2-(1H-1,2,3-triazol-1-yl)phenyl)methanamine hydrochloride. $^1$H NMR (400 MHz, DMSO-D6) δ ppm: 8.73 (1 H, d, J=1.0 Hz), 8.53 (3 H, brs), 8.07 (1 H, d, J=1.0 Hz), 7.91 (1 H, dd, J=8.7, 5.9 Hz), 7.66 (1 H, dd, J=9.2, 2.7 Hz), 7.60 (1 H, td, J=8.5, 2.7 Hz), 3.92 (2 H, q, J=5.6 Hz), LCMS ($^+$ESI, M+H$^+$) m/z 193.

Intermediate 82

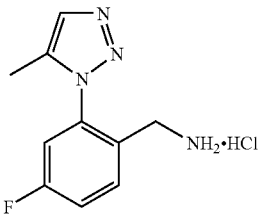

(4-Fluoro-2-(5-methyl-1H-1,2,3-triazol-1-yl)phenyl)methanamine hydrochloride;. $^1$H NMR (400 MHz, DMSO-D6) δ ppm: 8.61 (2 H, s), 7.98 (1 H, dd, J=9.5, 6.2 Hz), 7.80 (1 H, s), 7.61-7.67 (2 H, m), 3.66 (2 H, q, J=5.7 Hz), 2.26 (3H, s), LCMS ($^+$ESI, M+H$^+$) m/z 206.

Intermediate 83

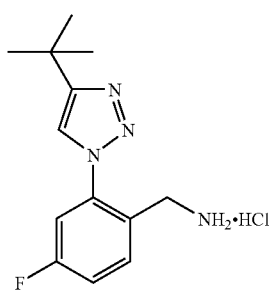

(2-(4-tert-Butyl-1H-1,2,3-triazol-1-yl)-4-fluorophenyl)methanamine hydrochloride. $^1$H NMR (400 MHz, DMSO-D6) δ ppm: 8.55 (2 H, brs), 8.52 (1 H, s), 7.89 (1 H, dd, J=8.8, 6.1 Hz), 7.65 (1 H, dd, J=9.3, 2.5 Hz), 7.55 (1 H, td, J=8.5, 2.5 Hz), 3.95 (2 H, q, J=5.6 Hz), 1.36 (9 H, s), LCMS ($^+$ESI, M+H$^+$) m/z 249.

Intermediate 84

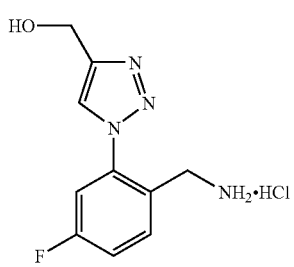

(1-(2-(aminomethyl)-5-fluorophenyl)-1H-1,2,3-triazol-4-yl)methanol hydrochloride. $^1$H NMR (400 MHz, DMSO-D6) δ ppm: 8.56 (1 H, s), 8.50 (2 H, s), 7.89 (1 H, dd, J=8.7, 5.9 Hz), 7.63 (1 H, dd, J=9.2, 2.7 Hz), 7.58 (1 H, td, J=8.5, 2.8 Hz), 4.65 (2 H, s), 3.94 (2 H, q, J=5.4 Hz), LCMS ($^+$ESI, M+H$^+$) m/z 223.

Intermediate 85

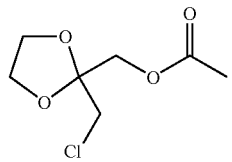

(2-(Chloromethyl)-1,3-dioxolan-2-yl)methyl acetate. A solution of 1-acetoxy-3-chloroacetone (20.0 g, 133 mmol, TCI America) and 1,2-bis(trimethylsilyloxy)ethane (30.2 g, 146 mmol, Aldrich) in anhydrous CH$_2$Cl$_2$ and under N$_2$ atmosphere was cooled (−78° C., dry ice/acetone) and trimethylsilyl trifluoromethanesulfonate (1.2 mL, 6.6 mmol, Aldrich) was added. The reaction was warmed to room temperature and stirred for 5 days, with monitoring by $^1$H-NMR. The crude reaction solution was separated by silica gel column, and eluted with CH$_2$Cl$_2$, then 5% Et$_2$O in CH$_2$Cl$_2$. Product fractions were pooled and concentrated in-vacuo giving the title compound (19.05 g) as a yellow oil, contaminated with 1-acetoxy-3-chloroacetone (2.93 g) and CH$_2$Cl$_2$ (1.0 g): $^1$H NMR (500 MHz, CDCl$_3$) δ ppm 4.17 (2H, s), 4.03-4.11 (4H, m), 3.60 (2H, s), 2.09 (3H, s).

Intermediate 86

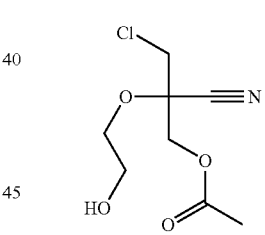

3-Chloro-2-cyano-2-(2-hydroxyethoxy)propyl acetate. A mixture of (2-(chloromethyl)-1,3-dioxolan-2-yl)methyl acetate (67.8 mmol), trimethylsilyl cyanide (20.29 g, 204 mmol, TCI America) and zinc iodide (3.65 g, 11.4 mmol) was heated (40° C., oil bath) for 6 hrs, then at ambient temperature for 16 hrs. The mixture was diluted with CH$_2$Cl$_2$ (100 mL) and stirred with silica gel (50 g) for several hours. The mixture was loaded onto a flash silica gel column (350 g silica) and eluted with CH$_2$Cl$_2$ then increasing amounts of Et$_2$O to a final eluent of 30% Et$_2$O in CH$_2$Cl$_2$. Product fractions were pooled and concentrated in-vacuo to give the title compound as an amber oil: $^1$H NMR (500 MHz, CDCl$_3$) δ ppm 4.44 (1H, d, J=-11.90 Hz), 4.35 (1H, d, J=11.90 Hz), 3.83-3.88 (2H, m), 3.79-3.84 (4H, m), 2.13-2.16 (3H, m); LC/MS m/z 222.16 (M+H).

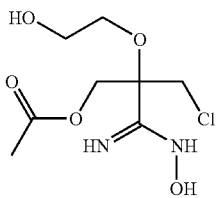

Intermediate 87

2-(Chloromethyl)-3-(hydroxyamino)-2-(2-hydroxyethoxy)-3-iminopropyl acetate. A solution of 3-chloro-2-cyano-2-(2-hydroxyethoxy)propyl acetate (9.40 g, 42.4 mmol) in ethanol (150 mL) was treated with 50% aqueous hydroxylamine solution (2.94 g, 44.5 mmol, Aldrich) and the reaction was heated (65° C.) for 1.5 hrs. The solution was cooled to room temperature and the product was used as-is in the subsequent reaction: LC/MS m/z 255.20 (M+H).

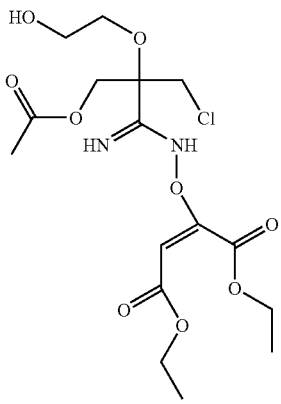

Intermediate 88

2-{[3-Acetoxy-2-chloromethyl-2-(2-hydroxy-ethoxy)-propionimidoyl]-aminooxy}-but-2-enedioic acid diethyl ester. The ethanol solution of 2-(chloromethyl)-3-(hydroxyamino)-2-(2-hydroxyethoxy)-3-iminopropyl acetate, obtained above, was treated with diethyl acetylenedicarboxylate (46.6 mmol, Alfa Aesar) and stirred 16 hrs. Solvent was removed in-vacuo and the resultant amber oil was dissolved in ethyl acetate (100 mL) and washed with water (2×100 mL). The organic layer was dried (Na$_2$SO$_4$), filtered and concentrated in-vacuo. The crude product was purified by flash column chromatography, eluting with 30%-50% ethyl acetate in hexanes. Product fractions were pooled and concentrated in-vacuo to give the title compound (11.1 g) as a viscous amber oil: LC/MS m/z 425.19 (M+H).

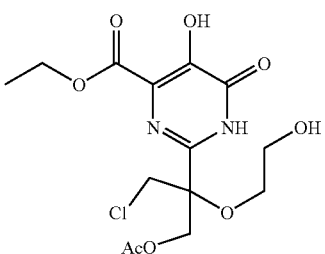

Intermediate 89

Ethyl 2-(3-acetoxy-1-chloro-2-(2-hydroxyethoxy)propan-2-yl)-5-hydroxy-6-oxo-1,6-dihydropyrimidine-4-carboxylate. A solution of 2-{[3-acetoxy-2-chloromethyl-2-(2-hydroxy-ethoxy)-propionimidoyl]-aminooxy}-but-2-enedioic acid diethyl ester (11.1 g, 26.13 mmol) in 1,2,4-trimethyl benzene (260 mL, Aldrich) was heated at reflux (160° C., oil bath) for 90 minutes. The reaction was cooled and the solvent was removed in-vacuo. The crude product was dissolved in ethyl acetate (100 mL) and extracted into saturated NaHCO$_3$ aqueous solution (4×50 mL). The combined extracts were brought to pH~1 using 6.0 N HCl, and re-extracted into ethyl acetate (3×75 mL). The combined extracts were dried (Na$_2$SO$_4$), filtered, and concentrated in-vacuo to give a pale yellow solid This was triturated with Et$_2$O, and solids were collected by filtration, followed by drying in-vacuo, to give the title compound as an off-white solid: $^1$H NMR (500 MHz, CDCl$_3$) δ ppm 12.13 (1H, br), 10.86 (1H, br), 4.76 (1H, d, J=11.90 Hz), 4.44 (2H, q, J=7.02 Hz), 4.32 (1H, d J=11.90 Hz), 4.08 (1H, d, J=12.5), 4.00 (1H, d, J=12.5), 3.83-3.95 (2H, m), 3.66-3.78 (2H, m), 2.02 (3H, s), 1.42 (3H, t, J=7.17 Hz); $^{13}$NMR (126 MHz, CDCl$_3$) δ ppm 170.23, 168.97, 159.39, 150.15, 147.87, 126.88, 79.86, 65.94, 63.91, 62.86, 61.37, 44.33, 20.78, 14.20; HRMS (ESI) calcd for C$_{14}$H$_{20}$N$_2$O$_8$Cl (M+H) 379.0908; found 379.0896.

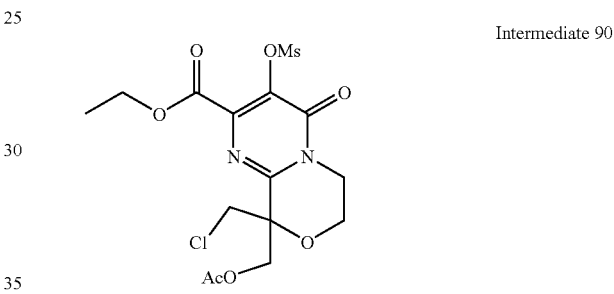

Intermediate 90

Ethyl 9-(acetoxymethyl)-9-(chloromethyl)-3-(methylsulfonyloxy)-4-oxo-4,6,7,9-tetrahydropyrimido[2,1-c][1,4]oxazine-2-carboxylate. A solution of ethyl 2-(3-acetoxy-1-chloro-2-(2-hydroxyethoxy)propan-2-yl)-5-hydroxy-6-oxo-1,6-dihydropyrimidine-4-carboxylate (2.322 g, 6.13 mmol) in tetrahydrofuran (100 mL) was treated with methane sulfonylchloride (2.11 g, 18.4 mmol) and Et$_3$N (2.25 g, 22 mmol) and then heated (60° C., oil bath) for 3 hrs. Solvent was removed in-vacuo and the crude product was dissolved in ethyl acetate (100 mL), then washed with water (2×50 mL). The organic solution was dried (Na$_2$SO$_4$), filtered and concentrated in-vacuo to give the title compound as a viscous amber oil which was used immediately in the following reaction.

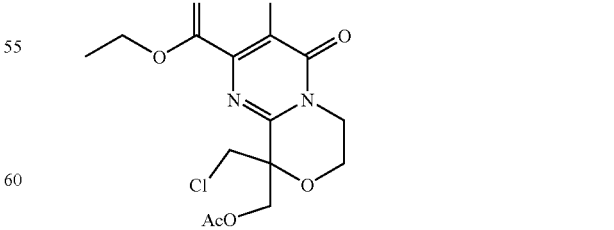

Intermediate 91

Ethyl 9-(acetoxymethyl)-9-(chloromethyl)-3-hydroxy-4-oxo-4,6,7,9-tetrahydropyrimido[2,1-c][1,4]oxazine-2-carboxylate. A solution of ethyl 9-(acetoxymethyl)-9-(chloromethyl)-3-(methylsulfonyloxy)-4-oxo-4,6,7,9- tetrahydropyrimido[2,1-c][1,4]oxazine-2-carboxylate, obtained above, in absolute ethanol (120 mL) was treated with solid sodium ethoxide (0.440 g, 6.13 mmol, 95%, Aldrich) and stirred for 30 min. The reaction was monitored by HPLC, and additional sodium ethoxide in ethanol (0.5 mL, 1.34 mmol, 21 wt %, Aldrich) was added. The reaction was stirred 20 minutes and then concentrated in-vacuo. The crude material was dissolved in ethyl acetate (20 mL) and washed with 0.05 N HCl aqueous solution (40 mL). The organic solution was dried (Na$_2$SO$_4$), filtered, and concentrated in-vacuo to give the title compound (2.05 g) as an amber oil: LC/MS m/z 361.19 (M+H)

Intermediate 92

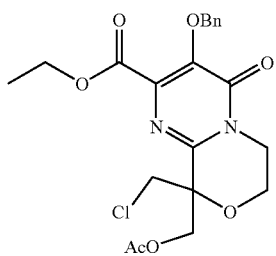

Ethyl 9-(acetoxymethyl)-3-(benzyloxy)-9-(chloromethyl)-4-oxo-4,6,7,9-tetrahydropyrimido[2,1-c][1,4]oxazine-2-carboxylate. A solution of ethyl 9-(acetoxymethyl)-9-(chloromethyl)-3-hydroxy-4-oxo-4,6,7,9-tetrahydropyrimido[2,1-c][1,4]oxazine-2-carboxylate (2.05 g, 5.68 mmol) in dimethylfomamide (60 mL) was treated with benzyl bromide (1.46 g, 8.5 mmol, Aldrich) and K$_2$CO$_3$ (1.26 g, 9.1 mmol) and stirred for 16 hrs. Solvent was removed in-vacuo and the crude material was dissolved in ethyl acetate (30 mL) and washed with water (30 mL) and brine (30 mL). The organic solution was dried (Na$_2$SO$_4$), filtered, and concentrated to give an amber oil. This was purified by flash column chromatography, eluting with 5% Et$_2$O in CH$_2$Cl$_2$. Product fractions were pooled and concentrated in-vacuo to give the title compound as a colorless oil: $^1$H NMR (500 MHz, CDCl$_3$) δ ppm 7.45 (2H, d, J=7.32 Hz), 7.29-7.39 (3H, m), 4.68 (1H, d, J=11.90 Hz), 4.37 (1H, d, J=11.90 Hz), 4.31 (2H, q, J=7.22 Hz), 4.16-4.24 (2H, m), 4.09-4.16 (1H, m), 4.06 (1H, d, J=11.29 Hz), 3.95-4.03 (1H, m), 3.89 (1H, d, J=1 1.29 Hz), 2.06 (3H, s), 1.56 (2H, s), 1.29 (3H, t, J=7.17 Hz); $^{13}$C NMR (126 MHz, CDCl$_3$) δ ppm 170.16, 164.04, 158.67, 150.65, 141.94, 141.67, 136.51, 128.59 128.52, 128.45, 79.57, 74.51, 65.90, 62.11, 60.59, 49.08, 42.16, 20.83, 14.16; HRMS (ESI) calcd for C$_{21}$H$_{24}$N$_2$O$_7$Cl (M+H) 451.1272; found 451.1274.

Intermediate 93

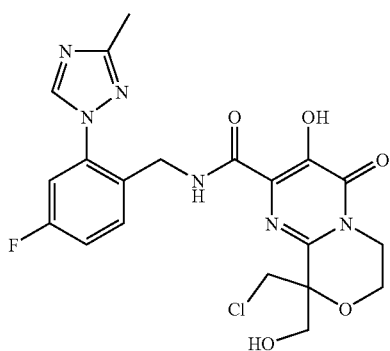

N-(4-Fluoro-2-(3-methyl-1H-1,2,4-triazol-1-yl)benzyl)-9-(chloromethyl)-3-hydroxy-9-(hydroxymethyl)-4-oxo-4,6,7,9-tetrahydropyrimido[2,1-c][1,4]oxazine-2-carboxamide. A solution of ethyl 9-(acetoxymethyl)-3-(benzyloxy)-9-(chloromethyl)-4-oxo-4,6,7,9-tetrahydropyrimido[2,1-c][1,4]oxazine-2-carboxylate (1.0 g) in trifluoroacetic acid (5 mL) CH$_2$Cl$_2$ (5 mL) was stirred for 2 hrs. An aliquot was transferred to a separate reaction flask and concentrated to give des-OBn intermediate (0.363 g, 1.01 mmol). This was immediately dissolved in dimethylfomamide (2 mL) and ethanol (2 mL) and treated with (4-fluoro-2-(3-methyl-1H-1,2,4-triazol-1-yl)benzylamine hydrochloride (0.320 g, 1.31 mmol) and triethyl amine (0.75 mL, 5.2 mmol), and heated (90° C.) for 5 hrs. To the reaction was added Cs$_2$CO$_3$ (0.340 g, 1.1 mmol) and water (1 mL) and the reaction stirred for 2.5 hrs. The reaction was concentrated in-vacuo and the resultant crude material was suspended in water (10 mL) and extracted into CH$_2$Cl$_2$ (2×10 mL). The combined extracts were dried (Na$_2$SO$_4$), filtered, and concentrated to give a solid which was then triturated with a small volume of 95% ethanol. The resultant precipitate was collected by filtration and dried in-vacuo to give the title compound as a white crystalline solid: $^1$H NMR (500 MHz, CDCl$_3$) δ ppm 12.18-12.31 (1H, m), 8.49 (1H, t, J=6.26 Hz), 8.32 (1H, s), 7.67 (1H, dd, J=8.39, 5.95 Hz), 7.19 (1H, dt, J=8.16, 2.29 Hz), 7.08 (1H, dd, J=8.39, 2.29Hz), 5.29 (2H, s), 4.54 (1H, dd, J=14.19, 6.87 Hz), 4.19-4.27 (1H, m), 4.12-4.18 (1H, m), 4.10 (2H, t, J=4.58 Hz), 4.00 (2H, t, J=12.21 Hz), 3.90-3.96 (2H, m), 2.55 (3H, s); $^{13}$C NMR (126 MHz, CDCl$_3$) δ ppm 167.69, 163.26, 162.49, 157.34, 147.41, 146.32, 144.26, 134.31, 134.24, 128.45, 128.42, 125.59, 116.93, 116.76, 112.41, 112.21, 80.41, 66.93, 60.79, 53.52, 48.62, 42.47, 39.41, 14.12; HRMS ESI) calcd for C$_{20}$H$_{21}$N$_6$O$_5$FCl (M+H) 479.1246, found 479.1224; Elem. Anal. calcd for C$_{20}$H$_{20}$N$_6$O$_5$FCl: C 49.79, H 4.26, N 17.42, found: C 50.11, H 4.10, N 17.28.

Intermediate 94

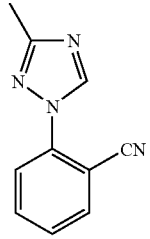

2-(3-Methyl-1H-1,2, 4-triazol-1-yl)benzonitrile. White crystals; mp 109-110° C. (ethyl acetate-hexane). $^1$HNMR 400 MHz (CDCl$_3$) δ (ppm): 2.54 (3H, s, CH$_3$), 7.5-7.58 (1H, m, aromatic), 7.75-7.8 (2H, m, aromatics), 7.82-7.86 (1H, m, aromatic), 8.68 (1H, s, CH). Anal. Calcd for C$_{10}$H$_8$N$_4$: C 65.20, H 4.37, N 30.41; Found: C 64.99, H 4.09, N 30.50.

Intermediate 95

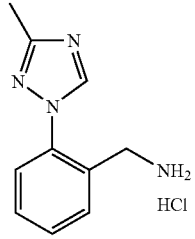

(2-(3-Methyl-1H-1,2,4-triazol-1-yl)phenyl)methanamine hydrochloride. White solid. $^1$HNMR 400 MHz (DMSO-d$_6$) δ

(ppm): 2.41 (3H, s, CH$_3$), 4.01 (2H, m, CH$_2$), 7.6 (3H, m, aromatics), 7.78 (1H, m, aromatic), 8.5 (broad, NH), 8.98 (1H, s, CH). MS (ESI$^+$) m/e 189 [M+H$^+$].

Intermediate 96

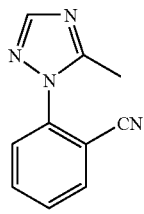

2-(5-Methyl-1H-1,2,4-triazol-1-yl)benzonitrile. White crystals; mp 119-120° C. (ethyl acetate-hexane). $^1$HNMR 400 MHz (CDCl$_3$) δ (ppm): 2.52 (3H, s, CH$_3$), 7.55 (1H, m, aromatic), 7.67 (1H, m, aromatic), 7.82 (1H, m, aromatic), 7.89 (1H, m, aromatic), 8.05 (1H, s, CH). Anal. Calcd for C$_{10}$H$_8$N$_4$: C 65.20, H 4.37, N 30.41; Found: C 64.97, H 4.07, N 30.42.

Intermediate 97

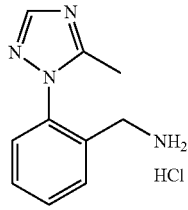

(2-(5-Methyl-1H-1,2,4-triazol-1-yl)phenyl)methanamine hydrochloride. White solid. $^1$HNMR 400 MHz (DMSO-d$_6$) δ (ppm): 2.38 (3H, s, CH$_3$), 3.80 (2H, m, CH$_2$), 7.56-7.7 (3H, m, aromatics), 7.8-7.82 (1H, m, aromatic), 8.17 (1H, s, CH), 8.44 (broad, NH). MS (ESI$^+$) m/e 189 [M+H$^+$].

Intermediate 98

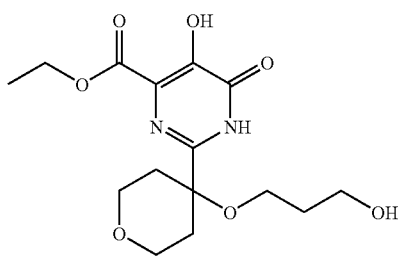

Ethyl 5-hydroxy-2-(4-(3-hydroxypropoxy)-tetrahydro-2H-pyran-4-yl)-6-oxo-1,6-dihydropyrimidine-4-carboxylate. Clear yellow oil. $^1$HNMR 400 MHz (CDCl$_3$) δ (ppm): 1.43 (3H, t, J=7.1 Hz, CH$_3$), 1.8-2.3 (6H, m, 3×CH$_2$), 3.44 (2H, t, J=5.5 Hz, CH$_2$), 3.6-4.0 (6H, m, 3×CH$_2$), 4.44 (2H, q, J=7.1 Hz, OCH$_2$), 10.8 (1H, broad, OH). HRMS (ESI$^+$) calculated for C$_{15}$H$_{23}$N$_2$O$_7$ [M+H$^+$]: 343.1505; found: 343.1499.

Intermediate 88

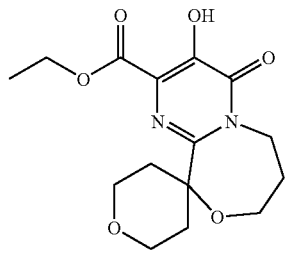

White crystals; mp 140-142° C. (ethyl acetate). $^1$HNMR 400 MHz (CDCl$_3$) δ (ppm): 1.46 (3H, t, J=7.1 Hz, CH$_3$), 1.86 (2H, m, CH$_2$), 2.02 (2H, m, CH$_2$), 2.43 (2H, m, CH$_2$), 3.75 (2H, m, CH$_2$), 3.83-3.91 (4H, m, 2×CH$_2$), 4.46 (2H, q, J=7.1 Hz, OCH$_2$), 4.6 (2H, broad m, CH$_2$), 10.62 (1H, broad, OH). Anal. Calcd for C$_{15}$H$_{20}$N$_2$O$_6$: C 55.55, H 6.21, N 8.63; Found: C 55.56, H 6.22, N 8.55.

Intermediate 100

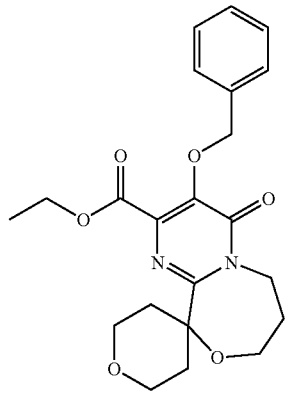

Clear oil. ¹HNMR 400 MHz (CDCl₃) δ (ppm): 1.33 (3H, t, J=7.1 Hz, CH₃), 1.86 (2H, m, CH₂), 2.03 (2H, m, CH₂), 2.42 (2H, m, CH₂), 3.77 (2H, m, CH₂), 3.8-3.9 (4H, m, 2×CH₂), 4.36 (2H, q, J=7.1 Hz, OCH₂), 4.55 (2H, broad m, CH₂), 5.28 (2H, s, OCH₂), 7.3-77.4 (3H, m, aromatics), 7.5 (2H, m, aromatics). MS (ESI⁺) m/e 415 [M+H⁺].

Intermediate 101

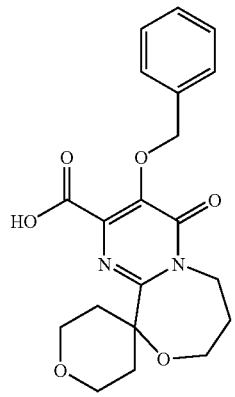

White crystals; mp 185-186° C. (ethyl acetate). ¹HNMR 400 MHz (CDCl₃) δ (ppm): 1.89 (2H, m, CH₂), 2.06 (2H, m, CH₂), 2.34 (2H, m, CH₂), 3.77 (2H, m, CH₂), 3.8-3.92 (4H, m, 2×CH₂), 4.58 (2H, broad m, CH₂), 5.50 (2H, s, OCH₂), 7.3-7.4 (3H, m, aromatics), 7.56 (2H, m, aromatics). Anal. Calcd for C₂₀H₂₂N₂O₆: C 62.16, H 5.73, N 7.25; Found: C 62.29, H 5.78, N 7.17.

EXAMPLE 1

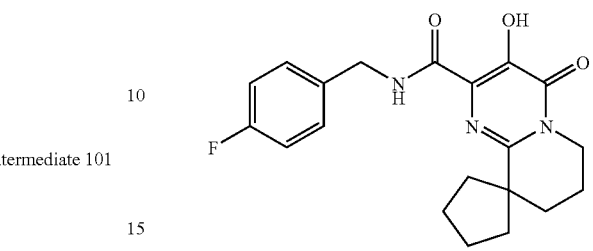

A mixture of ester 3 (0.146 g, .499 mmol), 4-fluorobenzylamine (0.156 g, 1.25 mmol, and triethylamine (0.14 mL, 1 mmol) in 1:1 DMF/EtOH (2 mL) was heated at 110° C. for 1.5 h. Then, the reaction mixture was cooled and purified preparative HPLC using MeOH/water containing 0.1 F TFA (gradient elution). The fractions containing the product were combined and evaporated to afforded the product as a white solid (0.0955 g, 51.5%). ¹H NMR (500 MHz, CDCl₃) δ: 11.70 (1H, s), 7.86 (1H, br t), 7.32-7.29 (2H, m), 7.05 (2H, t, J=8.6 Hz), 4.59 (2H, d, J=6.4 Hz), 4.01 (2H, t, J=6.4 Hz), 2.16-2.11 (2H, m), 1.99-1.94 (2H, m), 1.82-1.65 (8H, m). HRMS (M+H) calcd for C₂₀H₂₃FN₃O₃: 372.1724; found: 371.1714. Anal calcd for C₂₀H₂₂FN₃O₃: C, 64.67; H, 5.97; N, 11.31. Found: C, 64.58; H, 6.24; N, 11.11.

Other examples made by similar methods using amine (2-10 equiv), Et₃N (2-10 equiv.) and appropriate ester in DMF, DMF/EtOH, or other solvent system at 60° C.-140° C. are listed in Table 3.

TABLE 3

| Ex. | Structure | Data |
|---|---|---|
| 2 | (structure: 3-methyl-4-fluorobenzylamide of pyrimidinone-spirocyclopentane) | Yield: 43%. ¹H NMR (500 MHz, CDCl₃) δ: 11.72 (1H, s), 7.84 (1H, br t), 7.15-7.09 (2H, m), 6.99 (1H, t, J=8.9 Hz), 4.55 (2H, d, J=6.1 Hz), 4.01 (2H, t, J=6.4 Hz), 2.28 (3H, s), 2.17-2.12 (2H, m), 1.99-1.94 (2H, m), 1.83-1.65 (8H, m). HRMS (M + H) calcd for C₂₁H₂₅FN₃O₃: 386.188; found: 386.1875. Anal calcd for C₂₁H₂₄FN₃O₃·0.03 H₂O·0.05 CH₂Cl₂: C, 64.79; H, 6.24; N, 10.77; found: C, 64.71; H, 6.31; N, 10.71. |

TABLE 3-continued

| Ex. | Structure | Data |
|---|---|---|
| 3 | 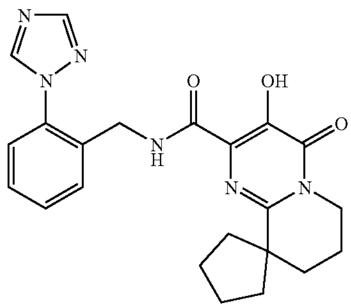 | Yield: 65%. ¹H NMR (500 MHz, CDCl$_3$) δ: 11.82 (1H, s), 8.80 (1H, t, J=6.1 Hz), 8.43 (1H, s), 8.15 (1H, s), 7.73 (1H, dd, J=7.3, 1.5 Hz), 7.52-7.44 (2H, m), 7.36 (1H, dd, J= 7.6, 1.2 Hz), 4.48 (2H, d, J=6.7 Hz), 3.99 (2H, t, J=6.4 Hz), 2.28-2.23 (2H, m), 1.99-1.91 (4H, m), 1.79-1.66 (6H, m). HRMS (M + H) calcd for C$_{22}$H$_{25}$N$_6$O$_3$: 421.1988; found: 421.2001. Anal calcd for C$_{22}$H$_{24}$N$_6$O$_3$: C, 62.84; H, 5.75; N, 19.98; found: C, 62.55; H, 5.68; N, 20.03. |
| 4 | 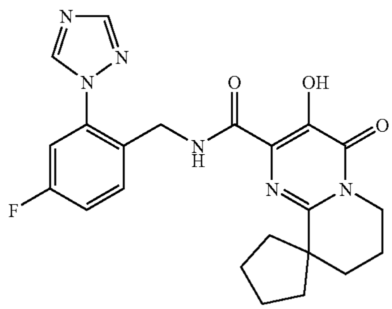 | Yield: 70%. ¹H NMR (500 MHz, CDCl$_3$) δ: 11.76 (0.6H, s), 11.69 (0.4H, s), 8.77 (0.6H, t, J=6.4 HZ), 8.68 (0.4H, t, J=6.4 Hz), 8.44 (0.6H, s), 8.39 (0.4H, s), 8.16 (0.6H, s), 8.15 (0.4H, s), 7.73 (0.H, dd, J=8.6, 6.1 Hz), 7.43 (0.4H, dd, J=8.6, 2.8 Hz), 7.34 (0.4H, dd, J=8.5, 4.9 Hz), 7.21 (0.6H, td, J= 8.2, 2.4 Hz), 7.15 (0.4H, td, J=8.5, 3.0 Hz), 7.11 (0.6H, dd, J=8.6 2.4 Hz), 4.45 (0.6H, d, J=6.7 Hz), 4.43 (0.4H, d, J=7.0 Hz), 4.04-3.98 (2H, m), 2.27-2.22 (2H, m), 1.98-1.91 (4H, m), 1.81-1.66 (6H, m). HRMS (M + H) calcd for C$_{22}$H$_{24}$FN$_6$O$_3$: 439.1894; found: 439.1887. Anal calcd for C$_{22}$H$_{23}$FN$_6$O$_3$: C, 60.26; H, 5.28; N, 19.16; found: C, 60.10; H, 5.42; N, 19.25. |
| 5 | 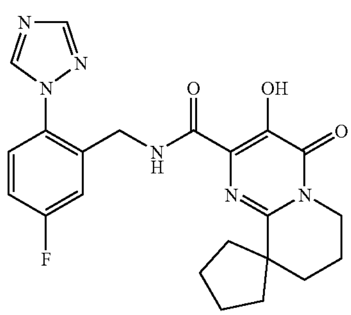 | Yield: 71%. ¹H NMR (500 MHz, CDCl$_3$) δ: 11.77 (0.6H, s), 11.70 (0.4H, s), 8.80 (0.6H, t, J=6.7 Hz), 8.70 (0.4H, t, J=6.4 Hz), 8.44 (0.6H, s), 8.39 (0.4H, s), 8.16 (0.6H, s), 8.15 (0.4H, s), 7.73 (0.6H, dd, J=8.5, 6.1 Hz), 7.43 (0.4H, dd, J=8.6, 2.8 Hz), 7.34 (0.4H, dd, J=8.9, 4.9 Hz), 7.21 (0.6H, td, J=8.2, 2.7 Hz), 7.15 (0.4H, td, J=8.6, 2.8 Hz), 7.11 (0.6H, dd, J=8.4, 2.6 Hz), 4.45 (0.6H, d, J=6.7 Hz), 4.43 (0.4H, d, J= 6.7 Hz), 4.01-3.98 (2H, m), 2.27-2.22 (2H, m), 1.98-1.92 (4H, m), 1.80-1.66 (6H, m). HRMS (M + H) calcd for C$_{22}$H$_{24}$FN$_6$O$_3$: 439.1894; found: 439.1875. Anal calcd for C$_{22}$H$_{23}$FN$_6$O$_3$: C, 60.26; H, 5.28; N, 19.16; found: C, 60.14; H, 5.38; N, 19.25. |
| 6 | 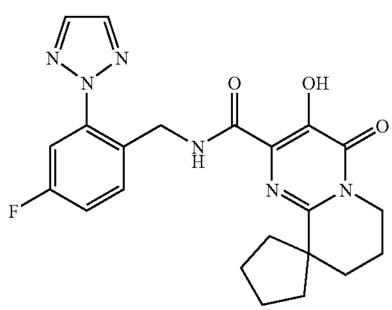 | Yield: 73%. ¹H NMR (500 MHz, CDCl$_3$) δ: 11.87 (1H, s), 8.91 (1H, t, J=6.7 Hz), 7.91 (2H, s), 7.69 (1H, dd, J=8.5, 5.8 Hz), 7.63 (1H, dd, J=9.3, 2.6 Hz), 7.13 (1H, td, J= 8.2, 2.6 Hz), 4.64 (2H, d, J=7.0 Hz), 3.99 (2H, t, J=6.4 Hz), 2.23-2.17 (2H, m), 1.97-1.85(4H, m), 1.78-1.63 (6H, m). HRMS (M + H) calcd for C$_{22}$H$_{24}$FN$_6$O$_3$: 439.1894; found: 439.1912. Anal calcd for C$_{22}$H$_{23}$FN$_6$O$_3$: C, 60.26; H, 5.28; N, 19.16; found: C, 59.97; H, 4.99; N, 19.03. |

TABLE 3-continued

| Ex. | Structure | Data |
|---|---|---|
| 7 | 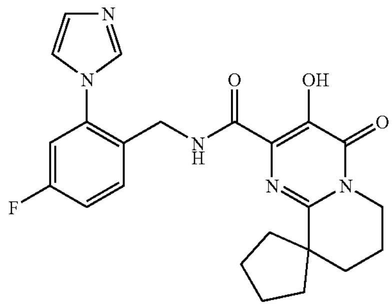 | Yield: 63%. $^1$H NMR (500 MHz, CDCl$_3$) δ: 13.02 (1H, br s), 8.82 (1H, s), 7.98 (1H, t, J= 5.2 Hz), 7.60-7.57 (2H, m), 7.47 (1H, s), 7.33 (1H, td, J=7.6, 1.8 Hz), 7.13 (1H, d, J= 7.3 Hz), 4.39 (2H, d, J=5.8 Hz), 3.99 (2H, t, J=6.4 Hz), 2.16-2.10 (2H, m), 1.99-1.94 (2H, m), 1.86-1.67 (8H, m). HRMS (M + H) calcd for C$_{23}$H$_{25}$FN$_5$O$_3$: 438.1941; found: 438.1954. Anal calcd for C$_{23}$H$_{24}$FN$_5$O$_3$·0.3 EtOAc: C, 50.92; H, 4.37; N, 10.84; found: C, 50.59; H, 4.14; N, 10.95. |
| 8 | 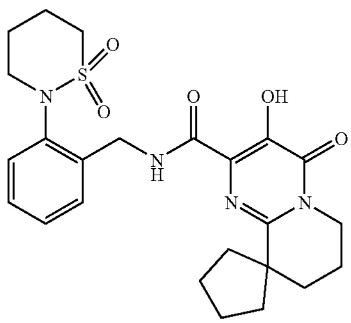 | Yield: 77%. $^1$H NMR (500 MHz, CDCl$_3$) δ: 11.90 (1H, s), 8.22-8.20 (1H, m), 7.47-7.43 (2H, m), 7.36-7.32 (2H, m), 4.98 (1H, dd, J= 14.3, 8.5 Hz), 4.46 (1H, dd, J=14.3, 4.0 Hz), 3.99 (2H, td, J=6.2, 1.8 Hz), 3.90-3.85 (1H, m), 3.44-3.39 (1H, m), 3.25-3.22 (2H, m), 2.44-2.30 (2H, m), 2.23-2.15 (2H, m), 1.97-1.89 (4H, m), 1.85-1.80 (2H, m), 1.73-1.58 (6H, m). HRMS (M + H) calcd for C$_{24}$H$_{31}$N$_4$O$_5$S: 487.2015; found: 487.2030. Anal calcd for C$_{24}$H$_{30}$N$_4$O$_5$S: C, 59.24; H, 6.21; N, 11.51; found: C, 58.94; H, 6.47; N, 11.43. |
| 9 | 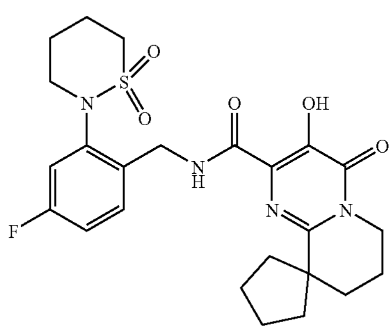 | Yield: 70%. $^1$H NMR (500 MHz, CDCl$_3$) δ: 11.85 (1H, s), 8.22-8.19 (1H, m), 7.46 (1H, dd, J=8.6, 6.4 Hz), 7.16 (1H, dd, J=9.2, 2.5 Hz), 7.06 (1H, td, J=8.2, 2.8 Hz), 4.95 (1H, dd, J=14.3, 8.9 Hz), 4.39 (1H, dd, J= 14.3, 4.0 Hz), 3.99 (2H, td, J=6.4, 1.8 Hz), 3.86-3.81 (1H, m), 3.43-3.39 (1H, m), 3.25-3.23 (2H, m), 2.44-2.30 (2H, m), 2.22-2.14 (2H, m), 1.98-1.90 (4H, m), 1.85-1.80 (2H, m), 1.74-1.58 (6H, m). HRMS (M + H) calcd for C$_{24}$H$_{30}$FN$_4$O$_5$S: 505.1921; found: 505.1942. Anal calcd for C$_{24}$H$_{29}$FN$_4$O$_5$S: C, 57.13; H, 5.79; N, 11.10; found: C, 57.01; H, 5.98; N, 11.02. |
| 10 | 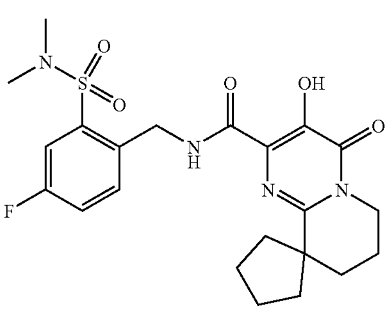 | Yield: 66%. $^1$H NMR (500 MHz, CDCl$_3$) δ: 11.65 (1H, br s), 8.60 (1H, t, J=6.7 Hz), 7.69 (1H, dd, J=8.4, 5.4 Hz), 7.49 (1H, dd, J=8.4, 2.6 Hz), 7.28-7.24 (1H, m), 4.81 (2H, d, J=6.7 Hz), 3.98 (2H, t, J=6.4 Hz), 2.89 (6H, s), 2.22-2.16 (2H, m), 1.96-1.91 (4H, m), 1.76-1.61 (6H, m). HRMS (M + H) calcd for C$_{22}$H$_{28}$FN$_4$O$_5$S: 479.1764; found: 479.1788. Anal calcd for C$_{22}$H$_{27}$FN$_4$O$_5$S·0.8 H$_2$O: C, 53.60; H, 5.85; N, 11.37; found: C, 53.48; H, 5.50; N, 10.98. |
| 11 | 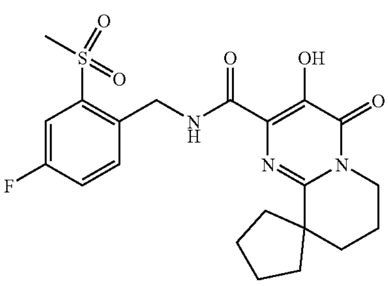 | Yield: 53%. $^1$H NMR (500 MHz, CDCl$_3$) δ: 11.54 (1H, s), 8.56 (1H, t, J=6.4 Hz), 7.74 (1H, dd, J=8.1, 2.6 Hz), 7.71 (1H, dd, J= 8.6, 5.2 Hz), 7.33 (1H, td, J=8.1, 2.8 Hz), 4.83 (2H, d, J=7.0 Hz), 3.97 (2H, t, J=6.4 Hz), 3.16 (3H, s), 2.20-2.15 (2H, m), 1.96-1.91 (4H, m), 1.76-1.62 (6H, m). HRMS (M + H) calcd for C$_{21}$H$_{25}$FN$_3$O$_5$S: 450.1499; found: 450.1479. Anal calcd for C$_{21}$H$_{24}$FN$_3$O$_5$S: C, 56.11; H, 5.38; N, 9.34; found: C, 55.89; H, 5.39; N, 9.19. |

TABLE 3-continued

| Ex. | Structure | Data |
|---|---|---|
| 12 | 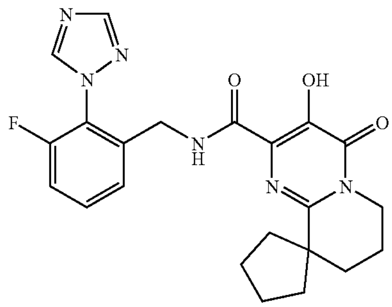 | Yield: 66%. ¹H NMR (500 MHz, CDCl₃) δ: 11.73 (1H, s), 8.71 (1H, t, J=6.4 Hz), 8.45 (1H, d, J=3.4 Hz); 8.18 (1H, s), 7.51 (1H, d, J=7.6 Hz), 7.48-7.43 (1H, m), 7.27-7.23 (1H, m), 4.43 (2H, d, J=6.7 Hz), 3.99 (2H, t, J=6.4 Hz), 2.28-2.22 (2H, m), 2.00-1.92 (4H, m), 1.81-1.74 (4H, m), 1.72-1.67 (2H, m). HRMS (M + H) calcd for $C_{22}H_{24}FN_6O_3$: 439.1894; found: 439.1883. Anal cacld for $C_{22}H_{23}FN_6O_3$: C, 60.26; H, 5.28; N, 19.16; found: C, 60.06; H, 5.22; N, 19.09. |
| 13 | 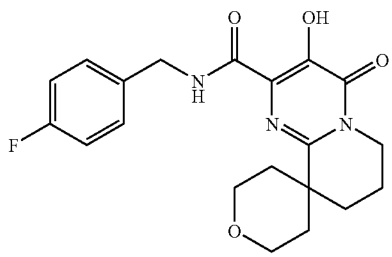 | Yield: 59%. ¹H NMR (500 MHz, CDCl₃) δ: 11.90 (1H, s), 7.93 (1H, br t), 7.34-7.32 (2H, m), 7.05 (2H, t, J=8.5 Hz), 4.60 (2H, d, J=6.4 Hz), 3.99 (2H, t, J=6.4 Hz), 3.90-3.90 (2H, m), 3.65 (2H, dt=11.9, 1.5 Hz), 2.38 (2H, dt, J=13.5, 3.7 Hz), 2.03-1.94 (4H, m), 1.52 (2H, d, J=13.7 Hz). HRMS (M − H) calcd for $C_{20}H_{21}FN_3O_4$: 386.1516; found: 386.1499. Anal calcd for $C_{20}H_{22}FN_3O_4 \cdot 0.04\ H_2O \cdot 0.2$ TFA: C, 64.79; H, 6.24; N, 10.77; found: C, 64.71; H, 6.31; N, 10.71. |
| 14 | 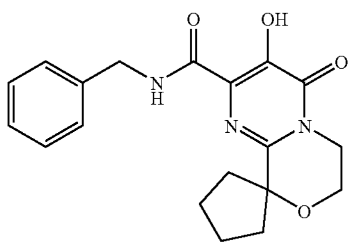 | Yield: 79%. ¹H NMR (500 MHz, CDCl₃) δ: 12.01 (1H, s), 7.78 (1H, br t), 7.39-7.30 (5H, m), 4.63 (2H, d, J=6.4 Hz), 4.03-3.96 (4H, m), 2.16-2.04 (4H, m), 1.86-1.79 (4H, m). HRMS (M + H) calcd for $C_{19}H_{22}N_3O_4$: 356.1610; found: 356.1616. Anal calcd for $C_{19}H_{21}N_3O_4$: C, 64.21; H, 5.95; N, 11.82; found: C, 63.98; H, 5.81; N, 11.71. |
| 15 | 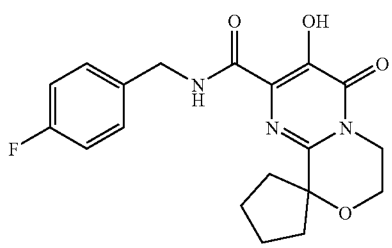 | Yield: 85%. ¹H NMR (500 MHz, CDCl₃) δ: 11.92 (1H, s), 7.75 (1H, brt), 7.30 (2H, dd, J=8.5, 5.5 Hz), 7.04 (2H, t, J=8.5 Hz), 4.58 (2H, d, J=6.4 Hz), 4.02-3.95 (4H, m), 2.15-2.04 (4H, m), 1.88-1.79 (4H, m). HRMS (M + H) calcd for $C_{19}H_{21}FN_3O_4$: 374.1516; found: 374.1506. Anal calcd for $C_{19}H_{20}FN_3O_4 \cdot 0.15\ H_2O$: C, 60.09; H, 5.37; N, 11.01; F, 5.72; found: C, 59.87; H, 5.24; N, 10.90; F, 5.53. |
| 16 | 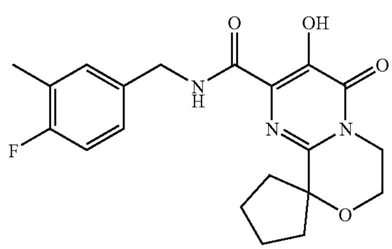 | Yield: 67%. ¹H NMR (500 MHz, CDCl₃) δ: 11.95 (1H, s), 7.72 (1H, brt), 7.14 (1H, d, J= 7.0 Hz), 7.11-7.08 (1H, m), 6.98 (1H, t, J= 9.0 Hz), 4.54 (2H, d, J=6.4 Hz), 4.03-3.95 (4H, m), 2.27 (3H, s), 2.16-2.03 (4H, m), 1.88-1.79 (4H, m). HRMS (M + H) calcd for $C_{20}H_{23}FN_3O_4$: 388.1673; found: 388.1661. |
| 17 | 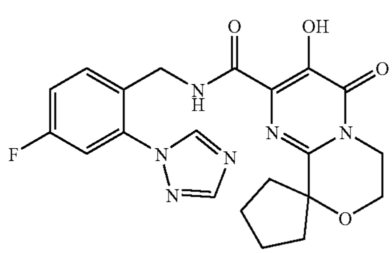 | Yield: 51%. ¹H NMR (500 MHz, CDCl₃) δ: 11.90 (1H, s), 8.76 (1H, t, J=6.4 Hz), 8.44 (1H, s), 8.13 (1H, s), 7.70 (1H, dd, J=8.5, 6.1 Hz), 7.21 (1H, td, J=8.2, 2.4 Hz), 7.11 (1H, dd, J=8.4, 2.6 Hz), 4.44 (2H, d, J= 6.7 Hz), 4.01-3.94 (4H, m), 2.27-2.21 (2H, m), 2.09-2.04 (2H, m), 1.93-1.88 (4H, m). HRMS (M + H) calcd for $C_{21}H_{22}FN_6O_4$: 441.1687; found: 441.1691. Anal calcd for $C_{21}H_{21}FN_6O_4$: N, 19.08; F, 4.31; found: N, 19.37; F, 4.56. |

TABLE 3-continued

| Ex. | Structure | Data |
|---|---|---|
| 18 | 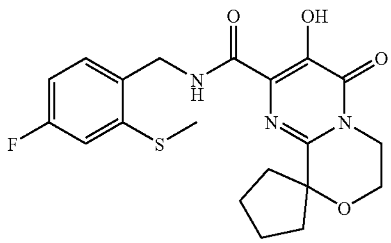 | Yield: 77%. ¹H NMR (500 MHz, CDCl₃) δ: 11.84 (1H, s), 8.08 (1H, t, J=5.2 Hz), 7.30 (1H, dd, J=8.4, 6.0 Hz), 6.95 (1H, dd, J=9.5, 2.7 Hz), 6.83 (1H, td, J=8.2, 2.8 Hz), 4.60 (2H, d, J=6.4 Hz), 4.01-3.94 (4H, m), 2.51 (3H, s), 2.20-2.14 (2H, m), 2.08-2.03 (2H, m), 1.88-1.82 (4H, m). HRMS (M + H) calcd for C₂₀H₂₃FN₃O₃S: 420.1393; found: 420.1383. Anal calcd for C₂₀H₂₂FN₃O₃S: C, 57.26; H, 5.28; N, 10.01; F, 4.52; found: C, 57.27; H, 5.31; N, 10.01; F, 4.49. |
| 19 | 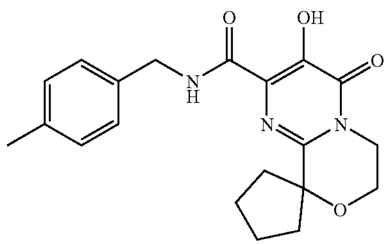 | Yield: 83%. ¹H NMR (500 MHz, CDCl₃) δ: 12.04 (1H, s) 7.74 (1H, br t), 7.22 (2H, d, J=7.9 Hz), 7.18 (2H, d, J=7.9 Hz), 4.58 (2H, d, J=6.1 Hz), 4.03-3.95 (4H, m), 2.35 (3H, s), 2.15-2.03 (4H, m), 1.87-1.79 (4H, m). HRMS (M + H) calcd for C₂₀H₂₄N₃O₄: 370.1767; found: 370.1778. Anal calcd for C₂₀H₂₃N₃O₄: C, 65.02; H, 6.27; N, 11.37; found: C, 64.93; H, 6.44; N, 11.32. |
| 20 | 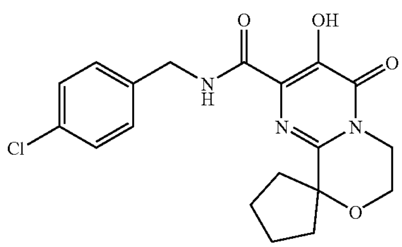 | Yield: 75%. ¹H NMR (500 MHz, CDCl₃) δ: 11.90 (1H, s), 7.76 (1H, t, J=5.4 Hz), 7.34 (2H, d, J=7.9 Hz), 7.26 (2H, d, J=7.9 Hz), 4.59 (2H, d, J=6.4 Hz), 4.03-3.96 (4H, m), 2.16-2.04 (4H, m), 1.89-1.79 (4H, m). HRMS (M + H) calcd for C₁₉H₂₁ClN₃O₄: 3901221; found: 390-1216. Anal calcd for C₁₉H₂₀ClN₃O₄: C, 58.54; H, 5.17; N, 10.77; found: C, 58.34; H, 5.24; N, 10.59. |
| 21 | 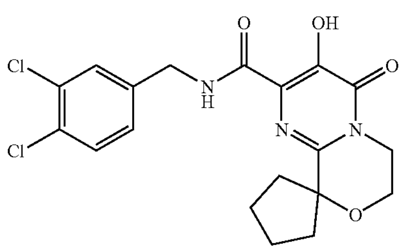 | Yield: 73%. ¹H NMR (500 MHz, CDCl₃) δ: 11.81 (1H, s), 7.79 (1H, t, J=5.4 Hz), 7.43 (1H, d, J=8.2 Hz), 7.41 (1H, d, J=1.5 Hz), 7.17 (1H, dd, J=8.2, 1.5 Hz), 4.57 (2H, d, J=6.4 Hz), 4.03-3.96 (4H, m), 2.17-2.05 (4H, m), 1.90-1.81 (4H, m). HRMS (M + H) calcd for C₁₉H₂₀Cl₂N₃O₄: 424.0831; found: 424.0811. |
| 22 | 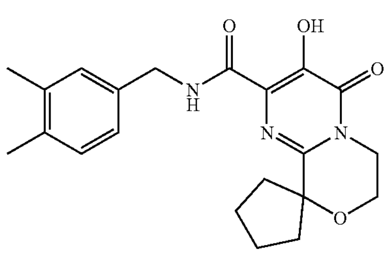 | Yield: 85%. ¹H NMR (500 MHz, CDCl₃) δ: 12.06 (1H, s), 7.74 (1H, br t), 7.13 (1H, d, J=7.6 Hz), 7.09 (1H, s), 7.05 (1H, d, J=7.6 Hz), 4.56 (2H, d, J=6.1 Hz), 4.03-3.95 (4H, m), 2.26 (6H, s), 2.16-2.03 (4H, m), 1.87-1.80 (4H, m). HRMS (M + H) calcd for C₂₁H₂₆N₃O₄: 384.1923; found: 384.1937. Anal calcd for C₂₁H₂₅N₃O₄: C, 65.78; H, 6.57; N, 10.95; found: C, 65.58; H, 6.58; N, 10.89. |
| 23 | 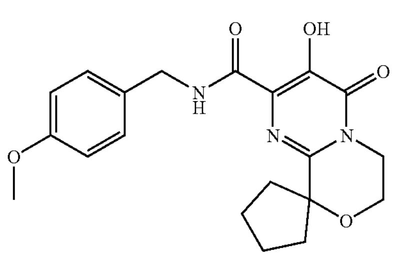 | Yield: 84%. ¹H NMR (500 MHz, CDCl₃) δ: 12.04 (1H, s), 7.71 (1H, br t), 7.26 (2H, d, J=8.6 Hz), 6.90 (2H, d, J=8.6 Hz), 4.55 (2H, d, J=6.4 Hz), 4.03-3.95 (4H, m), 3.81 (3H, s), 2.15-2.03 (4H, m), 1.87-1.79 (4H, m). HRMS (M + H) calcd for C₂₀H₂₄N₃O₅: 386.1716; found: 386.1697. Anal calcd for C₂₀H₂₃N₃O₅.0.11 CH₂Cl₂: C, 61.19; H, 5.93; N, 10.64; found: C, 60.86; H, 5.98; N, 10.55. |

TABLE 3-continued

| Ex. | Structure | Data |
|---|---|---|
| 24 | 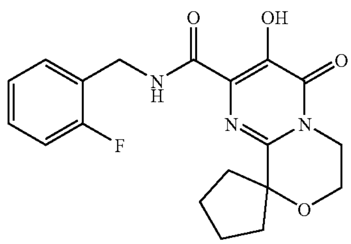 | Yield: 78%. ¹H NMR (500 MHz, CDCl₃) δ: 11.89 (1H, s), 7.88 (1H, t, J=5.2 Hz), 7.37 (1H, td, J=7.6 1.2 Hz), 7.33-7.28 (1H, m), 7.14 (1H, t, J=7.6 Hz), 7.09 (1H, t, J=9.3 Hz), 4.66 (2H, d, J=6.4 Hz), 4.03-3.95 (4H, m), 2.19-2.13 (2H, m), 2.09-2.04 (2H, m), 1.89-1.83 (4H, m). HRMS (M + H) calcd for C₁₉H₂₁FN₃O₄: 374.1516; found: 374.1532. Anal calcd for C₁₉H₂₀FN₃O₄.0.05 Et₂O.0.05 CH₂Cl₂: C, 60.63; H, 5.45; N, 11.02; found: C, 60.58; H, 5.33; N, 11.03. |
| 25 | 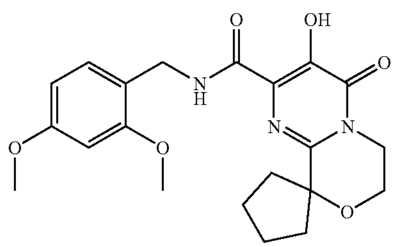 | Yield: 88%. ¹H NMR (500 MHz, CDCl₃) δ: 12.10 (1H, s), 8.06 (1H, t, J=5.6 Hz), 7.20 (1H, d, J=8.2 Hz), 6.48 (1H, d, J=2.4 Hz), 6.45 (1H, dd, J=8.2, 2.4 Hz), 4.51 (2H, d, J=6.4 Hz), 4.01-3.95 (4H, m), 3.85 (3H, s), 3.80 (3H, s), 2.20-2.14 (2H, m), 2.09-2.04 (2H, m), 1.91-1.83 (4H, m). HRMS (M + H) calcd for C₂₁H₂₆N₃O₆: 416.1822; found: 416.1837. Anal calcd for C₂₁H₂₅N₃O₆: C, 60.71; H, 6.06; N, 10.11; found: C, 60.47; H, 6.10; N, 9.97. |
| 26 | 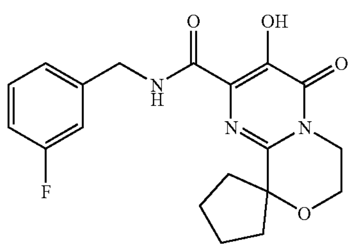 | Yield: 86%. ¹H NMR (500 MHz, CDCl₃) δ: 11.89 (1H, s), 7.80 (1H, br t), 7.34 (1H, q, J= 7.6 Hz), 7.10 (1H, d, J=7.6 Hz), 7.03-6.98 (2H, m), 4.62 (2H, d, J=6.4 Hz), 4.04-3.96 (4H, m), 2.17-2.05 (4H, m), 1.88-1.81 (4H, m). HRMS (M + H) calcd for C₁₉H₂₁FN₃O₄: 374.1516; found: 374.1504. Anal calcd for C₁₉H₂₀FN₃O₄.0.1 CH₂Cl₂: C, 60.07; H, 5.33; N, 11.00; found: C, 60.06; H, 5.39; N, 10.94. |
| 27 | 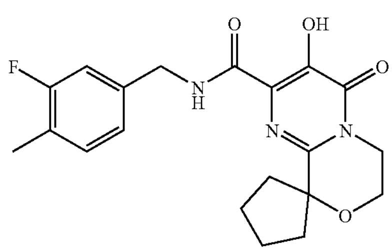 | Yield: 65%. ¹H NMR (500 MHz, CDCl₃) δ: 11.93 (1H, s), 7.76 (1H, br t), 7.17 (1H, t, J= 7.9 Hz), 6.99 (1H, d, J=7.9 Hz), 6.97 (1H, d, J=10.4 Hz), 4.57 (2H, d, J=6.4 Hz), 4.03-3.96 (4H, m), 2.26 (3H, s), 2.17-2.05 (4H, m), 1.88-1.80 (4H, m). HRMS (M + H) calcd for C₂₀H₂₃FN₃O₄: 388.1673; found: 388.1665. Anal calcd for C₂₀H₂₂FN₃O₄: C, 62.00; H, 5.72; N, 10.84; found: C, 61.73; H, 7.72; N, 10.66. |
| 28 | 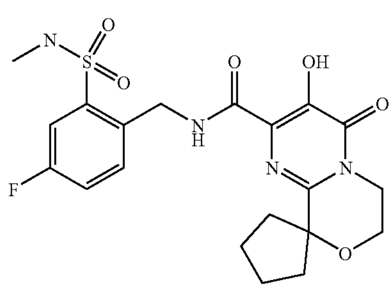 | Yield: 44%. ¹H NMR (500 MHz, CDCl₃) δ: 11.80 (1H, br s), 8.61 (1H, t, J=6.7 Hz), 7.68 (1H, dd, J=8.6, 5.2 Hz), 7.48 (1H, dd, J=8.4, 2.6 Hz), 7.28-7.24 (1H, m), 4.80 (2H, d, J=7.0 Hz), 4.00-3.94 (4H, m), 2.90 (6H, s), 2.24-2.18 (2H, m), 2.06-2.00 (2H, m), 1.96-1.80 (4H, m). HRMS (M + H) calcd for C₂₁H₂₆FN₄O₆S: 481.1557; found: 481.1561. Anal calcd for C₂₁H₂₅FN₄O₆S. 0.35 CF₃CO₂H. 0.1 C₄H₁₀O: C, 50.29; H, 5.03; N, 10.61; found: C, 50.06; H, 4.70; N, 10.51. |
| 29 | 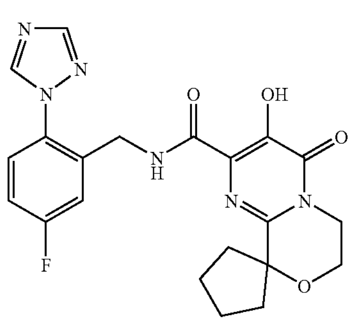 | Yield: 51%. ¹H NMR (500 MHz, CDCl₃) δ: 11.84 (1H, s), 8.67 (1H, t, J=5.8 Hz), 8.39 (1H, s), 8.13 (s, 1H), 7.42 (1H, dd, J=8.4, 2.9 Hz) 7.34 (1H, dd, J=8.7, 4.2 Hz), 7.16 (1H, td, J=8.1, 2.8 Hz), 4.42 (2H, d, J= 6.7 Hz), 4.02-3.96 (4H, m), 2.28-2.22 (2H, m), 2.10-2.05 (2H, m), 1.94-1.88 (4H, m). HRMS (M + H) calcd for C₂₁H₂₂FN₆O₄: 441.1687; found: 441.1697. Anal calcd for C₂₁H₂₁FN₆O₄: C, 57.26; H, 4.80; N, 19.08; found: C, 57.27; H, 4.85; N, 19.07. |

TABLE 3-continued

| Ex. | Structure | Data |
|---|---|---|
| 30 | [structure] | Yield: 87%. $^1$H NMR (500 MHz, CDCl$_3$) δ: 11.92 (1H, s), 7.41 (1H, br t), 7.20-7.17 (2H, m), 7.03-7.00 (2H, m), 4.01-3.99 (2H, m), 3.96-3.94 (2H, m), 3.68 (2H, q, J=6.7 Hz), 2.89 (2H, t, J=6.7 Hz), 2.06-1.97 (4H, m), 1.88-1.80 (2H, m), 1.77-1.69 (2H, m). HRMS (M + H) calcd for C$_{20}$H$_{23}$FN$_3$O$_4$: 388.1673; found: 388.1680. Anal calcd for C$_{20}$H$_{22}$FN$_3$O$_4$·0.8 H$_2$O: C, 60.05; H, 5.90; N, 10.50; found: 0, 60.14; H, 5.60; N, 10.51. |
| 31 | [structure] | Yield: 80%. $^1$H NMR (500 MHz, CDCl$_3$) δ: 12.03 (1H, s), 7.44 (1H, br t), 7.16-7.13 (2H, m), 6.99-6.95 (2H, m), 4.03-4.01 (2H, m), 3.98-3.96 (2H, m), 3.44 (2H, q, J=6.7 Hz), 2.68 (2H, t, J=7.6 Hz), 2.18-2.06 (4H, m), 1.97-1.84 (6H, m). HRMS (M + H) calcd for C$_{21}$H$_{25}$FN$_3$O$_4$: 402.1829; found: 402.1840. Anal calcd for C$_{21}$H$_{24}$FN$_3$O$_4$: C, 62.83; H, 6.02; N, 10.46; found: C, 62.46; H, 6.26; N, 10.52. |
| 32 | [structure] | Yield: 73%. $^1$H NMR (500 MHz, CDCl$_3$) δ: 12.10 (1H, s), 8.55 (1H, t, J=6.4 Hz), 8.29 (1H, s), 7.68 (1H, dd, J=8.6, 6.1Hz), 7.17 (1H, td, J=8.6, 2.8 Hz), 7.08 (1H, dd, J=8.6, 2.8 Hz), 4.47 (2H, d, J=6.7 Hz), 4.02-4.00 (2H, m), 3.96-3.94 (2H, m), 2.52 (3H, s), 2.23-2.16 (2H, m), 2.09-2.04 (2H, m), 1.88-1.83 (4H, m). HRMS (M + H) calcd for C$_{22}$H$_{24}$FN$_6$O$_4$: 455.1843; found: 455.1850. Anal calcd for C$_{22}$H$_{23}$FN$_6$O$_4$: C, 58.14; H, 5.10; N, 18.49; found: C, 58.04; H, 4.98; N, 18.53. |
| 33 | [structure] | Yield: 10%. $^1$H-NMR (300 MHz, CDCl$_3$) δ: 11.95 (1H, s), 8.84-8.79 (1H, m), 8.41 (1H, s), 8.11 (1H, s), 7.68 (1H, dd, J=6.8, 2.0 Hz), 7.51-7.42 (2H, m), 7.33 (1H, dd, J=7.3, 1.8 Hz), 4.44 (2H, d, J=7.0 Hz), 3.99-3.92 (4H, m), 2.27-2.18 (2H, m), 2.08-2.00 (2H, m), 1.92-1.85 (4H, m). HRMS [M + H]$^+$ calcd for C$_{21}$H$_{23}$N$_6$O$_4$: 423.1781; found: 423.1773. |
| 34 | [structure] | Yield: 59% yield. $^1$H-NMR (300 MHz, CDCl$_3$) δ: 11.83 (1H, br s), 8.26-8.22 (1H, m), 7.43 (1H, dd, J=8.8, 6,2 Hz), 7.15 (1H, dd, J=9.1,2.6 Hz), 7.04 (1H, dt, J=8.2, 2.6 Hz), 4.91 (1H, dd, J=14.1, 9.0 Hz), 4.34 (1H, dd, J=14.3, 3.7 Hz), 3.99-3.89 (4H, m), 3.86-3.77 (1H, m), 3.44-3.36 (1H, m), 3.23-3.19 (2H, m), 2.40-2.30 (2H, m), 2.21-2.10 (2H, m), 2.01-1.89 (4H, m), 1.83-1.74 (4H, m). HRMS [M + H]$^+$ calcd for C$_{23}$H$_{28}$N$_4$O$_6$FS: 507.1714; found: 507.1735. Anal calcd for C$_{23}$H$_{27}$N$_4$O$_6$FS: C, 54.54; H, 5.37; N, 11.06; S, 6.33; F, 3.75; found: C, 54.27; H, 5.22; N, 11.01; S, 6.14; F, 3.81. |

TABLE 3-continued

| Ex. | Structure | Data |
|---|---|---|
| 35 | 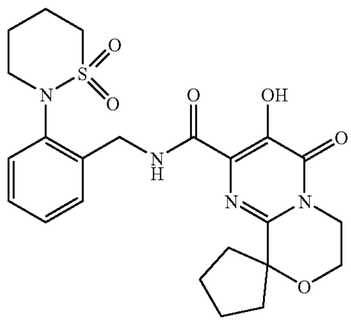 | Yield: 81% yield. $^1$H-NMR (300 MHz, CDCl$_3$) δ: 12.08 (1H, s), 8.27-8.23 (1H, m), 7.46-7.41 (2H, m), 7.35-7.32 (2H, m), 4.93 (1H, dd, J=14.1, 9.0 Hz), 4.40 (1H, dd, J= 14.1, 3.5 Hz), 4.00-3.96 (2H, m), 3.93-3.88 (2H, m), 3.86-3.81 (1H, m), 3.44-3.36 (1H, m), 3.22-3.18 (2H, m), 2.41-2.28 (2H, m), 2.21-2.11 (2H, m), 2.02-1.89 (4H, m), 1.84-1.74 (4H, m). HRMS [M + H]$^+$ calcd for C$_{23}$H$_{29}$N$_4$O$_6$S: 489.1808; found: 489.1801. Anal calcd for C$_{23}$H$_{28}$N$_4$O$_6$S: C, 56.54; H, 5.78; N, 11.47; found: C, 56.63; H, 5.48; N, 11.37. |
| 36 | 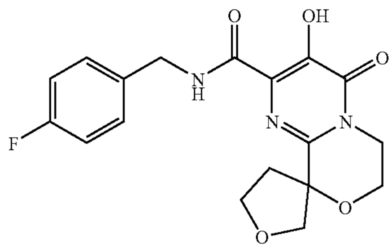 | Yield: 65%. $^1$H NMR (500 MHz, CDCl$_3$) δ: 12.10 (1H, s), 7.74 (1H, br t), 7.30 (2H, dd, J=8.5, 5.2 Hz), 7.04 (2H, t, J=8.5 Hz), 4.62-4.53 (2H, m), 4.14-3.99 (8H, m), 2.51-2.45 (1H, m), 2.36-2.31 (1H, m). HRMS (M + H) calcd for C$_{18}$H$_{19}$FN$_3$O$_5$;; found:. Anal calcd for C$_{18}$H$_{18}$FN$_3$O$_5$: C, 57.59; H, 4.83; N, 11.19; F, 5.06; found: C, 57.95; H, 4.96; N, 10.95; F, 5.43. |
| 37 | 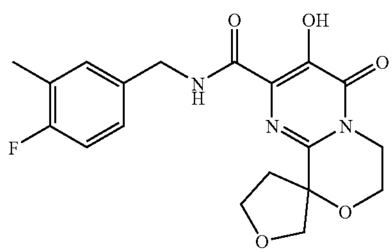 | Yield: 68%. $^1$H NMR (500 MHz, CDCl$_3$) δ: 12.13 (1H, s), 7.71 (1H, br t), 7.14-7.08 (2H, m), 6.97 (1H, t, J=8.8 Hz), 4.57-4.49 (2H, m), 4.14-3.99 (8H, m), 2.51-2.44 (1H, m), 2.36-2.31 (1H, m), 2.27 (3H, s). HRMS (M + H) calcd for C$_{19}$H$_{21}$FN$_3$O$_5$: 390.1465; found: 390.1451. Anal calcd for C$_{19}$H$_{20}$FN$_3$O$_5$: C, 58.60; H, 5.17; N, 10.79; F, 4.87; found: C, 58.62; H, 5.36; N, 10.77; F, 4.95. |
| 38 | 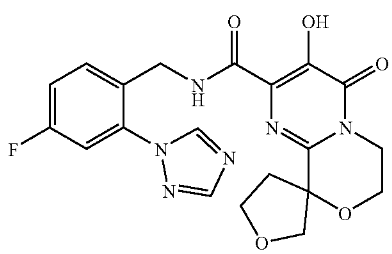 | Yield: 52%. $^1$H NMR (500 MHz, CDCl$_3$) δ: 11.908 (1H, s), 8.92 (1H, br t), 8.43 (1H, s), 8.26 (1H, s), 7.69 (1H, dd, J=8.5, 5.8 Hz), 7.21 (1H, td, J=8.2, 2.4 Hz), 7.10 (1H, dd, J=8.5, 2.4 Hz), 4.51-4.35 (2H, m), 4.26-3.97 (8H, m), 2.59-2.53 (1H, m), 2.36-2.31 (1H, m). HRMS (M + H) calcd for C$_{20}$H$_{20}$FN$_6$O$_5$: 443.1479; found: 443.1495. Anal calcd for C$_{20}$H$_{19}$FN$_6$O$_5$: C, 54.29; H, 4.32; N, 18.99; F, 4.29; found: C, 54.26; H, 4.44; N, 19.01; F, 4.38. |
| 39 | 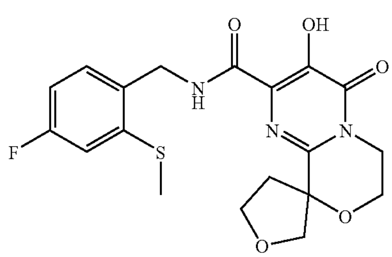 | Yield: 63%. $^1$H NMR (500 MHz, CDCl$_3$) δ: 12.01 (1H, s), 8.03 (1H, br t), 7.30-7.24 (1H, m), 6.99-6.94 (1H, m), 6.87-6.81 (1H, m), 4.64-4.59 (2H, m), 4.14-3.99 (8H, m), 2.55-2.51 (1H, m), 2.51 (3H, s), 2.38-2.31 (1H, m). HRMS (M + H) calcd for C$_{19}$H$_{21}$FN$_3$O$_5$S: 422.1186; found: 422.1165. Anal calcd for C$_{19}$H$_{21}$FN$_3$O$_5$S: C, 54.14; H, 4.78; N, 9.97; found: C, 54.22; H, 5.07; N, 9.90. |

TABLE 3-continued

| Ex. | Structure | Data |
|---|---|---|
| 40 | 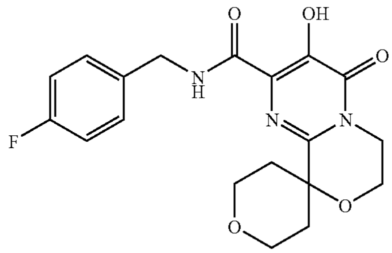 | Yield: 28%. $^1$H-NMR (500 MHz, CDCl$_3$) δ: 12.07 (1H, s), 7.81 (1H, t, J=6.0 Hz), 7.32 (2H, dd, J=8.5, 5.5 Hz), 7.06 (2H, t, J= 8.7 Hz), 4.58 (2H, d, J=6.4 Hz), 4.05-4.01 (4H, m), 3.84 (2H, dd, J=11.4, 5.3 Hz), 3.77 (2H, t, J=11.3 Hz), 2.30 (2H, dt, J= 13.3, 5.2 Hz), 1.79 (2H, d, J=13.7 Hz). ). HRMS [M + H] calcd for C$_{19}$H$_{21}$N$_3$O$_5$F: 390.14653; found: 390.1465. Anal clad for C$_{19}$H$_{20}$N$_3$O$_5$F: C, 58.60; H, 5.17; N, 10.79; F, 4.87; found: 0, 58.70; H, 5.26; N, 10.80; F, 4.99. |
| 41 | 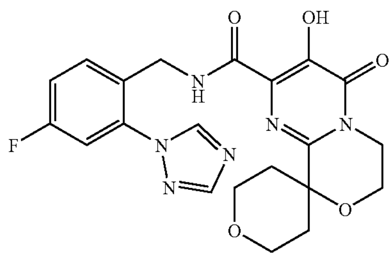 | Yield: 30%. $^1$H-NMR (500 MHz, CDCl$_3$) δ: 11.86 (1H, s), 9.12 (1H, t, J=5.6 Hz), 8.46 (1H, s), 8.39 (1H, s), 7.68 (1H, dd, J=8.2, 6.1 Hz), 7.21 (1H, dt, J=8.2, 2.1 Hz), 7.10 (1H, dd, J=8.4, 2.0 Hz), 4.45 (2H, dd, J= 6.7 Hz), 4.02 (4H, s), 3.90 (2H, dd, J= 11.3, 4.6 Hz), 3.79 (2H, t, J=11.7 Hz), 2.44 (2H, dt, J=13.1, 4.9 Hz), 1.80 (2H, d, J=13.4 Hz). HRMS (M + H) calcd for C$_{21}$H$_{22}$N$_6$O$_5$F: 457.16358; found: 457.1639. Anal calcd for C$_{21}$H$_{21}$N$_6$O$_5$F: C, 55.26; H, 4.63; N, 18.41; F, 4.16; found: C, 54.99; H, 4.54; N, 18.38; F, 4.08. |
| 42 | 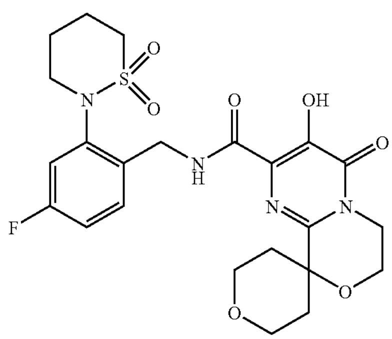 | Yield: 53%. $^1$H-NMR (500 MHz, CDCl$_3$) δ: 12.12 (1H, s), 8.25-8.23 (1H, m), 7.48 (1H, q, J=8.5, 6.1 Hz), 7.21 (1H, dd, J=9.0, 2.6 Hz), 7.08 (1H, dt, J=8.2, 2.5 Hz), 4.90 (1H, dd, J=14.2, 8.4 Hz), 4.43 (1H, dd, J= 14.0, 4.3 Hz), 4.01 (4H, s), 3.86-3.71 (4H, m), 3.45-3.42 (1H, m), 3.32 (1H, dt, J= 13.2, 4.4 Hz), 3.28-3.22 (1H, m), 2.47-2.29 (4H, m), 2.00-1.93 (2H, m), 1.72 (2H, t, J= 15.2 Hz). HRMS [M + H]$^+$ calcd for C$_{23}$H$_{28}$N$_6$O$_7$FS: 523.1663; found: 523.1666. Anal calcd for C$_{23}$H$_{27}$N$_6$O$_7$FS.0.5 H$_2$O: C, 51.97; H, 5.31; N, 10.54; F, 3.57; S, 6.03; found: C, 51.84; H, 4.96; N, 10.28; F, 3.62; S, 6.01. |
| 43 | 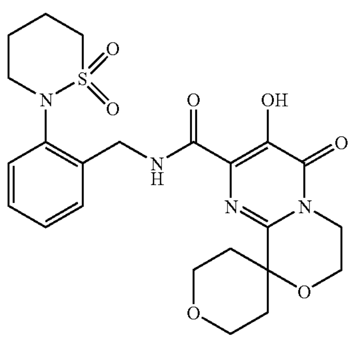 | Yield: 65%. $^1$H-NMR (300 MHz, CDCl$_3$/1drop MeOD) δ: 8.28-8.24 (1H, m), 7.46-7.43 (2H, m), 7.35-7.32 (2H, m), 4.89 (1H, dd, J=14.3, 8.4 Hz), 4.45 (1H, dd, J= 14.3, 4.4 Hz), 3.97 (4H, s), 3.89-3.65 (5H, m), 3.43-3.36 (1H, m), 3.33-3.16 (2H, m), 2.46-2.24 (4H, m), 1.96-1.88 (2H, m), 1.73-1.65 (2H, m). HRMS [M + H]$^+$ calcd for C$_{23}$H$_{29}$N$_4$O$_7$S: 505.1757; found: 505.1761. Anal calcd for C$_{23}$H$_{28}$N$_4$O$_7$S: C, 54.75; H, 5.59; N, 11.10; S, 6.35; found: C, 55.03; H, 5.29; N, 11.06; S, 6.18. |
| 44 | 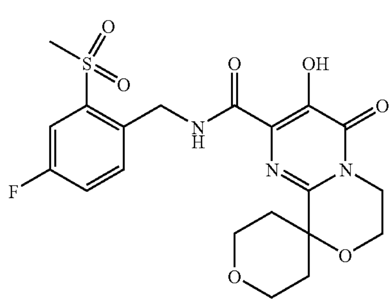 | Yield: 70%. $^1$H-NMR (300 MHz, CDCl$_3$) δ: 11.80 (1H, s), 8.50 (1H, t, J=6.6 Hz), 7.74 (1H, dd J=8.1, 2.9 Hz), 7.65 (1H, dd, J= 8.6, 5.3 Hz), 7.31 (1H, dt, J=8.0, 3.2 H), 4.82 (2H, d, J=6.9 Hz), 3.99 (4H, s), 3.84 (2H, dd, J=11.5, 4.9 Hz), 3.74 (2H, td, J= 11.6, 1.3 Hz), 3.18 (3H, s), 2.31 (2H, td, J= 13.2, 5.5 Hz), 1.74 (2H, d, J=13.2 Hz). HRMS [M + H]$^+$ calcd for C$_{20}$H$_{23}$N$_3$O$_7$SF: 468.1241; found: 468.1237. Anal calcd for C$_{20}$H$_{22}$N$_3$O$_7$SF: C, 51.38; H, 4.74; N, 8.98; S, 6.86; F, 4.06; found: C, 51.25; H, 4.62; N, 8.81; S, 6.82; F, 4.18. |

TABLE 3-continued

| Ex. | Structure | Data |
|---|---|---|
| 45 | 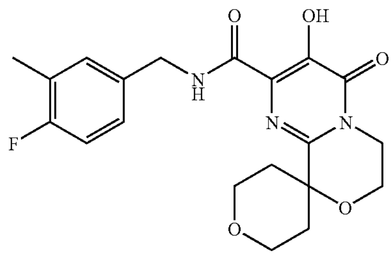 | Yield: 19%. $^1$H-NMR (300 MHz, CDCl$_3$) δ: 12.08 (1H, s), 7.75 (1H, s, J=5.8 Hz), 7.15-7.08 (2H, m), 6.96 (1H, t, J=9.0 Hz), 4.51 (2H, d, J=6.2 Hz), 4.00 (4H, s), 3.85-3.70 (4H, m), 2.32-2.22 (2H, m), 2.26 (3H, d, J=1.8 Hz), 1.76 (2H, d, J=13.5 Hz). HRMS [M + H]$^+$ calcd for C$_{20}$H$_{23}$N$_3$O$_5$F: 404.1622; found: 404.1615. |
| 46 | 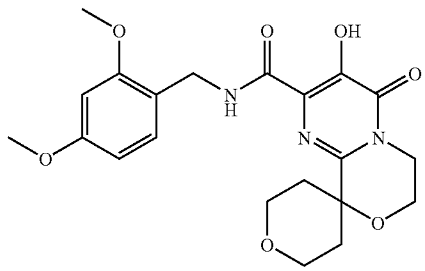 | Yield: 39%. $^1$H-NMR (300 MHz, CDCl$_3$) δ: 12.18 (1H, s), 8.12 (1H, t, J=6.0 Hz), 7.19 (1H, d, J=8.0 Hz), 6.48-6.41 (2H, m), 4.50 (2H, d, J=6.2 Hz), 3.99 (3H, s), 3.88 (3H, s), 3.86-3.71 (4H, m), 3.78 (4H, s), 2.27 (2H, td, J=13.0, 5.6 Hz), 1.76 (2H, d, J=12.8 Hz). HRMS [M + H]$^+$ calcd for C$_{21}$H$_{26}$N$_3$O$_7$: 432.1771; found: 432.1771. Anal calcd for C$_{21}$H$_{25}$N$_3$O$_7$: C, 58.46; H, 5.84; N, 9.74; found: C, 58.22; H, 5.89; N, 9.69. |
| 47 | 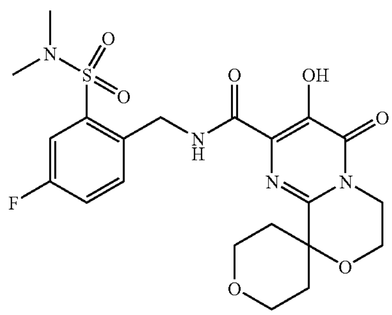 | Yield: 44%. $^1$H-NMR (300 MHz, CDCl$_3$) δ: 11.91 (1H, s), 8.52 (1H, t, J=6.6 Hz), 7.63 (1H, dd, J=8.4, 5.5 Hz), 7.47 (1H, dd, J=8.4, 2.9 Hz), 7.27-7.22 (1H, m), 4.81 (2H, d, J=6.9 Hz), 3.98 (4H, s), 3.85-3.70 (4H, m), 2.90 (6H, s), 2.31 (2H, td, J=13.0, 5.2 Hz), 1.73 (2H, d, J=13.5 Hz). HRMS [M + H]$^+$ calcd for C$_{21}$H$_{26}$N$_4$O$_7$FS: 497.1506; found: 497.1497. Anal calcd for C$_{21}$H$_{25}$N$_4$O$_7$FS: C, 50.80; H, 5.07; N, 11.28; S, 6.45; F, 3.82; found: C, 50.59; H, 4.99; N, 11.01; S, 6.19; F, 4.03. |
| 48 | 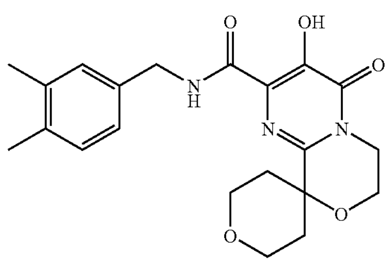 | Yield: 54%. $^1$H-NMR (500 MHz, CDCl$_3$) δ: 12.20 (1H, s), 7.76 (1H, t, J=5.3 Hz), 7.14-7.11 (2H, m), 7.08 (1H, d, J=7.6 Hz), 4.54 (2H, d, J=6.1 Hz), 4.04-4.01 (4H, m), 3.83 (2H, dd, J=11.4, 5.0 Hz), 3.77 (2H, t, J=11.4 Hz), 2.32-2.28 (2H, m), 2.26 (6H, d, J=5.8 Hz), 1.78 (2H, d, J=13.4 Hz). HRMS [M + H]$^+$ calcd for C$_{21}$H$_{26}$N$_3$O$_5$: 400.1872; found: 400.1869. Anal calcd for C$_{21}$H$_{25}$N$_3$O$_5$ C, 63.14; H, 6.30; N, 10.52; found: C, 62.39; H, 6.01; N, 10.23. |
| 49 | 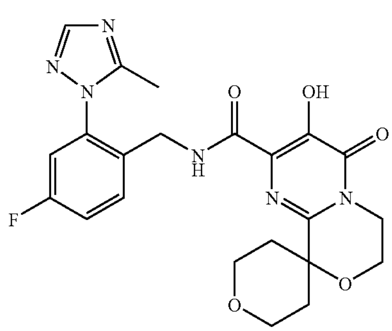 | Yield: 59%. $^1$H-NMR (300 MHz, CDCl$_3$) δ: 11.80 (1H, s), 8.83 (1H, t, J=6.2 Hz) 8.20 (1H, s), 7.63 (1H, dd, J=8.6, 6.0 Hz), 7.20 (1H, dd, J=8.6, 2.4 Hz), 6.99 (1H, dd, J 8.4, 2.6 Hz), 4.27 (2H, d, J=6.6 Hz), 3.99 (4H, s), 3.87 (2H, dd, J=11.3, 4.4 Hz), 3.76 (2H, t, J=11.7 Hz), 2.45 (3H, s), 2.48-2.38 (2H, m), 1.78 (2H, d, J=13.5 Hz). HRMS [M + H]$^+$ calcd for C$_{22}$H$_{24}$N$_6$O$_5$F: 471.1792; found: 471.1786. Anal calcd for C$_{22}$H$_{23}$N$_6$O$_5$F: C, 56.16; H, 4.92; N, 17.86; F, 4.03; found: C, 55.88; H, 5.02; N, 17.74; F, 3.79. |

TABLE 3-continued

| Ex. | Structure | Data |
|---|---|---|
| 50 | 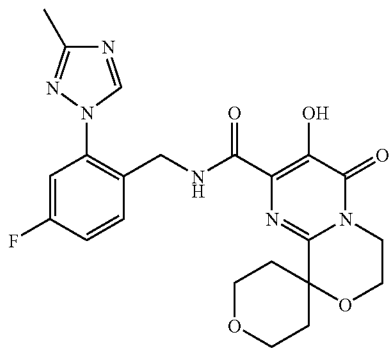 | Yield: 35%. ¹H-NMR (300 MHz, CDCl$_3$) δ: 12.11 (1H, s), 8.78 (1H, t, J=7.3 Hz), 8.28 (1H, s), 7.66 (1H, dd, J=8.6, 6.0 Hz), 7.14 (1H, td, J=8.2, 2.7 Hz), 7.06 (1H, dd, J=8.4, 2.6 Hz), 4.45 (2H, d, J=6.6 Hz), 3.99 (4H, s), 3.82-3.71 (4H, m), 2.59 (3H, s), 2.39-2.29 (2H, m), 1.75 (2H, d, J=14.3 Hz). HRMS (M + H) calcd for C$_{22}$H$_{24}$N$_6$O$_5$F: 471.1792; found: 471.1812. Anal calcd for C$_{22}$H$_{24}$N$_6$O$_5$F.0.2 H$_2$O: C, 55.74; H, 4.98; N, 17.73; F, 4.01; found: C, 55.60; H, 4.92; N, 17.85; F, 3.84. |
| 51 | 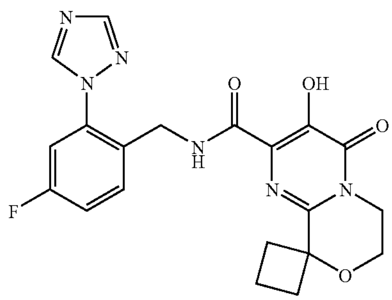 | Yield: 34%. ¹H NMR (500 MHz, CDCl$_3$) δ: 12.01 (1H, s), 8.95 (1H, t, J=6.3 Hz), 8.46 (1H, s), 8.15 (1H, s), 7.73 (1H, dd, J=8.6, 6.1 Hz), 7.21 (1H, td, J=8.2, 2.6 Hz), 7.12 (1H, dd, J=8.6, 2.4 Hz), 4.47 (2H, d, J=6.7 Hz), 3.96 (4H, s), 2.67-2.75 (2H, m), 2.32-2.40 (2H, m), 2.15-2.24 (1H, m), 2.08 (1H, m). HRMS (M + H) calcd for C$_{20}$H$_{20}$N$_6$O$_4$F: 427.1530; found: 427.1540. |
| 52 | 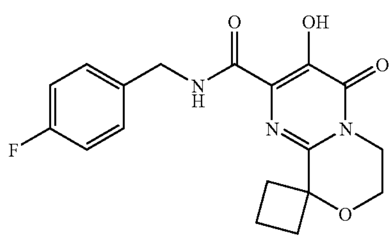 | Yield: 27%. ¹H NMR (500 MHz, CDCl$_3$) δ: 12.00 (1H, s), 7.82-7.90 (1H, m), 7.32 (2H, dd, 9, 5 Hz), 7.02-7.08 (2H, m), 4.61 (2H, d, 6 Hz), 3.97 (4H, ddd, 14, 8, 3 Hz), 2.60-2.66 (2H, m), 2.29-2.36 (2H, m), 2.01-2.10 (1H, m), 1.90-1.99 (1H, m). ¹³C NMR (126 MHz, CDCl$_3$) δ: 168.39, 163.46, 161.50, 157.66, 150.60, 146.85, 133.20, 133.17, 129.42, 129.36, 125.40, 116.02, 115.84, 78.73, 58.62, 42.53, 34.74, 14.13. HRMS (M + H) calcd for C$_{18}$H$_{19}$N$_3$O$_3$F: 360.1360; found: 360.1350. |
| 53 | 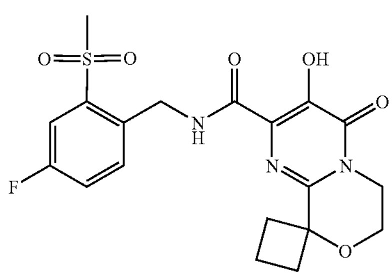 | Yield: 43%. ¹H NMR (500 MHz, CDCl$_3$) δ: 11.81 (1H, s), 8.68 (1H, t, J=7 Hz), 7.71-7.77 (2H, m), 7.35 (1H, td, 8, 3 Hz), 4.84 (2H, d, 7 Hz), 3.93-3.95 (4H, m), 3.18 (3H, s), 2.62-2.68 (2H, m), 2.29-2.36 (2H, m), 2.13-2.19 (1H, m), 2.01-2.08 (1H, m). ¹³C NMR (126 MHz, CDCl$_3$) δ: 168.22, 163.16, 161.14, 157.70, 150.86, 146.63, 140.77, 140.72, 135.31, 135.25, 132.83, 132.80, 125.57, 121.69, 121.53, 117.65, 117.45, 78.69, 58.51, 45.18, 42.53, 40.34, 34.84, 13.59. HRMS (M + H) calcd for C$_{19}$H$_{21}$FN$_3$O$_6$S: 438.1135, found 438.1149. |
| 54 | 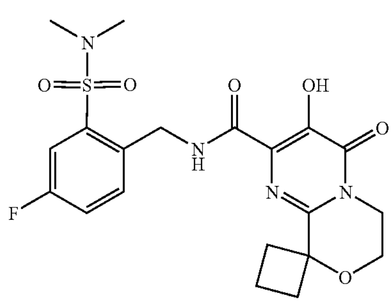 | Yield: 56%. ¹H NMR (500 MHz, CDCl$_3$) δ: 11.91 (1H, s), 8.73 (1H, t, J=6.7 Hz), 7.71 (1H, dd, J=8.4, 5.3 Hz), 7.49 (1H, dd, J=8.4, 2.6 Hz), 7.25-7.29 (1H, m), 4.83 (2H, d, J=7.0 Hz), 3.94 (4H, s), 2.90 (6H, s), 2.64-2.70 (2H, m), 2.28-2.35 (2H, m), 2.12-2.21 (1H, m), 1.99-2.08 (1H, m). ¹³C NMR (126 MHz, CDCl$_3$) δ: 168.09, 162.72, 160.72, 157.75, 150.67, 146.59, 138.58, 138.53, 135.31, 135.25, 132.70, 132.67, 125.73, 120.40, 120.23, 116.86, 116.66, 78.74, 58.53, 42.50, 40.34, 37.61, 34.81, 13.58. HRMS (M + H) calcd for C$_{20}$H$_{24}$N$_4$O$_6$FS 467.1401, found 467.1418. Anal. calcd for C$_{20}$H$_{23}$N$_4$O$_6$FS: C 51.49, H 4.97, N 12.01, F 4.07, S 6.87; found: C 51.27, H 4.98, N 12.17, F 4.11, S 6.86. |

TABLE 3-continued

| Ex. | Structure | Data |
|---|---|---|
| 55 | 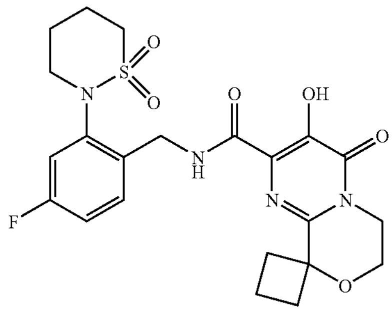 | Yield: 73%. ¹H NMR (500 MHz, CDCl₃) δ: 12.16 (1H, s), 8.33-8.39 (1H, m), 7.49 (1H, dd, J=8.7, 6.3 Hz), 7.17 (1H, dd, J=9.0, 2.6 Hz), 7.07 (1H, td, J=8.2, 2.6 Hz), 4.97 (1H, dd, J=14.0, 8.9 Hz), 4.40 (1H, dd, J=14.3, 3.7 Hz), 3.92-3.98 (4H, m), 3.81-3.88 (1H, m), 3.44 (1H, dt, J=12.6, 3.6 Hz), 3.23-3.28 (2H, m), 2.64-2.70 (2H, m), 2.32-2.42 (2H, m), 2.20-2.29 (2H, m), 1.98-2.06 (2H, m), 1.88-1.98 (2H, m). ¹³C NMR (126 MHz, CDCl₃) δ: 168.28, 163.49, 161.50, 157.79, 150.47, 146.69, 139.89, 139.82, 133.17, 132.16, 132.08, 125.81, 116.64, 116.47, 115.15, 114.97, 79.12, 58.57, 54.17, 51.07, 42.54, 38.53, 34.58, 34.52, 24.97, 24.24, 14.00. HRMS (M + H) calcd for $C_{22}H_{26}N_4O_6FS$ 493.1557; found 493.1549. Anal. calcd for $C_{22}H_{25}N_4O_6FS$: C 53.65, H 5.12, N 11.38, F 3.86, S 6.51; found: C 53.73, H 4.91, N 11.06, F 3.55, S 6.42. |
| 56 | 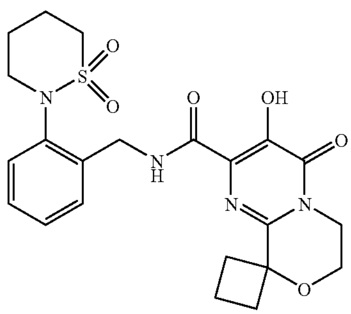 | Yield: 66%. ¹H NMR (500 MHz, CDCl₃) δ: 12.15-12.29 (1H, br s), 8.32-8.40 (1H, m), 7.47-7.52 (1H, m), 7.42-7.47 (1H, m), 7.33-7.39 (2H, m), 4.99 (1H, dd, J=14.0, 8.9 Hz), 4.47 (1H, dd, J=14.3, 3.7 Hz), 3.92-3.98 (4H, m), 3.84-3.92 (1H, m), 3.41-3.47 (1H, m), 3.22-3.28 (2H, m), 2.64-2.71 (2H, m), 2.37-2.46 (1H, m), 2.31-2.37 (1H, m), 2.19-2.29 (2H, m), 1.98-2.06 (2H, m), 1.89-1.98 (2H, m). ¹³C NMR (126 MHz, CDCl₃) δ: 168.26, 157.82, 150.40, 146.68, 138.82, 137.01, 130.80, 129.46, 129.32, 127.72, 125.90, 79.15, 58.58, 54.15, 51.05, 42.53, 39.17, 34.58, 34.51, 25.05, 24.34, 14.03. HRMS (M + H) calcd for $C_{22}H_{27}N_4O_6S$ 475.1651; found 475.1665. Anal. calcd for $C_{22}H_{26}N_4O_6S$: C 55.68, H 5.52, N 11.81, S 6.76; found: C 55.53, H 5.36, N 11.77, S 6.61. |
| 57 | 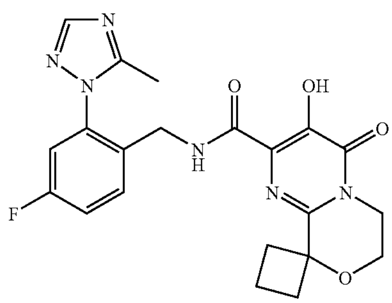 | Yield: 55%. ¹H NMR (500 MHz, CDCl₃) δ: 11.93 (1H, s), 8.61 (1H, br), 7.98 (1H, s), 7.70 (1H, dd, J=8.5, 5.8 Hz), 7.22-7.26 (1H, m), 7.02 (1H, dd, J=8.4, 2.6 Hz), 4.32 (2H, d, J=6.7 Hz), 3.94-3.97 (4H, m), 2.72 (2H, ddd, J=12.7, 9.2, 5.5 Hz), 2.48 (3H, s), 2.36 (2H, ddd, J=12.5, 10.1, 7.3 Hz), 2.15-2.23 (1H, m), 2.05-2.14 (1H, m). ¹³C NMR (126 MHz, CDCl₃) δ: 168.13, 163.04, 161.04, 157.64, 153.70, 151.42, 150.47, 146.83, 137.25, 137.17, 133.57, 133.50, 130.89, 130.86, 125.58, 117.61, 117.45, 114.43, 114.24, 78.78, 65.84, 58.62, 42.44, 38.82, 34.75, 15.29, 13.83, 12.68. HRMS (M + H) calcd for $C_{21}H_{22}N_6O_4F$: 441.1687; found: 441.1692. |
| 58 | 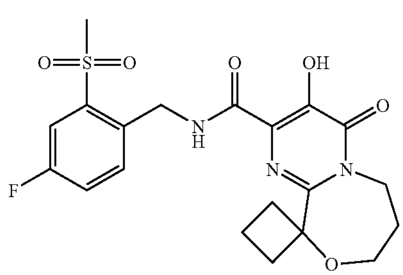 | Yield: 43%. ¹H NMR (500 MHz, CDCl₃) δ: 11.90 (1H, br s), 8.62 (1H, t, 6.7 Hz), 7.74 (1H, dd, J=7.9, 2.8 Hz), 7.71 (1H, dd, J=8.6, 5.2 Hz), 7.34 (1H, dt, J=8.0, 2.6 Hz), 4.83 (2H, d, J=6.7 Hz), 4.36 (2H, br), 3.89 (2H, t, J=5.7 Hz), 3.17 (3H, s), 2.69-2.79 (2H, br), 2.37-2.46 (2H, m), 1.85-1.94 (1H, m), 1.79-.85 (2H, m), 1.63-1.73 (1H, m). ¹³C NMR (125.77 MHz, CDCl₃) δ: 168.34, 163.12, 161.11, 158.52, 151.12, 147.55, 140.72, 140.67, 135.12, 135.05, 132.86, 132.83, 124.42, 121.66, 121.49, 117.61, 117.41, 82.32, 64.43, 45.17, 40.80, 40.25, 32.02, 28.59, 12.79. HRMS (M + H) calcd for $C_{20}H_{23}FN_3O_6S$: 452.1292, found 452.1299. |

TABLE 3-continued

| Ex. | Structure | Data |
|---|---|---|
| 59 | 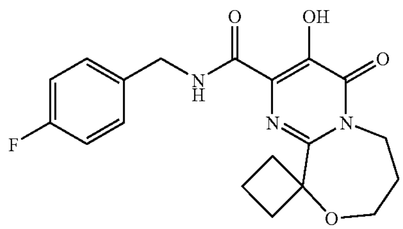 | Yield: 52%. ¹H NMR (500 MHz, CDCl₃) δ: 12.09 (1H, s), 7.82 (1H, br t), 7.31 (2H, dd, J=8.1, 5.6 Hz), 7.05 (2H, t, J=8.5 Hz), 4.59 (2H, d, J=6.1Hz), 4.39 (2H, br), 3.92 (2H, t, J=5.5 Hz), 2.63-2.71 (2H, br), 2.38-2.46 (2H, m), 1.89 (1H, td, J=10.0, 5.6 Hz), 1.82-1.87 (2H, m), 1.60-1.69 (1H, m). ¹³C NMR (126 MHz, CDCl₃) δ: 168.48, 163.46, 161.49, 158.45, 150.94, 147.73, 133.15, 133.12, 129.45, 129.39, 124.27, 115.99, 115.83, 82.11, 64.59, 42.49, 40.81, 31.88, 28.67, 12.85. HRMS (M + H) calcd for C₁₉H₂₁FN₃O₄: 374.1516; found: 374.1515. |
| 60 | 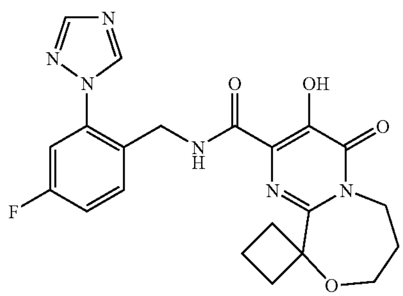 | Yield: 18%. ¹H NMR (500 MHz, CDCl₃) δ: 12.10 (1H, s), 9.02 (1H, t, J=6.4 Hz), 8.46 (1H, s), 8.13 (1H, s), 7.71 (1H, dd, J=8.5, 5.8 Hz), 7.21 (1H, td, J=8.2, 2.7 Hz), 7.11 (1H, dd, J=8.4, 2.6 Hz), 4.45 (2H, d, J= 7.0 Hz), 4.38 (2H, br), 3.89 (2H, t, J=5.6 Hz), 2.82 (2H, br), 2.41-2.48 (2H, m), 1.87-1.95 (1H, m), 1.83 (2H, ddd, J=10.8, 5.6, 5.5 Hz), 1.69-1.78 (1H, m). ¹³C NMR (126 MHz, CDCl₃) δ: 168.10, 163.20, 161.20, 158.53, 152.73, 150.74, 147.62, 143.85, 136.97, 136.89, 134.46, 134.38, 128.65, 128.61, 124.63, 117.14, 116.98, 112.38, 112.19, 82.35, 64.46, 40.71, 39.11, 32.10, 28.61, 12.71. HRMS (M + H) calcd for C₂₁H₂₂FN₆O₄: 441.1687, found: 441.1695. |
| 61 | 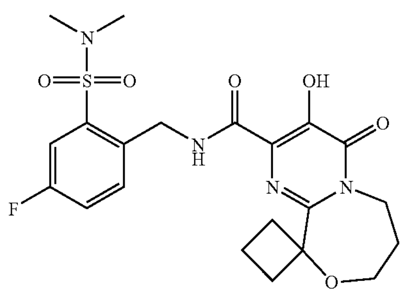 | Yield: 33%. ¹H NMR (500 MHz, CDCl₃) δ: 12.02 (1H, br s), 8.64 (1H, t, J=6.6 Hz), 7.69 (1H, dd, J=8.5, 5.5 Hz), 7.49 (1H, dd, J=8.2, 2.7 Hz), 7.24-7.29 (1H, m), 4.82 (2H, d, J=6.7 Hz), 4.36 (2H, br), 3.88 (2H, t, J=5.5 Hz), 2.89 (6H, s), 2.74 (2H, m), 2.37-2.44 (2H, m), 1.85-1.92 (1H, m), 1.82 (2H, dt, J=11.0, 5.5 Hz), 1.65-1.74 (1H, m). ¹³C NMR (126 MHz, CDCl₃) δ: 168.21, 162.69, 160.68, 158.54, 150.96, 147.55, 138.56, 138.50, 135.15, 135.09, 132.72, 132.69, 124.57, 120.38, 120.22, 116.84, 116.64, 82.37, 64.39, 40.71, 40.22, 37.58, 32.09, 28.59, 12.77. HRMS (M + H) calcd for C₂₁H₂₆FN₄O₆FS 481.1557, found 481.1555. Anal. calcd for C₂₁H₂₅N₄O₆FS: C 52.49, H 5.24, N 11.66, F 3.95, S 6.67; found: C 52.22, H 5.09, N 11.43, F 3.93, S 6.60. |
| 62 | 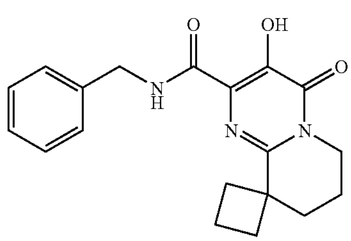 | Yield: 82%. ¹H NMR (500 MHz, CDCl₃) δ: 11.90 (1H, s), 8.03 (1H, br t), 7.40-7.30 (5H, m), 4.67 (2H, d, J=6.4 Hz), 3.96 (2H, t, J=6.4 Hz), 2.63-2.57 (2H, m), 2.07-1.91 (8H, m). HRMS (M + H) calcd for C₁₉H₂₂N₃O₃: 340.1661; found: 340.1652. Anal calcd for C₁₉H₂₁N₃O₃: C, 67.24; H, 6.23; N, 12.38; found: C, 66.85; H, 6.14; N, 12.31. |
| 63 | 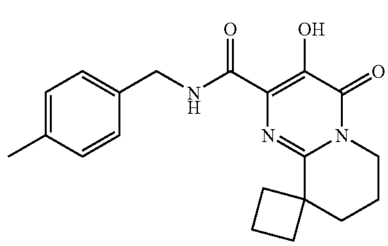 | Yield: 78%. ¹H NMR (500 MHz, CDCl₃) δ: 11.93 (1H, s), 7.99 (1H, br t), 7.25 (2H, d, J= 6.7 Hz), 7.18 (2H, d, J=7.6 Hz), 4.62 (2H, d, J=6.1 Hz), 3.96 (2H, t, J=6.3 Hz), 2.62-2.56 (2H, m), 2.35 (3H, s), 2.07-1.90 (8H, m). HRMS (M + H) calcd for C₂₀H₂₄N₃O₃: 354.1818; found: 354.1823. Anal calcd for C₂₀H₂₃N₃O₃: C, 67.97; H, 6.55; N, 11.89; found: C, 67.81; H, 6.84; N, 11.94. |

TABLE 3-continued

| Ex. | Structure | Data |
|---|---|---|
| 64 | (4-methoxybenzyl carboxamide spiro-cyclobutane pyrimidinone structure) | Yield: 76%. $^1$H NMR (500 MHz, CDCl$_3$) δ: 11.93 (1H, s), 7.96 (1H, t, J=5.2 Hz), 7.29 (2H, d, J=8.5 Hz), 6.90 (2H, d, J=8.5 Hz), 4.59 (2H, d, J=6.6 Hz), 3.96 (2H, t, J=6.4 Hz), 3.81 (3H, s) 2.62-2.56 (2H, m), 2.07-1.90 (8H, m). HRMS (M + H) calcd for C$_{20}$H$_{24}$N$_3$O$_3$: 370.1767; found: 370.1780. Anal calcd for C$_{20}$H$_{23}$N$_3$O$_3$: C, 65.02; H, 6.27; N, 11.37; found: C, 64.94; H, 6.53; N, 11.46. |
| 65 | (4-chlorobenzyl carboxamide structure) | Yield: 74%. $^1$H NMR (500 MHz, CDCl$_3$) δ: 11.79 (1H, s), 8.02 (1H, br t), 7.34 (2H, d, J=8.6 Hz), 7.29 (2H, d, J=8.6 Hz), 4.63 (2H, d, J=6.4 Hz), 3.96 (2H, t, J=6.4 Hz), 2.63-2.57 (2H, m), 2.08-1.91 (8H, m). HRMS (M + H) calcd for C$_{19}$H$_{21}$ClN$_3$O$_3$: 374.1271; found: 374.1287. Anal calcd for C$_{19}$H$_{20}$ClN$_3$O$_3$: C, 61.04; H, 5.39; N, 11.24; found: C, 61.05; H, 5.41; N, 11.10. |
| 66 | (4-fluorobenzyl carboxamide structure) | Yield: 72%. $^1$H NMR (500 MHz, CDCl$_3$) δ: 11.83 (1H, s), 8.01 (1H, br t), 7.34 (2H, dd, J=8.6, 5.2 Hz), 7.06 (2H, t, J=8.6 Hz), 4.62 (2H, d, J=6.4 Hz), 3.96 (2H, t, J=6.3 Hz), 2.62-2.56 (2H, m), 2.08-1.91 (8H, m). HRMS (M + H) calcd for C$_{19}$H$_{21}$FN$_3$O$_3$: 358.1567; found: 358.1551. Anal calcd for C$_{19}$H$_{20}$FN$_3$O$_3$: C, 63.85; H, 5.64; N, 11.75; found: C, 63.72; H, 5.52; N, 11.63. |
| 67 | (3-fluorobenzyl carboxamide structure) | Yield: 80%. $^1$H NMR (500 MHz, CDCl$_3$) δ: 11.78 (1H, s), 8.06 (1H, br t), 7.36-7.31 (1H, m), 7.14 (1H, d, J=7.9 Hz), 7.06 (1H, d, J=9.5 Hz), 7.00 (1H, td, J=8.4, 2.4 Hz), 4.66 (2H, d, J=6.4 Hz), 3.97 (2H, t, J=6.4 Hz), 2.64-2.58 (2H, m), 2.09-1.91 (8H, m). HRMS (M + H) calcd for C$_{19}$H$_{21}$FN$_3$O$_3$: 358.1567; found: 358.1553. Anal calcd for C$_{19}$H$_{20}$FN$_3$O$_3$: C, 63.85; H, 5.64; N, 11.75; found: C, 63.86; H, 5.64; N, 11.50. |
| 68 | (2-fluorobenzyl carboxamide structure) | Yield: 75%. $^1$H NMR (500 MHz, CDCl$_3$) δ: 11.78 (1H, s), 8.14 (1H, br t), 7.40 (1H, td, J=7.5, 1.2 Hz), 7.32-7.28 (1H, m), 7.14 (1H, td, J=7.5, 1.0 Hz), 7.09 (1H, dd, J=10.1, 8.2 Hz), 4.70 (2H, d, J=6.4 Hz), 3.95 (2H, t, J=6.4 Hz), 2.65-2.59 (2H, m), 2.09-1.90 (8H, m). HRMS (M + H) calcd for C$_{19}$H$_{21}$FN$_3$O$_3$: 358.1567; found: 358.1569. Anal calcd for C$_{19}$H$_{20}$FN$_3$O$_3$: C, 63.85; H, 5.64; N, 11.75; found: C, 63.75; H, 5.55; N, 11.70. |
| 69 | (3,4-dimethylbenzyl carboxamide structure) | Yield: 71%. $^1$H NMR (500 MHz, CDCl$_3$) δ: 11.95 (1H, s), 7.99 (1H, br t), 7.14 (1H, d, J=7.6 Hz), 7.13 (1H, s), 7.09 (1H, d, J=7.6 Hz), 4.59 (2H, d, J=6.4 Hz), 3.96 (2H, t, J=6.4 Hz), 2.62-2.57 (2H, m), 2.27 (3H, s), 2.26 (3H, s), 2.07-1.90 (8H, m). HRMS (M + H) calcd for C$_{21}$H$_{26}$N$_3$O$_3$: 368.1974; found: 368.1960. Anal calcd for C$_{21}$H$_{25}$N$_3$O$_3$: C, 68.64; H, 6.85; N, 11.43; found: C, 67.93; H, 5.93; N, 11.27. |

TABLE 3-continued

| Ex. | Structure | Data |
|---|---|---|
| 70 | 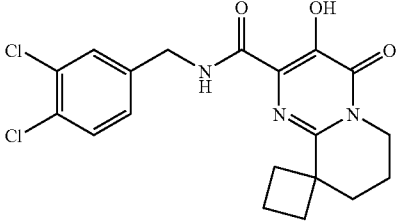 | Yield: 91%. $^1$H NMR (500 MHz, CDCl$_3$) δ: 11.70 (1H, s), 8.05 (1H, t, J=5.5 Hz), 7.44 (1H, s), 7.43 (1H, d, J=5.5 Hz), 7.21 (1H, dd, J=8.1, 1.7 Hz), 4.61 (2H, d, J=6.4 Hz), 3.97 (2H, t, J=6.4 Hz), 2.64-2.58 (2H, m), 2.09-1.91 (8H, m). HRMS (M + H) calcd for C$_{19}$H$_{20}$Cl$_2$N$_3$O$_3$: 408.0882; found: 408.0871. Anal calcd for C$_{19}$H$_{19}$Cl$_2$N$_3$O$_3$: C, 55.89; H, 4.69; N, 10.29; found: C, 55.65; H, 4.51; N, 10.26. |
| 71 | 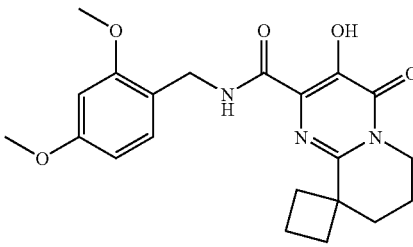 | Yield: 81%. $^1$H NMR (500 MHz, CDCl$_3$) δ: 11.99 (1H, s), 8.35 (1H, t, J=5.5 Hz, 7.23 (1H, d, J=8.2 Hz), 6.49 (1H, d, J=2.1 Hz), 6.46 (1H, dd, J=8.2, 2.1 Hz), 4.55 (2H, d, J=6.4 Hz), 3.94 (2H, t, J=6.4 Hz), 3.88 (3H, s), 3.80 (3H, s), 2.65-2.59 (2H, m), 2.10-1.89 (8H, m). HRMS (M + H) calcd for C$_{21}$H$_{26}$N$_3$O$_5$: 400.1872; found: 400.1884. Anal calcd for C$_{21}$H$_{25}$N$_3$O$_5$: C, 63.14; H, 6.30; N, 10.52; found: C, 62.99; H, 6.46; N, 10.49. |
| 72 | 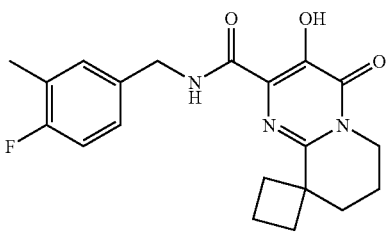 | Yield: 74%. $^1$H NMR (500 MHz, CDCl$_3$) δ: 11.86 (1H, s), 7.99 (1H, t, J=4.9 Hz), 7.17 (1H, d, J=7.0 Hz), 7.15-7.12 (1H, m), 6.99 (1H, t, J=8.9 Hz), 4.58 (2H, d, J=6.4 Hz), 3.96 (2H, t, J=6.4 Hz), 2.63-2.57 (2H, m), 2.28 (3H, d, J=1.5 Hz), 2.08-1.91 (8H, m). HRMS (M + H) calcd for C$_{20}$H$_{23}$FN$_3$O$_3$: 372.1723; found: 372.1737. Anal calcd for C$_{20}$H$_{22}$FN$_3$O$_3$: C, 64.67; H, 5.97; N, 11.31; found: C, 64.73; H, 6.20; N, 11.30. |
| 73 | 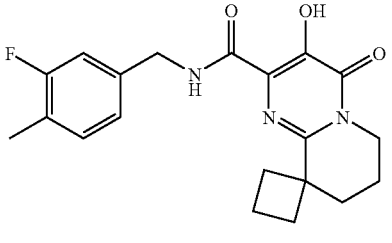 | Yield: 73%. $^1$H NMR (500 MHz, CDCl$_3$) δ: 11.82 (1H, s), 8.02 (1H, br t), 7.17 (1H, t, J= 7.8 Hz), 7.02 (1H, d, J=8.6 Hz), 7.00 (1H, d, J=10.7 Hz), 4.61 (2H, d, J=6.1 Hz), 3.96 (2H, t, J=6.4 Hz), 2.63-2.57 (2H, m), 2.26 (3H, s), 2.08-1.91 (8H, m). HRMS (M + H) calcd for C$_{20}$H$_{23}$FN$_3$O$_3$: 372.1723; found: 372.1714. Anal calcd for C$_{20}$H$_{22}$FN$_3$O$_3$: C, 64.67; H, 5.97; N, 11.31; found: C, 64.56; H, 6.08; N, 11.41. |
| 74 | 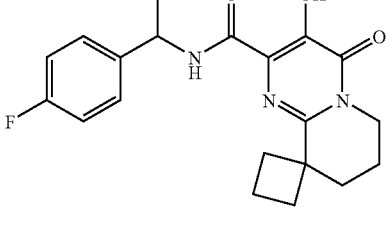 | Yield: 73%. $^1$H NMR (500 MHz, CDCl$_3$) δ: 11.78 (1H, s), 7.91 (1H, d, J=7.6 Hz), 7.36-7.33 (2H, m), 7.06 (2H, td, J=8.6, 1.2 Hz), 5.25-5.19 (H, m), 3.96 (2H, t, J=6.4 Hz), 2.64-2.56 (2H, m), 2.11-1.91 (8H, m), 1.62 (3H, d, J=7.0 Hz). HRMS (M + H) calcd for C$_{20}$H$_{23}$FN$_3$O$_3$: 372.1723; found: 372.1708. Anal calcd for C$_{20}$H$_{22}$FN$_3$O$_3$: C, 64.67; H, 5.97; N, 11.31; found: C, 63.20; H, 6.22; N, 10.74. |
| 75 | 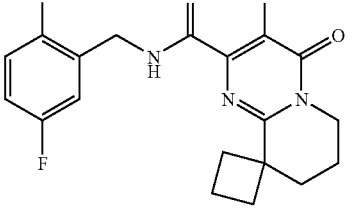 | Yield: 79%. $^1$H NMR (500 MHz, CDCl$_3$) δ: 11.67 (1H, s), 8.13 (1H, br t), 7.11-7.03 (2H, m), 6.99-6.94 (1H, m), 4.68 (2H, d, J= 6.4 Hz), 3.96 (2H, t, J=6.4 Hz), 2.65-2.59 (2H, m), 2.10-1.91 (8H, m). HRMS (M + H) calcd for C$_{19}$H$_{20}$F$_2$N$_3$O$_3$: 376.1473; found: 376.1483. Anal calcd for C$_{19}$H$_{19}$F$_2$N$_3$O$_3$: C, 60.79; H, 5.10; N, 11.19; found: C, 60.60; H, 5.21; N, 11.17. |

TABLE 3-continued

| Ex. | Structure | Data |
|---|---|---|
| 76 | (2,5-dichlorobenzyl structure) | Yield: 75%. ¹H NMR (500 MHz, CDCl₃) δ: 11.62 (1H, s), 8.30 (1H, t, J=5.8 Hz), 7.41 (1H, d, J=2.5 Hz), 7.34 (1H, d, J=8.6 Hz), 7.25 (1H, dd, J=8.2, 2.4 Hz), 4.69 (2H, d, J=6.7 Hz), 3.96 (2H, t, J=6.3 Hz), 2.66-2.60 (2H, m), 2.11-1.91 (8H, m). HRMS (M + H) calcd for $C_{19}H_{20}Cl_2N_3O_3$: 408.0882; found: 408.0879. Anal calcd for $C_{19}H_{19}Cl_2N_3O_3$: C, 55.89; H, 4.69; N, 10.29; found: C, 55.66; H, 4.83; N, 10.27. |
| 77 | (triazolyl-fluorobenzyl structure) | Yield: 51%. ¹H NMR (500 MHz, CDCl₃) δ: 11.74 (1H, s), 8.97 (1H, t, J=6.4 Hz), 8.41 (1H, s), 8.16 (1H, s), 7.44 (1H, dd, J=8.5, 2.8 Hz), 7.35 (1H, dd, J=8.5, 4.9 Hz), 7.15 (1H, td, J=8.5, 2.8 Hz), 4.46 (2H, d, J=6.7 Hz), 3.94 (2H, t, J=6.4 Hz), 2.75-2.69 (2H, m), 2.16-1.90 (8H, m). HRMS (M + H) calcd for $C_{21}H_{22}FN_6O_3$: 425.1737; found: 425.1735. Anal calcd for $C_{21}H_{21}FN_6O_6$: C, 59.42; H, 4.98; N, 19.80; found: C, 59.20; H, 4.88; N, 19.51. |
| 78 | (triazolyl-fluorobenzyl structure) | Yield: 59%. ¹H NMR (500 MHz, CDCl₃) δ: 11.81 (1H, s), 9.07 (1H, t, J=6.4 Hz), 8.46 (1H, s), 8.18 (1H, s), 7.73 (1H, dd, J=8.4, 6.0 Hz), 7.22 (1H, td, J=8.2, 2.4 Hz), 7.12 (1H, dd, J=8.6, 2.4 Hz), 4.48 (2H, d, J=6.7 Hz), 3.94 (2H, t, J=6.4 Hz), 2.75-2.69 (2H, m), 2.17-1.89 (8H, m). HRMS (M + H) calcd for $C_{21}H_{22}FN_6O_3$: 425.1737; found: 425.1727. Anal calcd for $C_{21}H_{21}FN_6O_6$: C, 59.42; H, 4.98; N, 19.80; found: C, 59.35; H, 4.69; N, 19.85. |
| 79 | (sulfonyl-fluorobenzyl structure) | Yield: 53%. ¹H NMR (500 MHz, CDCl₃) δ: 11.96 (1H, s), 8.42 (1H, br t), 7.49 (1H, dd, J=8.5, 6.4 Hz), 7.18 (1H, dd, J=9.2, 2.4 Hz), 7.08 (1H, td, J=8.2, 2.4 Hz), 4.99 (1H, dd, J=14.4, 8.5 Hz), 4.42 (1H, dd, J=14.4, 3.7 Hz), 3.99-3.83 (3H, m), 3.45 (1H, dt, J=12.5, 4.0 Hz), 3.28-3.25 (2H, m), 2.70-2.61 (2H, m), 2.45-2.31 (2H, m), 2.03-1.9 (10H, m). HRMS (M + H) calcd for $C_{23}H_{28}FN_4O_5S$: 491.1764; found: 491.1776. Anal calcd for $C_{23}H_{27}FN_4O_5S$: C, 56.31; H, 5.54; N, 11.41; found: C, 56.07; H, 5.60; N, 11.25. |
| 80 | (triazolyl-benzyl structure) | Yield: 66%. ¹H NMR (500 MHz, CDCl₃) δ: 11.87 (1H, s), 9.11 (1H, t, J=6.4 Hz), 8.45 (1H, s), 8.17 (1H, s), 7.73 (1H, dd, J=7.3, 1.2 Hz), 7.51 (1H, td, J=7.3, 1.2 Hz), 7.47 (1H, td, J=7.6, 1.5 Hz), 7.36 (1H, dd, J=7.6, 1.0 Hz), 4.51 (2H, d, J=6.7 Hz), 3.94 (2H, t, J=6.4 Hz), 2.76-2.70 (2H, m), 2.17-1.89 (8H, m). HRMS (M + H) calcd for $C_{21}H_{23}N_6O_3$: 407.1832; found: 407.1833. Anal calcd for $C_{21}H_{22}N_6O_3$: C, 62.05; H, 5.45; N, 20.67; found: C, 61.86; H, 5.48; N, 20.90. |

TABLE 3-continued

| Ex. | Structure | Data |
|---|---|---|
| 81 | 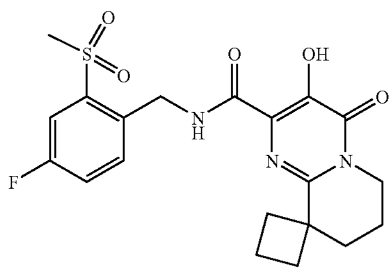 | Yield: 57%. ¹H NMR (500 MHz, CDCl₃) δ: 11.60 (1H, s), 8.78 (1H, t, J=6.4 Hz), 7.76 (1H, dd, J=8.2, 2.4 Hz), 7.73 (1H, dd, J= 8.6, 5.2 Hz), 7.35 (1H, td, J=8.2, 2.8 Hz), 4.86 (2H, d, J=7.0 Hz), 3.93 (2H, t, J=6.4 Hz), 3.19 (3H, s), 2.68-2.62 (2H, m), 2.15-1.88 (8H, m). HRMS (M + H) calcd for $C_{20}H_{23}FN_3O_5S$: 436.1342; found: 436.1325. Anal calcd for $C_{20}H_{22}FN_3O_5S$: C, 55.16; H, 5.09; N, 9.65; found: C, 55.00; H, 4.93; N, 9.45. |
| 82 | 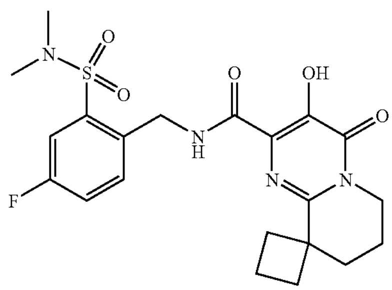 | Yield: 64%. ¹H NMR (500 MHz, CDCl₃) δ: 11.48 (1H, br s), 8.82 (1H, t, J=6.4 Hz), 7.71 (1H, dd, J=8.2, 5.5 Hz), 7.51 (1H, dd, J=8.2, 2.1 Hz), 7.29 (1H, J=8.2, 2.4 Hz), 4.85 (2H, d, J=7.0 Hz), 3.94 (2H, t, J= 6.4 Hz), 2.91 (6H, s), 2.69-2.64 (2H, m), 2.15-1.89 (8H, m). HRMS (M + H) calcd for $C_{21}H_{26}FN_4O_5S$: 465.1608; found: 465.1593. Anal calcd for $C_{21}H_{25}FN_4O_5S \cdot 0.44\ CF_3CO_2H$: C, 51.06; H, 4.98; N, 10.89; found: C, 51.41; H, 5.18; N, 10.50. |
| 83 | 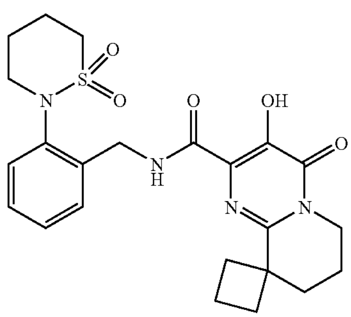 | Yield: 48%. ¹H NMR (500 MHz, CDCl₃) δ: 12.01 (1H, s), 8.43-8.41 (1H, m), 7.50-7.48 (1H, m), 7.46-7.45 (1H, m), 7.35-7.35 (2H, m), 5.02 (1H, dd, J=14.3, 8.6 Hz), 4.49 (1H, dd, J=14.3, 4.0 Hz), 3.96-3.87 (3H, m), 3.46-3.42 (1H, m), 3.27-3.24 (2H, m), 2.71-2.61 (2H, m), 2.45-2.31 (2H, m), 2.02-1.84 (10H, m). HRMS (M + H) calcd for $C_{23}H_{29}N_4O_5S$: 473.1859; found: 473.1866. Anal calcd for $C_{23}H_{28}N_4O_5S \cdot 0.12\ C_2H_5OH \cdot 0.3\ H_2O$: C, 57.73; H, 6.11; N, 11.59; found: C, 57.48; H, 5.67; N, 11.47. |
| 84 | 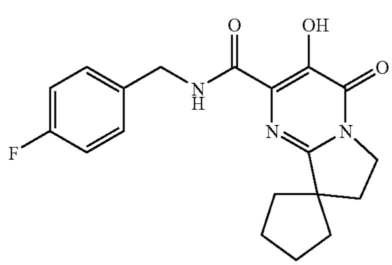 | Yield = 47%. ¹H NMR (300 MHz, CDCl₃) δ: 1.65-2.02 (8 H, m), 2.07 (2 H, t, J=7 Hz), 4.03 (2 H, t, J=7 Hz), 4.55 (2 H, d, J=6.2 Hz), 7.02 (2 H, t, J=8.6 Hz), 7.29 (2 H, dd, J= 8.6, 5.3 Hz), 7.90 (1H, brs), 12.09 (1 H, s). HRMS (M + H) calcd for $C_{19}H_{21}FN_3O_3$: 358.1567; found: 358.1578. |
| 85 | 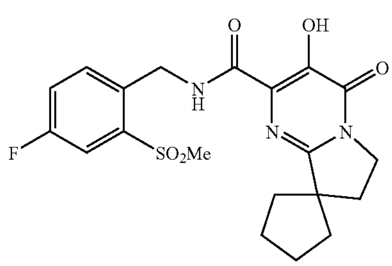 | Yield: = 54%. ¹H NMR (300 MHz, CDCl₃) δ: 1.64 1.78 (4 H, m), 1.87-2.01 (4 H, m), 2.07 (2 H, t, J=7 Hz), 3.15 (3H, s), 4.01 (2 H, t, J=7 H), 4.82 (2 H, d, J=7.0 Hz), 7.32 (1 H, dd, J=7.9, 2.7 Hz), 7.62-7.78 (2 H, m), 8.55 (1 H, t, J=7.0 Hz), 11.87 (1 H, s). HRMS (M + H) calcd for $C_{20}H_{23}FH_3O_5S$: 436.1342; found 436.1341. |

TABLE 3-continued

| Ex. | Structure | Data |
|---|---|---|
| 86 | 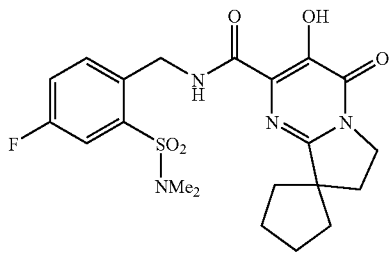 | Yield = 15%. $^1$H NMR (300 MHz, CDCl$_3$) δ: 1.62-1.79 (4 H, m), 1.86-2.02 (4 H, m), 2.07 (2 H, t, J=7 Hz), 2.86 (6 H, s), 4.00 (2H, t, J=7 Hz), 4.80 (2 H, d, J=6.6 Hz), 7.19-7.30 (1H, m), 7.50 (1H, dd, =8.4, 2.6 Hz), 7.66 (1H, dd, J=8.6, 5.3 Hz), 8.54 (1 H, t, J=6.8 Hz), 12.00 (1H, s). HRMS (M + H) calcd for C$_{21}$H$_{26}$FN$_4$O$_5$S: 465.1608; found 465.1626. |
| 87 | 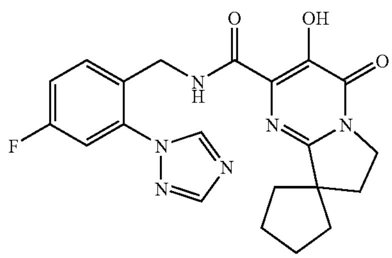 | Yield = 13%. $^1$H NMR (300 MHz, CDCl$_3$) δ: 1.64-1.83 (4 H, m), 1.87-2.05 (4 H, m), 1.87-2.05 (4 H, m), 2.09 (2 H, t, J=7 Hz), 4.01 (2H, t, J=7 Hz), 4.44 (2 H, d, J=6.6 Hz), 7.08 (1H, dd, J=8.4, 2.5 Hz), 7.19 (1 H, dt, J=8.4, 2.5 Hz), 7.67 (1 H, dd, J= 8.4, 5.9 Hz), 8.15 (1H, s), 8.42 (1H, s), 8.77 (1H, t, J=6.8 Hz), 12.02 (1H, s). HRMS (M + H) calcd for C$_{21}$H$_{22}$FN$_6$O$_3$: 425.1737; found 425.1741. |
| 88 | 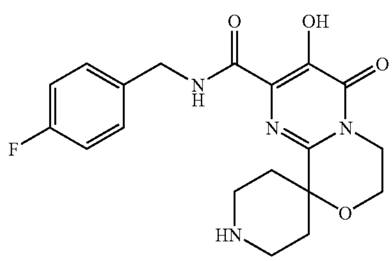 | Yield: 27%. $^1$H-NMR (300 MHz, CDCl$_3$/MeOD) δ: 7.31-7.27 (2H, m), 7.00 (2H, t, J=8.6 Hz), 4.53 (2H, s), 3.98 (4H, s), 2.98-2.84 (4H, m), 2.14 (2H, td, J= 10.3, 5.4 Hz), 1.84 (2H, dd, J=12.8, 1.1 Hz). HRMS (M + H) calcd for C$_{19}$H$_{22}$N$_4$O$_4$F: 389.1625; found: 389.1610. |

EXAMPLE 89

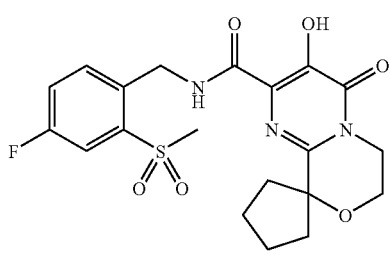

A mixture of example 18 (52 mg, 0.124 mmol) and mCPBA (64.2 mg, 0.372 mmol) in CH$_2$Cl$_2$ was stirred at room temperature for 4 h. Then, concentrated and purified by preparative HPLC to afford example 89 (26.2 mg, 47%) as a purple solid. $^1$H NMR (500 MHz, CDCl$_3$) δ: 11.69 (1H, s), 8.54 (1H, t, J=6.4 Hz), 7.75 (1H, dd, J=8.2, 2.7 Hz), 7.70 (1H, dd, J=8.6, 5.2 Hz), 7.34 (1H, td, J=7.9, 2.5 Hz), 4.81 (2H, d, J=6.7 Hz), 3.99-3.94 (4H, m), 3.16 (3H, s), 2.21-2.16 (2H, m), 2.06-2.00 (2H, m), 1.94-1.82 (4H, m). HRMS (M+H) calcd for C$_{20}$H$_{23}$FN$_3$O$_6$S: 452.1292; found: 452.1286.

EXAMPLE 90

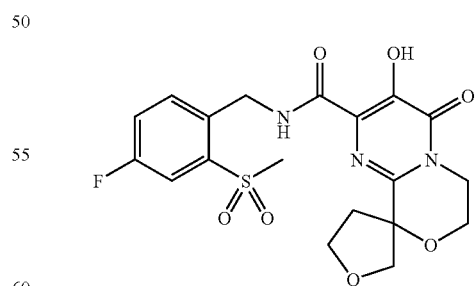

Example 90 was prepared according to the procedure for example 89 using example 39 to afford product in 38% as a purple solid. $^1$H NMR (500 MHz, CDCl$_3$) δ: 11.82 (1H, bs), 8.57 (1H, t, J=5.8 Hz), 7.75 (1H, dd, J=8.0, 2.6 Hz), 7.69 (1H, dd, J=8.4, 5.0 Hz), 7.33 (1H, td, J=7.9, 2.4 Hz), 4.87-4.74

(2H. m), 4.20-3.98 (8H, m), 3.18 (3H, s), 2.61-2.56 (1H, m), 2.34-2.29 (1H, m). HRMS (M+H) calcd for $C_{19}H_{21}FN_3O_7S$: 454.1084; found: 454.1096.

EXAMPLE 91

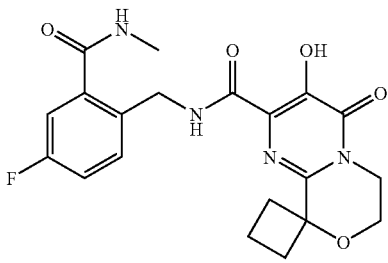

A solution of intermediate 45 (0.096 g, 0.190 mmol) in dichloromethane (5 mL) and trifluoroacetic acid (5 mL) was stirred for 2 hours, and then solvent was removed in-vacuo to give a yellow oil. The oil was triturated with a minimal volume of 95% ethanol, and solids were collected by filtration to give 91 (0.056 g, 71%) as a white solid after vacuum pump drying: $^1$H NMR (500 MHz, DMSO-D$_6$) δ: 12.19 (1H, s), 9.37 (1H, t, J=6.4 Hz), 8.56-8.61 (1H, m), 7.44 (1H, dd, J=8.5, 5.8 Hz), 7.36 (1H, dd, J=9.3, 2.6 Hz), 7.31 (1H, td, J=8.5, 2.6 Hz), 4.58 (2H, d, J=6.7 Hz), 3.92 (2H, t, J=5.3 Hz), 3.80 (2H, t, J=5.2 Hz), 2.79 (3H, d, J=4.6 Hz), 2.65-2.72 (2H, m), 2.19-2.25 (2H, m), 2.12-2.18 (1H, m), 1.88-1.96 (1H, m). $^{13}$C NMR (126 MHz, DMSO-D$_6$) δ: 167.68, 161.68, 159.73, 156.73, 150.37, 145.81, 137.24, 137.19, 132.61, 131.33, 131.27, 125.22, 116.87, 116.70, 114.88, 114.70, 77.99, 57.88, 41.96, 40.33, 33.95, 26.06, 13.08. HRMS (M+H) calc'd for $C_{20}H_{22}N_4O_5F$: 417.1574; found: 417.1589.

EXAMPLE 92

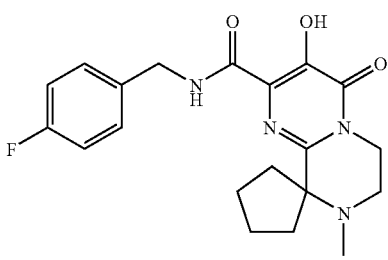

Spiro[cyclopentane-1,9'(6'H)-[4H]pyrazino[1,2-a]pyrimidine]-2'-carboxamide, N-[(4-fluorophenyl)methyl]-7',8'-dihydro-3'-hydroxy-8'-methyl-4'-oxo-. $^1$H NMR (500 MHz, CHLOROFORM-D) δ ppm 1.82-1.91 (m, 2 H) 1.96-2.05 (m, 2 H) 2.37 (d, J=7.32 Hz, 4 H) 2.88 (s, 3 H) 3.81 (t, J=6.41 Hz, 2 H) 4.27-4.35 (m, 2 H) 4.58 (d, J=6.10 Hz, 2 H) 7.03-7.09 (m, 2 H) 7.29 (dd, J=8.55, 5.19 Hz, 2 H). $^{13}$C NMR (125 MHz, CHLOROFORM-D) δ 25.48, 25.67, 37.53, 37.70, 39.57, 42.78, 46.18, 73.38, 115.99, 116.16, 125.28, 129.41, 132.64, 146.79, 147.64, 157.41, 161.61, 167.67.

EXAMPLE 93

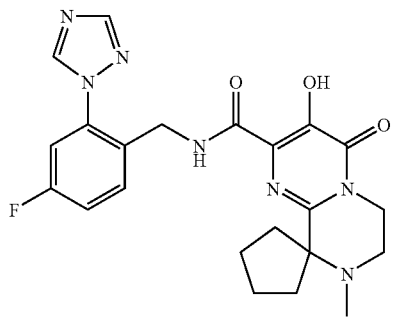

Spiro[cyclopentane-1,9'(6'H)-[4H]pyrazino[1,2-a]pyrimidine]-2'-carboxamide, N-[[4-fluoro-2-(1H-1,2,4-triazol-1-yl)phenyl]methyl]-7',8'-dihydro-3'-hydroxy-8'-methyl-4'-oxo-. $^1$H NMR (500 MHz, CHLOROFORM-D) δ ppm 2.04 (d, J=5.19 Hz, 4 H) 2.38-2.46 (m, 4 H) 2.82 (s, 3 H) 3.78 (t, J=6.26 Hz, 2 H) 4.28 (t, J=6.56 Hz, 2 H) 4.44 (d, J=6.71 Hz, 12H) 7.14 (m, 1 H), 7.24 (m, 1 H), 7.74 (m, 1H), 8.17 (s, 1 H), 8.51 (s, 1 H), 8.59 (m 1 H). $^{13}$C NMR (125 MHz, CHLOROFORM-D) δ 25.78, 37.50, 37.71, 39.19, 46.13, 73.32, 112.09, 112.29, 117.19, 117.36, 125.50, 128.24, 134.76, 134.83, 144.05, 146.68, 147.81, 152.56, 157.41, 161.33, 163.33, 167.59.

EXAMPLE 94

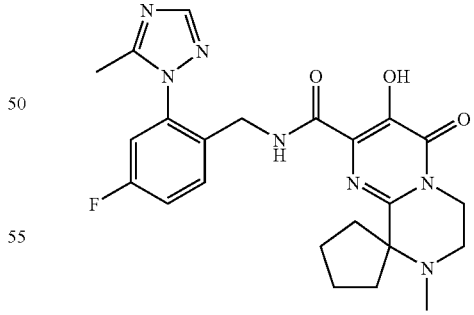

Spiro[cyclopentane-1,9'(6'H)-[4H]pyrazino[1,2-a]pyrimidine]-2'-carboxamide, N-[[4-fluoro-2-(5-methyl-1H-1,2,4-triazol-1-yl)phenyl]methyl]-7',8'-dihydro-3'-hydroxy-8'-methyl-4'-oxo-. $^1$H NMR (500 MHz, MeOD) δ ppm 1.94-2.03 (m, 2 H) 2.10 (m, 2 H) 2.47 (s, 3 H) 2.65 (m, 2 H) 3.07 (s, 3 H) 3.92,(m, 2 H) 4.29 (t, J=6.41 Hz, 2 H) 4.35-4.42 (m, 2 H) 7.36-7.42 (m, 2 H), 7.71 (m, 1), 8.10 (s, 1).

EXAMPLE 95

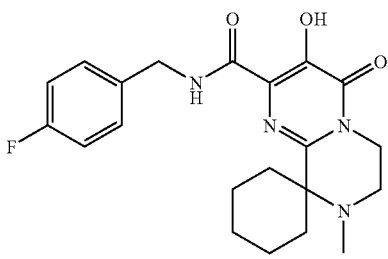

Spiro[cyclohexane-1,9'(6'H)-[4H]pyrazino[1,2-a]pyrimidine]-2'-carboxamide, N-[(4-fluorophenyl)methyl]-7',8'-dihydro-3'-hydroxy-8'-methyl-4'-oxo-. $^1$H NMR (500 MHz, DMSO-d$_6$) δ ppm 1.41-1.69 (br m, 4 H), 2.08 (m, 2), 2.50 (s, 3 H), 3.60 (m, 2), 3.91 (br m, 4 H), 4.05 (m, 2 H) 4.51 (d, J=6.10 Hz, 2 H) 7.12-7.20 (m, 2 H) 7.33-7.39 (m, 2 H), 9.34 (m, 1 H), 12.37 (br s, 1 H).

EXAMPLE 96

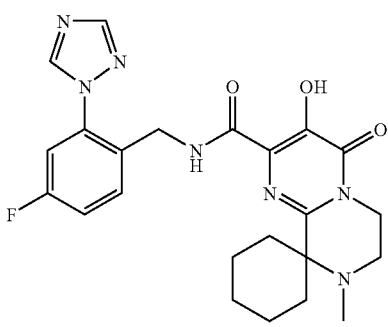

Spiro[cyclohexane-1,9'(6'H)-[4H]pyrazino[1,2-a]pyrimidine]-2'-carboxamide, N-[[4-fluoro-2-(1H-1,2,4-triazol-1-yl)phenyl]methyl]-7',8'-dihydro-3'-hydroxy-8'-methyl-4'-oxo-. $^1$H NMR (300 MHz, DMSO-d$_6$) δ ppm 1.41-1.68 (br m, 4 H), 2.04 (br m 2), 2.50 (s, 3 H) 3.46-3.56 (br m, 4 H), 3.90 (t, J=6.40, 2 H), 4.46 (d, J=6.10 Hz, 2 H) 7.43-7.54 (m, 1 H), 7.56-7.61 (m, 2 H), 8.27 (s, 1 H), 9.01 (s, 1 H).

EXAMPLE 97

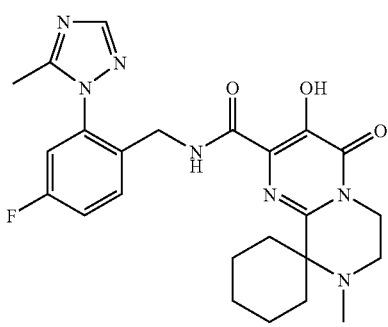

Spiro[cyclohexane-1,9'(6'H)-[4H]pyrazino[1,2-a]pyrimidine]-2'-carboxamide, N-[[4-fluoro-2-(5-methyl-1H-1,2,4-triazol-1-yl)phenyl]methyl]-7',8'-dihydro-3'-hydroxy-8'-methyl-4'-oxo-. $^1$H NMR (500 MHz, DMSO-d$_6$) δ ppm 1.60-1.69 (br m, 4 H) 2.22 (br m, 2 H) 2.35 (s, 3 H), 2.50 (s, 3 H), 3.60-4.04 (br m, 6 H), 4.26 (d, J=6.10 Hz, 2 H), 7.47 (m, 1 H) 7.57 (td, J=5.95, 3.05 Hz, 2 H), 8.09 (s, 1 H), 9,08 (m, 1 H), 12.06 (br s, 1 H).

EXAMPLE 98

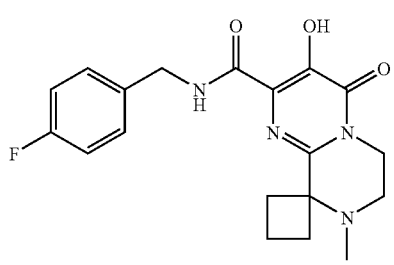

Spiro[cyclobutane-1,9'(6'H)-[4H]pyrazino[1,2-a]pyrimidine]-2'-carboxamide, N-[(4-fluorophenyl)methyl]-7',8'-dihydro-3'-hydroxy-8'-methyl-4'-oxo-. $^1$H NMR (500 MHz, DMSO-d,) δ ppm 1.80-1.87 (m, 1 H), 2.05-2.14 (m, 1 H) 2.46-2.54 (m, 2 H), 2.50 (s, 3 H) 2.71 (s, 2 H) 3.53 (t, J=5.95 Hz, 2 H) 3.95-4.04 (m, 2H) 4.53 (t, J=5.80 Hz, 2 H) 7.16-7.22 (m, 2 H) 7.37-7.43 (m, 2 H), 9.36 (m, 1 H), 12.59 (br s, 1 H).

EXAMPLE 99

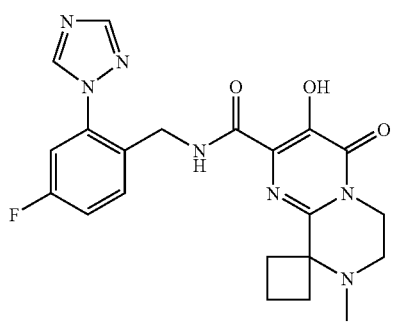

Spiro[cyclobutane-1,9'(6'H)-[4H]pyrazino[1,2-a]pyrimidine]-2'-carboxamide, N-[[4-fluoro-2-(1H-1,2,4-triazol-1-yl)phenyl]methyl]-7',8'-dihydro-3'-hydroxy-8'-methyl-4'-oxo-. $^1$H NMR (500 MHz, DMSO-d$_6$) δ ppm 1.87-1.89 (m, 1 H), 2.11-2.15 (m, 1 H), 2.50 (s, 3 H), 2.52-2.61 (m, 2 H) 2.74 (s, 2 H) 3.61 (t, J=5.80 Hz, 2 H), 4.00 (d, J=5.49 Hz, 2 H) 4.48 (m, 2 H), 7.43 (m, 1 H) 7.59 (m, 2 H), 8.29 (s, 1 H), 9.07 (s, 1 H), (9.27 (m, 1 H), 12.27 (br s, 1 H).

EXAMPLE 100

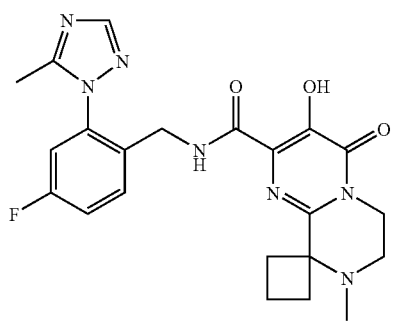

Spiro[cyclobutane-1,9'(6'H)-[4H]pyrazino[1,2-a]pyrimidine]-2'-carboxamide, N-[[4-fluoro-2-(5-methyl-1H-1,2,4-triazol-1-yl)phenyl]methyl]-7',8'-dihydro-3'-hydroxy-8'-methyl-4'-oxo- $^1$H NMR (500 MHz, DMSO-$d_6$) δ ppm 1.88-1.92 (m, 1 H), 2.10-2.16 (m, 1 H), 2.36 (s, 3 H) 2.50 (s, 3 H) 2.58-2.62 (m, 4 H) 2.78 (br s, 2) 3.65 (t, J=6.10 Hz, 2 H) 4.03 (br s, 2 H) 4.27 (d, J=6.41 Hz, 2 H), 7.46-7.49 (m, 1 H), 7.56-7.63 (m, 2 H), 8.08 (s, 1 H), 9.16 (m, 1 H), 12.31 (br s, 1 H).

EXAMPLE 101

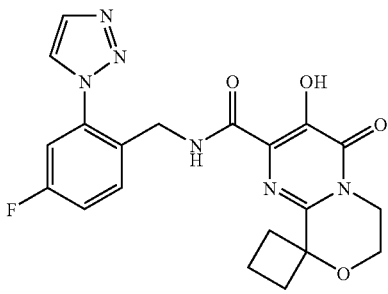

Spiro[cyclobutane-1,9'(4'H)-pyrimido[2,1-c][1,4]oxazine]-2'-carboxamide, N-[[4-fluoro-2-(1H-1,2,3-triazol-1-yl)phenyl]methyl]-6',7'-dihydro-3'-hydroxy-4'-oxo-. $^1$H NMR (400 MHz, CDCl$_3$) δ ppm: 11.95 (1 H, s), 8.80 (1 H, s), 7.92 (2 H, s), 7.76 (1 H, dd, J=8.6, 5.8 Hz), 7.20-7.27 (1 H, m), 7.11 (1 H, dd, J=8.5, 2.7 Hz), 4.46 (2 H, d, J=6.8 Hz), 3.95 (4 H, s), 2.69-2.78 (2 H, m), 2.27-2.38 (3 H, m), 2.27-2.38 (3 H, m), 2.03-2.14 (1 H, m), MS (ESI$^+$) m/e 427 [M+H$^+$], HRMS (ESI$^+$) calculated for C$_{20}$H$_{20}$FN$_6$O$_4$ [M+H$^+$]427.1530; found: 427.1547.

EXAMPLE 102

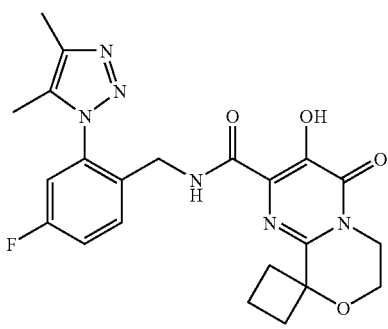

Spiro[cyclobutane-1,9'(4'H)-pyrimido[2,1-c][1,4]oxazine]-2'-carboxamide, N-[[2-(4,5-dimethyl-1H-1,2,3-triazol-1-yl)-4-fluorophenyl]methyl]-6',7'-dihydro-3'-hydroxy-4'-oxo-1H NMR 400 MHz (CDCl$_3$) δ (ppm): 11.97 (1 H, s), 8.54 (1 H, m), 7.74 (1 H, dd, J=8.6, 5.8 Hz), 7.25-7.32 (1 H, m), 7.01 (1 H, dd, J=8.3, 2.5 Hz), 4.30 (2 H, d, J=6.6 Hz), 3.95-4.02 (4 H, m), 2.73-2.82 (2 H, m), 2.29-2.40 (6 H, m), 2.23 (3 H, s), 2.13 (1 H, m),.

EXAMPLE 103

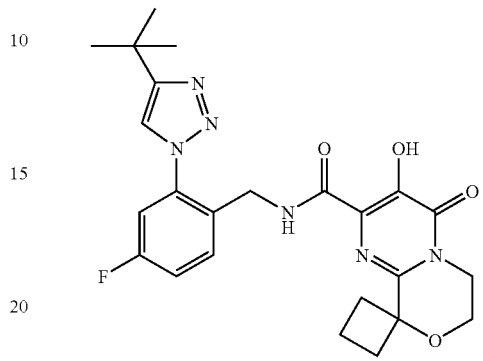

Spiro[cyclobutane-1,9'(4'H)-pyrimido[2,1-c][1,4]oxazine]-2'-carboxamide, N-[[2-[4-(1,1-dimethylethyl)-1H-1,2,3-triazol-1-yl]-4-fluorophenyl]methyl]-6',7'-dihydro-3'-hydroxy-4'-oxo- $^1$H NMR (400 MHz, CDCl$_3$) δ ppm: 12.00 (1 H, s), 8.95-9.04 (1 H, m), 7.72 (1 H, dd, J=8.6, 6.1 Hz), 7.61 (1 H, s), 7.19 (1 H, td, J=8.2, 2.8 Hz), 7.11 (1 H, dd, J=8.7, 2.7 Hz), 4.50 (2 H, d, J=6.8 Hz), 3.95 (4 H, s), 2.71-2.81 (2 H, m), 2.26-2.37 (3 H, m), 2.02-2.12 (1 H, m), 1.42 (9 H, s), MS (ESI$^+$) m/e 483 [M+H$^+$], HRMS (ESI$^+$) calculated for C$_{24}$H$_{28}$FN$_6$O$_4$ [M+H$^+$]483.2156; found: 483.2179.

EXAMPLE 104

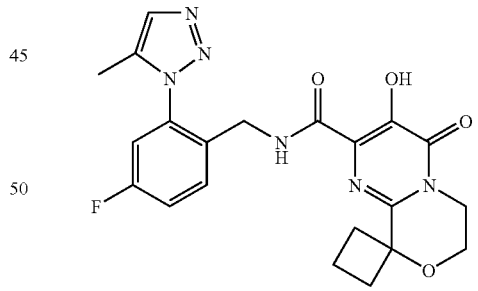

Spiro[cyclobutane-1,9'(4'H)-pyrimido[2,1-c][1,4]oxazine]-2'-carboxamide, N-[[4-fluoro-2-(5-methyl-1H-1,2,3-triazol-1-yl)phenyl]methyl]-6',7'-dihydro-3'-hydroxy-4'-oxo- $^1$H NMR (400 MHz, CDCl$_3$) δ ppm: 11.90 (1 H, s), 8.49 (1 H, t, J=6.3 Hz), 7.73 (1 H, dd, J=8.6, 5.8 Hz), 7.65 (1 H, s), 7.22-7.30 (1 H, m), 7.01 (1 H, dd, J=8.3, 2.8 Hz), 4.26 (2 H, d, J=6.6 Hz), 3.95 (4 H, s), 2.70-2.80 (2 H, m), 2.27-2.38 (6 H, m), 2.05-2.17 (1 H, m), LCMS ($^+$ESI, M+H$^+$) m/z 441.

EXAMPLE 105

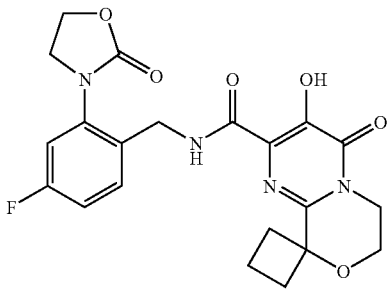

Spiro[cyclobutane-1,9'(4'H)-pyrimido[2,1-c][1,4]ox-azine]-2'-carboxamide, N-[[4-fluoro-2-(2-oxo-3-oxazolidinyl)phenyl]methyl]-6',7'-dihydro-3'-hydroxy-4'-oxo-. $^{1}$H NMR 400 MHz (MeOD) δ (ppm): 7.56 (1 H, m), 7.22 (1 H, m), 7.12 (1 H, m), 4.59 (2 H, m), 4.10 (2 H, m), 3.99 (2 H, m), 3.90 (2 H, m), 2.80 (2H, m), 2.80 (2H, m), 2.24 (2H, m), 2.13 (2 H, m), 2.02 (2 H, m). HRMS (ESI+) calculated for $C_{21}H_{22}FN_4O_6$ [M+H$^+$]445.1523; found: 445.1506.

EXAMPLE 106

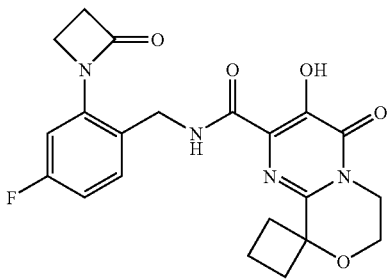

Spiro[cyclobutane-1,9'(4'H)-pyrimido[2,1-c][1,4]ox-azine]-2'-carboxamide, N-[[4-fluoro-2-(2-oxo-1-azetidinyl)phenyl]methyl]-6',7'-dihydro-3'-hydroxy-4'-oxo-. $^{1}$H NMR 400 MHz (MeOD) δ (ppm): 7.61 (1 H, m), 7.04 (2 H, m), 4.65 (2 H, m), 4.01(2 H, m), 3.96 (2 H, m), 3.85 (2 H, m), 3.18 (2 H, m), 2.78 (2 H, m), 2.31 (2 H, m), 2.21-2.02 (2 H, m). HRMS (ESI$^+$) calculated for $C_{21}H_{22}FN_4O_6$ [M+H$^+$] 429.1574; found: 429.1561.

EXAMPLE 107

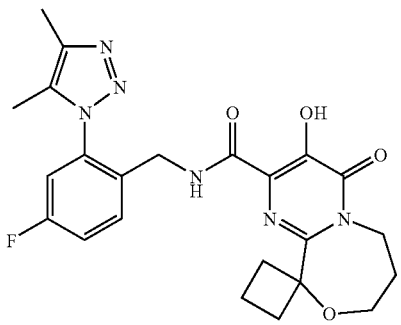

Spiro[cyclobutane-1,10'(4'H)-[6H]pyrimido[2,1-c][1,4]oxazepine]-2'-carboxamide, N-[[2-(4,5-dimethyl-1H-1,2,3-triazol-1-yl)-4-fluorophenyl]methyl]-7',8'-dihydro-3'-hydroxy-4'-oxo- $^{1}$H NMR (400 MHz, CDCl$_3$) δ ppm: 12.02 (1 H, s), 8.34 (1 H, t, J=6.3 Hz), 7.67 (1 H, dd, J=8.6, 5.8 Hz), 7.20-7.28 (1 H, m), 6.97 (1 H, dd, J=8.3, 2.5 Hz), 4.36 (2 H, brs), 4.26 (2 H, d, J=6.6 Hz), 3.89 (2 H, t, J=5.7 Hz), 2.79 (2 H, t, J=8.3 Hz), 2.39-2.48 (2 H, m), 2.35 (3 H, s), 2.18 (3 H, s), 1.73-1.95 (4 H, m), LCMS ($^+$ESI, M+H$^+$) m/z 469.

EXAMPLE 108

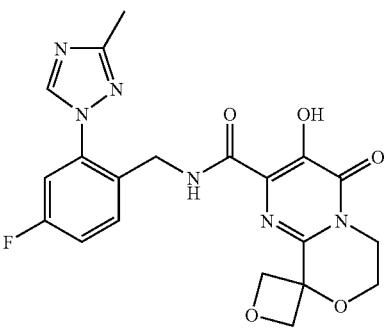

Spiro[oxetane-3,9'(4'H)-pyrimido[2,1-c][1,4]oxazine]-2'-carboxamide, N-[[4-fluoro-2-(3-methyl-1H-1,2,4-triazol-1-yl)phenyl]methyl]-6',7'-dihydro-3'-hydroxy-4'-oxo-. A suspension of N-(4-fluoro-2-(3-methyl-1H-1,2,4-triazol-1-yl) benzyl)-9-(chloromethyl)-3-hydroxy-9-(hydroxymethyl)-4-oxo-4,6,7,9-tetrahydropyrimido[2,1-c][1,4]oxazine-2-carboxamide (0.220 g, 0.459 mmol) and tetrabutyl ammonium bromide (0.075 g, 0.23 mmol) in 1.0 N NaOH solution (2.5 mL) and water (2.5 mL) was heated (80° C., oil bath) for 4 hrs. The reaction was quenched with 1.0 N HCl solution (4 mL), and extracted into ethyl acetate (2×10 mL) and CH$_2$Cl$_2$ (10 mL). The combined extracts were dried (Na$_2$SO$_4$), filtered, and concentrated in-vacuo. The crude material was dissolved in dimethylfomamide (3 mL) and purified by C-18 reverse phase column chromatography, eluting with 10% -30% acetonitrile in water. Product fractions were concentrated to dryness by rotary evaporator, or optionally reduced in volume and extracted with CH$_2$Cl$_2$. The product was then triturated with 95% ethanol or, optionally, AcCN. The resulting solid was collected by filtration to give the title compound as crystalline white solid: $^{1}$H NMR (500 MHz, CDCl$_3$) δ ppm 12.38 (1H, s), 8.84 (1H, t, J=6.41 Hz), 8.31 (1H, s), 7.70 (1H, dd, J=8.70, 5.95 Hz), 7.17 (1H, td, J=8.24, 2.75 Hz), 7.08 (1H, dd, J=8.55, 2.44 Hz), 5.09 (2H, d, J=6.41 Hz), 4.74 (2H, d, J=6.41 Hz), 4.51 (2H, d, J=6.71 Hz), 4.01 (4H, s), 2.56 (3H, s); $^{13}$C NMR (126 MHz, CDCl$_3$) δ ppm 168.00, 163.19, 161.23, 157.40, 147.55, 145.78, 144.02, 137.11, 137.03, 134.27, 134.20, 128.33, 125.69, 116.59, 116.42, 111.99, 111.79, 81.76, 59.90, 42.20, 39.37, 13.90; HRMS (ESI) calcd for $C_{20}H_{20}N_6O_5F$ (M+H) 443.1479, found 443.1477, Elem. Anal. calcd for $C_{20}H_{19}N_6O_5F$·0.1 H$_2$O: C54.08, H 4.36; N 18.92, found: C 54.04, H 4.07, N18.99.

EXAMPLE 109

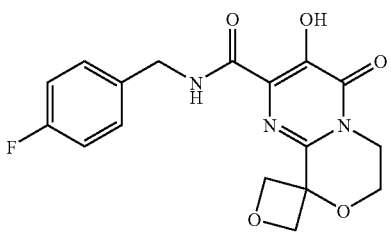

Spiro[oxetane-3,9'(4'H)-pyrimido[2,1-c][1,4]oxazine]-2'-carboxamide, N-[(4-fluorophenyl)methyl]-6',7'-dihydro-3'-hydroxy-4'-oxo-. $^1$H NMR (500 MHz, CDCl$_3$) δ ppm 12.30 (1H, s), 8.10 (1H, br), 7.29-7.36 (2H, m), 7.02-7.08 (2H, m, J=8.55, 8.55 Hz), 5.02 (2H, d, J=6.41 Hz), 4.78 (2H, d, J=6.41 Hz), 4.61 (2H, d, J=6.41 Hz), 4.01 (4H, s); HRMS (ESI) calcd for C$_{17}$H$_{17}$N$_3$O$_5$F (M+H) 362.1152, found 362.1148. HPLC purity: 98% AP (rt=1.92 min). White solid

EXAMPLE 110

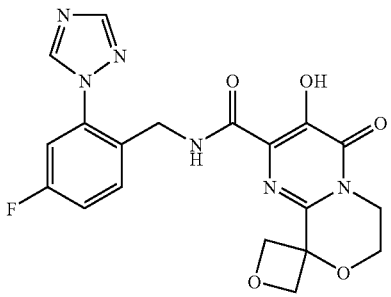

Spiro[oxetane-3,9'(4'H)-pyrimido[2,1-c][1,4]oxazine]-2'-carboxamide, N-[[4-fluoro-2-(1H-1,2,4-triazol-1-yl)phenyl]methyl]-6',7'-dihydro-3'-hydroxy-4'-oxo-. $^1$H NMR (500 MHz, CDCl$_3$) δ ppm 12.10 (1H, s), 9.29 (1H, t, J=6.56 Hz), 8.45 (1H, s), 8.36 (1H, s), 7.70 (1H, dd, J=8.70, 5.95 Hz), 7.21 (1H, td, J=8.16, 2.59 Hz), 7.10 (1H, dd, J=8.39, 2.59 Hz), 5.14 (2H, d, J=6.41 Hz), 4.79 (2H, d, J=6.71 Hz), 4.47 (2H, d, J=6.71 Hz), 4.00 (4H, s); $^{13}$C NMR (126 MHz, CDCl$_3$) δ ppm 167.62, 161.24, 157.40, 153.43, 147.18, 145.97, 143.94, 134.27, 134.20, 128.63, 128.60, 125.85, 117.05, 116.89, 112.79, 112.59, 82.18, 59.99, 42.17, 39.40; HRMS (ESI) calcd for C$_{19}$H$_{18}$N$_6$O$_5$F (M+H) 429.1323, found 429.1330. HPLC rt=1.60 min. White crystalline solid

EXAMPLE 111

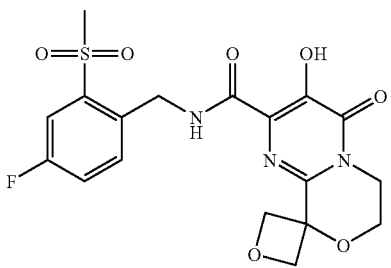

Spiro[oxetane-3,9'(4'H)-pyrimido[2,1-c][1,4]oxazine]-2'-carboxamide, N-[[4-fluoro-2-(methylsulfonyl)phenyl]methyl]-6',7'-dihydro-3'-hydroxy-4'-oxo-. $^1$H NMR (500 MHz, CDCl$_3$) δ ppm 11.98 (1H, s), 8.78 (1H, t, J=6.56 Hz), 7.76 (1H, dd, J=7.93, 2.75 Hz), 7.69 (1H, dd, J=8.55, 5.19 Hz), 7.34 (1H, td, J=7.93, 2.75 Hz), 5.06 (2H, d, J=6.71 Hz), 4.88 (2H, d, J=6.71 Hz), 4.77 (2H, d, J=6.71 Hz), 4.00 (4H, s), 3.22 (3H, s); $^{13}$C NMR (126 MHz, CDCl$_3$) δ ppm 168.10, 163.08, 157.31, 147.33, 146.21, 140.79, 134.57, 134.51, 132.73, 132.70 125.54, 121.50, 121.34, 117.64, 117.44, 81.88, 59.93, 45.01, 42.15, 40.34; HRMS (ESI) calcd for C$_{18}$H$_{19}$N$_3$O$_7$FS (M+H) 440.0928, found 440.0937. Elem. Anal. calcd for C$_{18}$H$_{18}$N$_3$O$_7$FS.0.1 CH$_2$Cl$_2$: C 48.53, H 4.10, N 9.38, found: C 48.29, H 3.79, N 9.33. HPLC rt=1.77 min. White solid

EXAMPLE 112

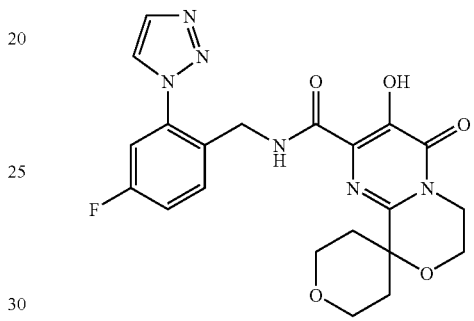

Spiro[4H-pyran-4,9'(4'H)-pyrimido[2,1-c][1,4]oxazine]-2'-carboxamide, N-[[4-fluoro-2-(1H-1,2,3-triazol-1-yl)phenyl]methyl]-2,3,5,6,6',7'-hexahydro-3'-hydroxy-4'-oxo-. $^1$H NMR 400 MHz (CDCl$_3$) δ (ppm): 11.94 (1 H, s), 8.55 (1 H, m), 7.98 (1 H, s), 7.95 (1 H, s) 7.71 (1 H, dd, J=8.6, 5.8 Hz), 7.24-7.30 (1 H, m), 7.16 (1 H, dd, J=8.3, 2.5 Hz), 4.51 (2 H, d, J=6.8 Hz), 4.05 (4 H, s), 3.87-3.97 (2 H, m), 3.77-3.87 (2 H, m), 2.45 (2 H, td, J=13.2, 5.2 Hz), 1.81 (2 H, d, J=13.6 Hz).

EXAMPLE 113

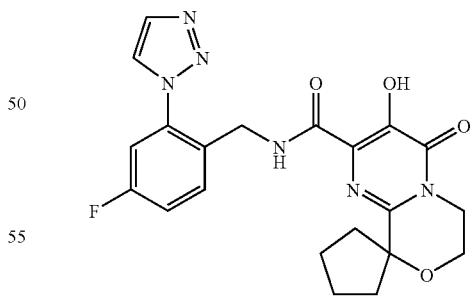

Spiro[cyclopentane-1,9'(4'H)-pyrimido[2,1-c][1,4]oxazine]-2'-carboxamide, N-[[4-fluoro-2-(1H-1,2,3-triazol-1-yl)phenyl]methyl]-6',7'-dihydro-3'-hydroxy-4'-oxo-. $^1$H NMR 400 MHz (CDCl$_3$) δ (ppm): 11.87 (1 H, s), 8.68 (1 H, m), 7.95 (1H, d, J=1.2 Hz), 7.94 (1 H, d, J=1.2 Hz), 7.76 (1 H, dd, J=8.6, 5.8 Hz), 7.26 (1 H, dd, J=8.6, 2.5 Hz), 7.13 (1 H, dd, J=8.5, 2.7 Hz), 4.47 (2 H, d, J=6.8 Hz), 3.95-4.05 (4 H, m), 2.25-2.35(2 H, m), 2.00-2.11 (4 H, m), 1.89(2 H, m).

EXAMPLE 114

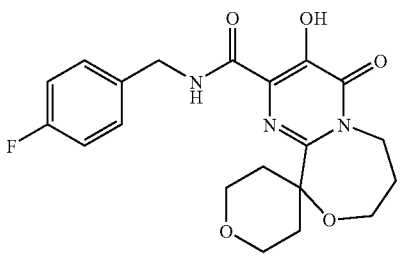

Spiro[4H-pyran-4,10'(4'H)-[6H]pyrimido[2,1-c][1,4]oxazepine]-2'-carboxamide, N-[(4-fluorophenyl)methyl]-2,3,5,6,7',8'-hexahydro-3'-hydroxy-4'-oxo-. ¹HNMR 400 MHz (CDCl₃) δ (ppm): 1.85 (2H, m, CH₂), 2.05 (2H, m, CH₂), 2.3 (2H, m, CH₂), 3.75 (2H, m, CH₂), 3.8-3.9 (4H, m, 2×CH₂), 4.5-4.7 (4H, m 2×CH₂), 7.1 (2H, m, aromatics), 7.35 (2H, m, aromatics), 7.75 (1H, broad t, NH), 12.1 (1H, s, OH). MS (ESI⁺) m/e 404 [M+H⁺].

EXAMPLE 115

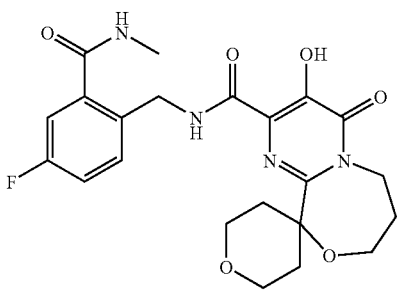

Spiro[4H-pyran-4,10'(4'H)-[6H]pyrimido[2,1-c][1,4]oxazepine]-2'-carboxamide, N-[[4-fluoro-2-[(methylamino)carbonyl]phenyl]methyl]-2,3,5,6,7',8'-hexahydro-3'-hydroxy-4'-oxo-. White crystals; mp 211° C. (dec.) (ethyl acetate). ¹HNMR 400 MHz (CDCl₃) δ (ppm): 1.87 (2H, m, CH₂), 1.99 (2H, m, CH₂), 2.43 (2H, m, CH₂), 3.05 (3H, d, J=4.8 Hz, NCH₃), 3.72 (2H, m, CH₂), 3.8 -3.9 (4H, m, 2×CH₂), 4.55 (2H, m, CH₂), 4.61 (2H, d, J=6.5 Hz, NCH₂), 6.24 (1H, m, NH), 7.15 (1H, m, aromatic), 7.21 (1H, dd, J=2.7 Hz and J=8.6 Hz, aromatic), 7.52 (1H, dd, J=5.4 Hz and J=8.6 Hz, aromatic), 9.00 (1H, broad t, NH), 12.18 (1H, s, OH). MS (ESI⁺) m/e 461 [M+H⁺].

EXAMPLE 116

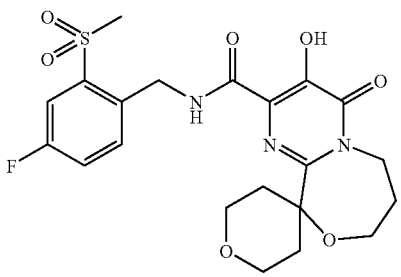

Spiro[4H-pyran-4,10'(4'H)-[6H]pyrimido[2,1-c][1,4]oxazepine]-2'-carboxamide, N-[[4-fluoro-2-(methylsulfonyl)phenyl]methyl]-2,3,5,6,7',8'-hexahydro-3'-hydroxy-4'-oxo-. White crystals; mp 257° C. (dec.) (ethanol). ¹HNMR 400 MHz (CDCl₃) δ (ppm): 1.85 (2H, m, CH₂), 1.99 (2H, m, CH₂), 2.33 (2H, m, CH₂), 3.22 (3H, s, SCH₃), 3.71 (2H, m, CH₂), 3.75-3.9 (4H, m, 2×CH₂), 4.56 (2H, m, CH₂), 4.85 (2H, d, J=6.8 Hz, NCH₂), 7.37 (1H, m, aromatic), 7.72 (1H, dd, J=5.0 Hz and J=8.6 Hz, aromatic), 7.78 (1H, dd, J=2.6 Hz and J=8.3 Hz, aromatic), 8.55 (1H, broad t, NH), 11.87 (1H, s, OH). Anal. Calcd for $C_{21}H_{24}FN_3O_7S$: C 52.38, H 5.02, N 8.72; Found: C 52.17, H 5.21, N 8.44.

EXAMPLE 117

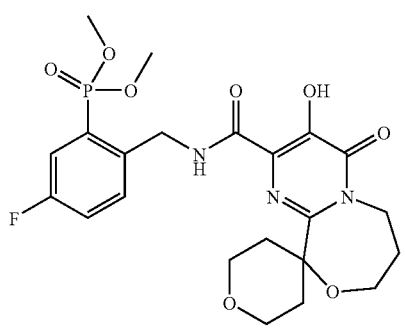

Phosphonic acid, [5-fluoro-2-[[[(2,3,5,6,7',8'-hexahydro-3'-hydroxy-4'-oxospiro[4H-pyran-4,10'(4'H) -[6H]pyrimido [2,1-c][1,4]oxazepin]-2'-yl)carbonyl]amino]methyl]phenyl]-, dimethyl ester. White crystals; mp 234° C. (dec.) (ethyl acetate). ¹HNMR 400 MHz (CDCl₃) δ (ppm): 1.85 (2H, m, CH₂), 1.99 (2H, m, CH₂), 2.41 (2H, m, CH₂), 3.71 (2H, m, CH₂), 3.8-3.9 (4H, m, 2×CH₂), 3.86 (3H, s, OCH₃), 3.88 (3H, s, OCH₃), 4.56 (2H, m, CH₂), 4.78 (2H, d, J=6.6 Hz, NCH₂), 7.26 (1H, m , aromatic), 7.49 (1H, m, aromatic), 7.63 (1H, m, aromatic), 9.02 (1H, broad t, NH), 12.18 (1H, s, OH). MS (ESI⁺) m/e 512 [M+H⁺].

EXAMPLE 118

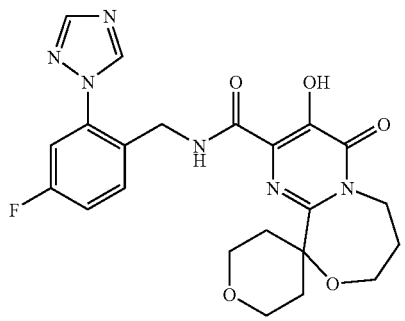

Spiro[4H-pyran-4,10'(4'H)-[6H]pyrimido[2,1-c][1,4]oxazepine]-2'-carboxamide, N-[[4-fluoro-2-(1H-1,2, 4-triazol-1-yl)phenyl]methyl]-2,3,5,6,7',8'-hexahydro-3'-hydroxy-4'-oxo-. White crystals; mp 247° C. (dec.) (ethyl acetate). ¹HNMR 400 MHz (CDCl₃) δ (ppm): 1.89 (2H, m, CH₂), 2.01 (2H, m, CH₂), 2.43 (2H, m, CH₂), 3.74 (2H, m, CH₂), 3.8-3.9 (4H, m, 2×CH₂), 4.47 (2H, d, J=6.9 Hz, NCH₂), 4.56 (2H, m, CH₂), 7.14 (1H, dd , J=2.5 Hz and J=8.6 Hz, aromatic), 7.24 (1H, m, aromatic), 7.72 (1H, dd, J=6.0 Hz and J=8.6 Hz, aromatic), 8.31 (1H, s, CH), 8.49 (1H, s, CH), 9.01 (1H, broad t, NH), 11.99 (1H, s, OH). MS (ESI⁺) m/e 471 [M+H⁺]. Anal. Calcd for $C_{22}H_{23}FN_6O_5 \cdot 0.5\ H_2O$: C 55.11, H 5.05, N 17.53; Found: C 55.17, H 4.91, N 17.02.

EXAMPLE 119

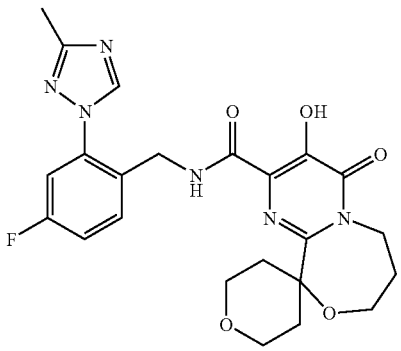

Spiro[4H-pyran-4,10'(4'H)-[6H]pyrimido[2,1-c][1,4]oxazepine]-2'-carboxamide, N-[[4-fluoro-2-(3-methyl-1H-1,2,4-triazol-1-yl)phenyl]methyl]-2,3,5,6,7',8'-hexahydro-3'-hydroxy-4'-oxo-. White crystals; mp 240° C. (dec.) (ethyl acetate). ¹HNMR 400 MHz (CDCl₃) δ (ppm): 1.86 (2H, m, CH₂), 2.01 (2H, m, CH₂), 2.37 (2H, m, CH₂), 2.61 (3H, s, CH₃), 3.72 (2H, m, CH₂), 3.8-3.9 (4H, m, 2×CH₂), 4.51 (2H, d, J=6.9 Hz, NCH₂), 4.56 (2H, m, CH₂), 7.12 (1H, dd, J=2.5 Hz and J=8.6 Hz, aromatic), 7.20 (1H, m, aromatic), 7.72 (1H, dd, J=5.9 Hz and J=8.6 Hz, aromatic), 8.34 (1H, s, CH), 8.72 (1H, broad t, NH), 12.27 (1H, s, OH). MS (ESI⁺) m/e 485 [M+H⁺]. Anal. Calcd for $C_{23}H_{25}FN_6O_5$: C 57.02, H 5.20, N 17.35; Found: C 56.92, H 5.09, N 16.74.

EXAMPLE 120

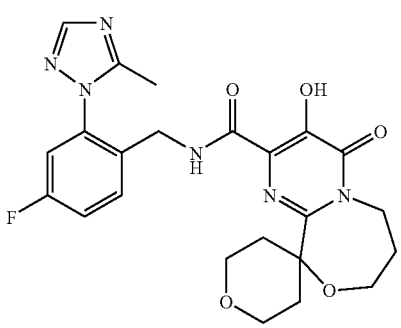

Spiro[4H-pyran-4,10'(4'H)-[6H]pyrimido[2,1-c][1,4]oxazepine]-2'-carboxamide, N-[[4-fluoro-2-(5-methyl-1H-1,2,4-triazol-1-yl)phenyl]methyl]-2,3,5,6,7',8'-hexahydro-3'-hydroxy-4'-oxo-. White crystals; mp 204° C. (ethyl acetate). ¹HNMR 400 MHz (CDCl₃) δ (ppm): 1.87 (2H, m, CH₂), 2.01 (2H, m, CH₂), 2.5 (2H, m, CH₂), 2.52 (3H, s, CH₃), 3.74 (2H, m, CH₂), 3.8-3.9 (4H, m, 2×CH₂), 4.32 (2H, d, J=6.6 Hz, NCH₂), 4.56 (2H, m, CH₂), 7.05 (1H, dd, J=2.5 Hz and J=8.3 Hz, aromatic), 7.26 (1H, m, aromatic), 7.70 (1H, dd, J=6.1 Hz and J=8.6 Hz, aromatic), 8.14 (1H, s, CH), 8.76 (1H, broad t, NH), 11.96 (1H, s, OH). Anal. Calcd for $C_{23}H_{25}FN_6O_5$: C 57.02, H 5.20, N 17.34; Found: C 52.08, H 5.35, N 17.21.

EXAMPLE 121

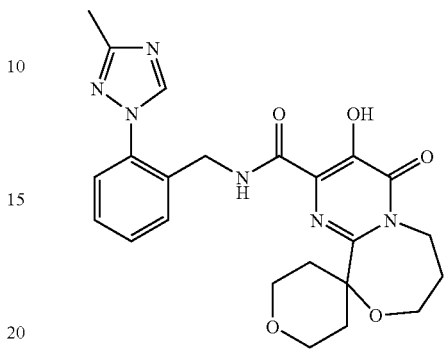

Spiro[4H-pyran-4,10'(4'H)-[6H]pyrimido[2,1-c][1,4]oxazepine]-2'-carboxamide, 2,3,5,6,7,8'-hexahydro-3'-hydroxy-N-[[2-(3-methyl-1H-1,2,4-triazol-1-yl)phenyl]methyl]-4'-oxo-. White crystals; mp 247° C. (dec.) (ethanol). ¹HNMR 400 MHz (CDCl₃) δ (ppm): 1.86 (2H, m, CH₂), 2.0 (2H, m, CH₂), 2.38 (2H, m, CH₂), 2.61 (3H, s, CH₃), 3.73 (2H, m, CH₂), 3.85-3.9 (4H, m, 2×CH₂), 4.53 (2H, d, J=6.9 Hz, NCH₂), 4.56 (2H, m, CH₂), 7.35-7.4 (1H, m, aromatic), 7.45-7.52 (2H, m, aromatics), 7.69-7.74 (1H, m, aromatic), 8.33 (1H, s, CH), 8.74 (1H, broad t, NH), 12.33 (1H, s, OH). Anal. Calcd for $C_{23}H_{26}N_6O_5$: C 59.21, H 5.61, N 18.01; Found: C 59.46, H 5.50, N 17.80.

EXAMPLE 122

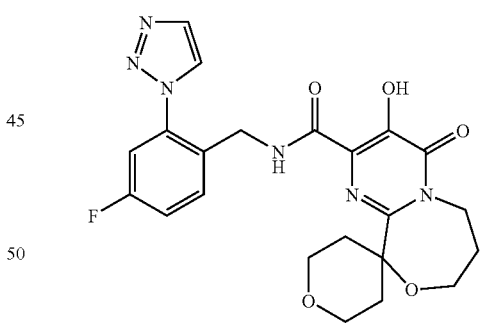

Spiro[4H-pyran-4,10'(4'H)-[6H]pyrimido[2,1-c][1,4]oxazepine]-2'-carboxamide, N-[[4-fluoro-2-(1H-1,2,3-triazol-1-yl)phenyl]methyl]-2,3,5,6,7',8'-hexahydro-3'-hydroxy-4'-oxo-. White crystals; mp 239° C. (dec.) (ethyl acetate). ¹HNMR 400 MHz (CDCl₃) δ (ppm): 1.90 (2H, m, CH₂), 1.99 (2H, m, CH₂), 2.45 (2H, broad m, CH₂), 3.74 (2H, m, CH₂), 3.84-3.95 (4H, m, 2×CH₂), 4.48 (2H, d, J=6.8 Hz, NCH₂), 4.58 (2H, m, CH₂), 7.14 (1H, dd, J=2.5 Hz and J=8.6 Hz, aromatic), 7.26 (1H, m, aromatic), 7.73 (1H, dd, J=6.0 Hz and J=8.6 Hz, aromatic), 7.95 (1H, s, CH), 7.97 (1H, s, CH), 8.75 (1H, broad t, NH), 11.97 (1H, s, OH). MS (ESI⁺) m/e 471 [M+H⁺].

EXAMPLE 123

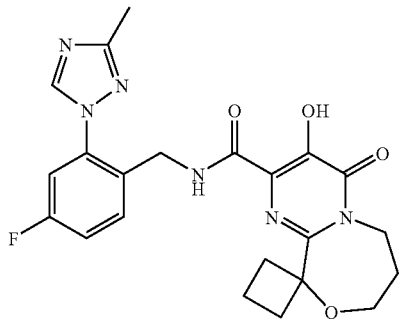

Spiro[cyclobutane-1,10'(4'H)-[6H]pyrimido[2,1-c][1,4]oxazepine]-2'-carboxamide, N-[[4-fluoro-2-(3-methyl-1H-1,2,4-triazol-1-yl)phenyl]methyl]-7',8'-dihydro-3'-hydroxy-4'-oxo-. $^1$H NMR (500 MHz, CDCl$_3$) δ ppm 12.24 (1H, s), 8.73 (1H, br), 8.35 (1H, br), 7.70 (1H, dd, J=8.55, 5.80 Hz), 7.15-7.22 (1H, m), 7.08 (1H, d, J=8.24 Hz), 4.49 (2H, d, J=6.71 Hz), 4.38 (2H, br), 3.89 (2H, t, J=5.34 Hz), 2.80 (2H, br), 2.49 (3H, s), 2.39-2.47 (2H, m), 1.86-1.93 (1H, m), 1.79-1.86 (2H, m), 1.68-1.75 (1H, m); $^{13}$C NMR (126 MHz, CDCl$_3$) δ ppm 168.33, 163.20, 162.01, 158.53, 150.67, 147.81, 143.86, 136.80, 136.73, 134.33, 134.26, 128.55, 124.54, 116.92, 116.76, 112.00, 111.80, 82.11, 64.54, 40.77, 39.06, 32.00, 28.65, 13.88, 12.72; HRMS calcd for C$_{22}$H$_{24}$N$_6$O$_4$F (M+H) 455.1843, found 455.1849. HPLC rt=2.12 min. White crystalline solid

EXAMPLE 124

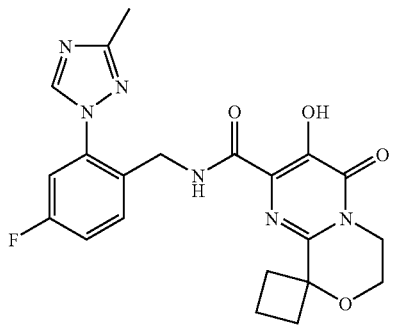

Spiro[cyclobutane-1,9'(4'H)-pyrimido[2,1-c][1,4]oxazine]-2'-carboxamide, N-[[4-fluoro-2-(3-methyl-1H-1,2,4-triazol-1-yl)phenyl]methyl]-6',7'-dihydro-3'-hydroxy-4'-oxo-. $^1$H NMR (500 MHz, CDCl$_3$) δ ppm 12.18 (1H, s), 8.66 (1H, br m), 8.32 (1H, s), 7.69-7.75 (1H, m), 7.18 (1H, td, J=8.16, 2.59 Hz), 7.04-7.11 (1H, m), 4.51 (2H, d, J=6.71 Hz), 3.96 (4H, s), 2.64-2.72 (2H, m), 2.50 (3H, s), 2.30-2.38 (2H, m), 2.07-2.16 (1H, m), 2.00-2.07 (1H, m); $^{13}$C NMR (126 MHz, CDCl$_3$) δ ppm 168.33, 163.20, 162.01, 158.53, 150.67, 147.81, 143.86, 136.80, 134.33, 134.26, 128.55, 124.54, 116.92, 116.76, 112.00, 111.80, 82.11, 64.54, 40.77, 39.06, 32.00, 28.65, 13.88, 12.72; HRMS calcd for C$_{21}$H$_{22}$N$_6$O$_4$F (M+H) 441.1687, found 441.1679. HPLC rt=2.07 min. White crystalline solid

EXAMPLE 125

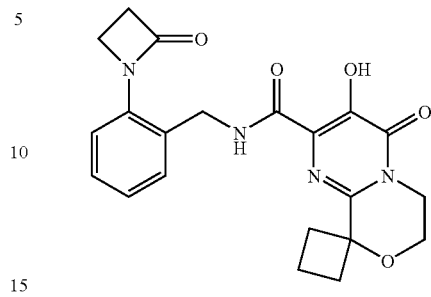

Spiro[cyclobutane-1,9'(4'H)-pyrimido[2,1-c][1,4]oxazine]-2'-carboxamide, 6',7'-dihydro-3'-hydroxy-4'-oxo-N-[[2-(2-oxo-1-azetidinyl)phenyl]methyl]-. $^1$H NMR (500 MHz, CDCl$_3$) δ ppm 12.28 (1H, br), 9.15 (1H, t, J=6.10 Hz), 7.62 (1H, d, J=7.63 Hz), 7.32 (1H, t, J=7.63 Hz), 7.22 (1H, t, J=7.48 Hz), 7.06 (1H, d, J=7.93 Hz), 4.64 (2H, d, J=6.71 Hz), 3.92-3.98 (4H, m), 3.76 (2H, t, J=4.43 Hz), 3.15 (2H, t, J=4.12 Hz), 2.67-2.74 (2H, m), 2.25-2.32 (2H, m), 2.12-2.21 (1H, m), 1.96-2.05 (1H, m); $^{13}$C NMR (126 MHz, CDCl$_3$) δ ppm 168.38, 165.98, 157.89, 150.28, 146.64, 136.09, 132.30, 131.12, 128.84, 126.73, 126.17, 120.50, 78.90, 58.58, 42.47, 39.88, 35.44, 34.68, 13.65; HRMS calcd for C$_{21}$H$_{23}$N$_4$O$_5$ (M+H) 411.1668, found 411.1682; Elem. Anal. calcd for C$_{21}$H$_{22}$N$_4$O$_5$: C 61.45, H 5.40, N 13.65, found: C 61.43, H 5.56, N 13.62. HPLC rt=2.24 min. White crystalline solid

EXAMPLE 126

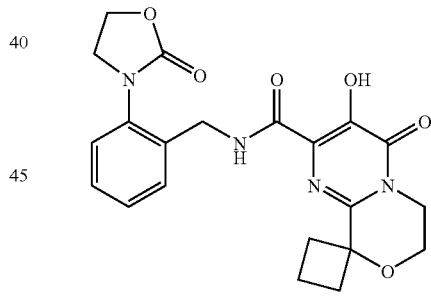

Spiro[cyclobutane-1,9'(4'H)-pyrimido[2,1-c][1,4]oxazine]-2'-carboxamide, 6',7'-dihydro-3'-hydroxy-4'-oxo-N-[[2-(2-oxo-3-oxazolidinyl)phenyl]methyl]-. $^1$H NMR (500 MHz, CDCl$_3$) δ ppm 12.14 (1H, s), 8.63 (1H, t, J=5.95 Hz), 7.56 (1 H, d J=7.32 Hz), 7.32-7.40 (2H, m), 7.24-7.27 (1H, m), 4.61 (2 H, d, J=6.41 Hz), 4.57 (2H, t, J=7.93 Hz), 4.07 (2H, t, J=7.93 Hz), 3.92-3.99 (4H, m), 2.69 (2 H, ddd J=12.13, 9.23, 6.10 Hz), 2.23-2.30 (2H, m), 2.08-2.17 (1H, m), 1.96-2.05 (1H, m); $^{13}$C NMR (126 MHz, CDCl$_3$) δ ppm 168.35, 157.84, 157.49, 150.51, 146.66, 136.05, 135.17, 131.29, 129.20, 128.71, 125.91, 125.20, 79.00, 62.62, 58.56, 48.12, 42.53, 38.96, 34.65, 13.79; HRMS calcd for C$_{21}$H$_{23}$N$_4$O$_6$ (M+H) 427.1618, found 427.1616; Elem. Anal. calcd for C$_{21}$H$_{22}$N$_4$O$_6$: C 59.15, H 5.20, N 13.13, found: C 59.10, H 4.99, N 13.26. HPLC rt=1.97 min. Crystalline solid

EXAMPLE 127

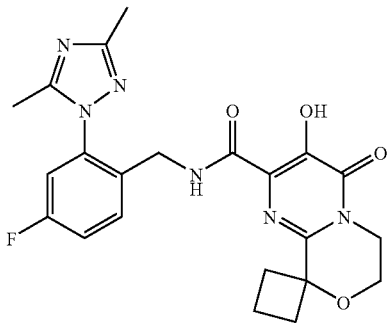

Spiro[cyclobutane-1,9'(4'H)-pyrimido[2,1-c][1,4]oxazine]-2'-carboxamide, N-[[2-(3,5-dimethyl-1H-1,2,4-triazol-1-yl)-4-fluorophenyl]methyl]-6',7'-dihydro-3'-hydroxy-4'-oxo-. $^1$H NMR (500 MHz, CDCl$_3$) δ ppm 12.09 (1H, s), 8.36 (1H, t, J=6.26 Hz), 7.68 (1H, dd, J=8.55, 6.10 Hz), 7.21 (1H, td, J=8.24, 2.44 Hz), 7.00 (1H, dd, J=8.24, 2.44 Hz), 4.35 (2H, d, J=6.71 Hz), 3.96 (4H, br), 2.65-2.72 (2H, m), 2.43 (3H, s), 2.42 (3H, s), 2.29-2.38 (2H, m), 2.03-2.13 (2H, m); LC/MS m/z 455.04 (M+H). HPLC rt=1.87 min. White crystalline solid

EXAMPLE 128

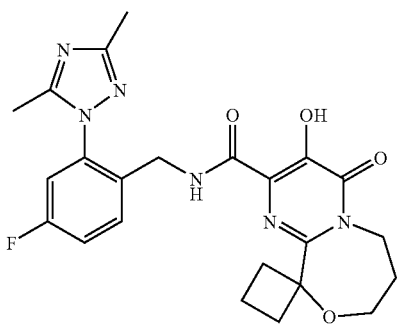

Spiro[cyclobutane-1,10'(4'H)-[6H]pyrimido[2,1-c][1,4]oxazepine]-2'-carboxamide, N-[[2-(3,5-dimethyl-1H-1,2,4-triazol-1-yl)-4-fluorophenyl]methyl]-7',8'-dihydro-3'-hydroxy-4'-oxo-. $^1$H NMR (500 MHz, CDCl$_3$) δ ppm 12.17 (1H, s), 8.44 (1H, t, J=6.26 Hz), 7.67 (1H, dd, J=8.55, 5.80 Hz), 7.21 (1H, td, J=8.24, 2.75 Hz), 6.99 (1H, dd, J=8.55, 2.44 Hz), 4.36-4.43 (2H, m), 4.33 (2H, d, J=6.41 Hz), 3.90 (2H, t, J=5.49 Hz), 2.75-2.84 (2H, m), 2.46-2.40 (2H, m), 2.44 (3H, s), 2.41 (3H, s), 1.85-1.94 (1 H, m), 1.83 (2 H, dt, J=10.76, 5.46 Hz), 1.65-1.74 (1 H, m); $^{13}$C NMR (126 MHz, CDCl$_3$) δ ppm 168.31, 160.95, 160.48, 158.49, 153.70, 150.76, 147.81, 136.90, 133.38, 133.31, 130.81, 124.43, 117.50, 117.33, 114.25, 114.06, 82.13, 64.54, 40.77, 38.62, 31.96, 28.66, 13.77, 12.77, 12.68; HRMS (ESI) calcd for C$_{23}$H$_{26}$N$_6$O$_4$F (M+H) 469.2000, found 469.1999; Elem. Anal. calcd for C$_{23}$H$_{25}$N$_6$O$_4$F: C 58.96, H 5.37, N 17.93, found: C 59.03, H 5.25, N 17.82. HPLC rt=1.91 min. White crystalline solid

EXAMPLE 129

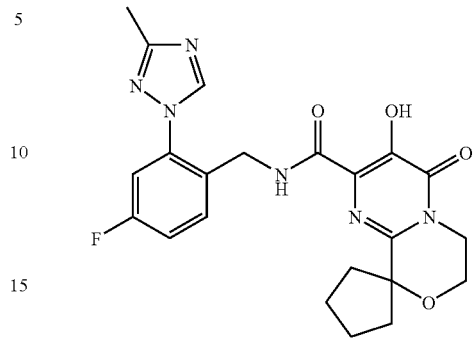

Spiro[cyclopentane-1,9'(4'H)-pyrimido[2,1-c][1,4]oxazine]-2'-carboxamide, N-[[4-fluoro-2-(3-methyl-1H-1,2,4-triazol-1-yl)phenyl]methyl]-6',7'-dihydro-3'-hydroxy-4'-oxo-. $^1$HNMR (500 MHz, CDCl$_3$) δ: 12.10 (1H, s), 8.55 (1H, t, J=6.1 Hz), 8.29 (1H, s), 7.69 (1H, dd, J=8.5, 5.8 Hz), 7.17 (1H, td, J=8.2, 2.5 Hz), 7.08 (1H, dd, J=8.5, 2.5 Hz), 4.47 (2H, d, J=6.7 HzO, 4.02-3.94 (4H, m), 2.52 (3H, s), 2.23-2.16 (2H, m), 2.09-2.04 (2H, m), 1.88-1.83 (4H, m). HRMS (M+H) cald. for C$_{22}$H$_{24}$FN$_6$O$_4$: 455.1843, found: 455.1833. Elem. anal. calcd for C$_{22}$H$_{23}$FN$_6$O$_4$: C, 58.14, H, 5.10; N, 18.49; found: C, 57.98; H, 4.92; 18.40.

EXAMPLE 130

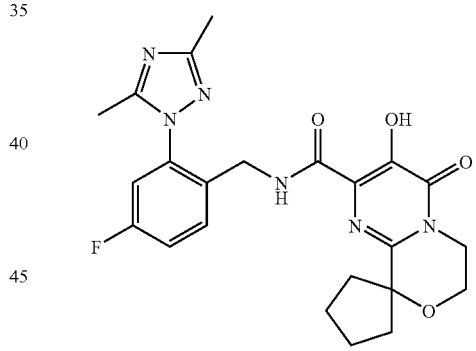

Spiro[cyclopentane-1,9'(4'H)-pyrimido[2,1-c][1,4]oxazine]-2'-carboxamide, N-[[2-(3,5-dimethyl-1H-1,2,4-triazol-1-yl)-4-fluorophenyl]methyl]-6',7'-dihydro-3'-hydroxy-4'-oxo-. LC/MS m/z 469 (M+H). $^1$H NMR (CDCl$_3$, 500 MHz) δ ppm 1.80-1.93 (4H, m, 11, CH$_2$), 2.00-2.13 (2H, m, CH$_2$), 2.14-2.25 (2H, m, CH$_2$), 2.41 (3H, s CH$_3$), 2.42 (3H, s, CH$_3$), 3.93-3.98 (2H, m, OCH$_2$), 4.00 (2H, q, J=5.4 Hz, 7-NCH$_2$), 4.31 (2H, d, J=6.7 Hz, CH$_2$), 6.99 (1H, dd, J=8.4, 2.6 Hz, CH), 7.20 (1H, dt, J=8.5, 2.5 Hz, CH), 7.64 (1H, dd, J=8.5, 5.9 Hz, CH), 8.25 (1H, t, J=6.4 Hz, NH), 12.00 (1H, s, OH). $^{13}$C NMR (CDCl$_3$, 125.8 Hz) δ ppm 12.7 (CH$_3$), 13.8 (CH$_3$), 24.5 (CH$_2$), 38.6 (NCH$_2$), 40.4 (CH$_2$), 42.9 (NCH$_2$), 58.7 (OCH$_2$), 86.2 (C), 114.2 (d, J=24 Hz, CH), 117.3 (d, J=21 Hz, CH), 125.6 (C), 130.8 (d, J=3.8 Hz, C), 133.2 (d, J=8.7 Hz, CH), 137.0 (d, J=9.6 Hz, C), 146.4 (C), 151.5 (C), 153.8 (C), 157.8 (C), 160.5 (C), 161.9 (d, J=250 Hz, CF), 168.2 (C=O). HRMS (ESI) calcd for C$_{23}$H$_{26}$FN$_6$O$_4$ (M+H) 469.2000, found 469.1990. UV (MeOH) λ max 317 nm

EXAMPLE 131

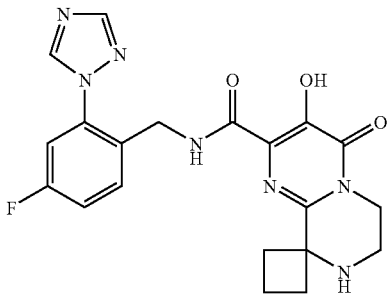

Spiro[cyclobutane-1,9'H)-[4H]pyrazino[1,2-a]pyrimidine]-2'-carboxamide, N-[[4-fluoro-2-(1H-1,2,4-triazol-1-yl)phenyl]methyl]-7',8'-dihydro-3'-hydroxy-4'-oxo-. $^1$H NMR (500 MHz, DMSO-d$_6$) δ ppm 2.08 (m, 1 H) 2.15 (m, 1 H) 2.45-2.52 (m, 2 H) 2.82-2.90 (m, 2 H) 3.53 (t, J=5.95 Hz, 2 H) 4.00 (t, J=5.80 Hz, 2 H) 4.48 (d, J=6.41 Hz, 2 H) 7.43 (td, J=8.39, 2.44 Hz, 1 H) 7.55-7.62 (m, 2 H) 8.31 (s, 1 H) 9.07 (s, 1 H) 9.28 (t, J=6.41 Hz, 1 H), 12.25 (brs, 1 H).

EXAMPLE 132

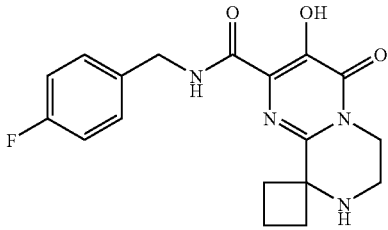

Spiro[cyclobutane-1,9'(6'H)-[4H]pyrazino[1,2-a]pyrimidine]-2'-carboxamide, N-[(4-fluorophenyl)methyl]-7',8'-dihydro-3'-hydroxy-4'-oxo-. $^1$H NMR (500 MHz, DMSO-d$_6$) δ ppm 2.05-2.14 (m, 2 H) 2.42-2.49 (m, 2 H) 2.92 (ddd, J=13.20, 9.23, 6.26 Hz, 2 H) 3.53 (t, J=5.95 Hz, 2 H) 4.02 (t, J=6.10 Hz, 2 H) 4.53 (d, J=6.41 Hz, 2 H) 7.18 (t, J=9.00 Hz, 2 H) 7.39 (dd, J=8.55, 5.49 Hz, 2 H) 9.45 (t, J=6.41 Hz, 1 H), 12.54 (brs, 1 H).

We claim:

1. A compound of Formula I selected from the group consisting of

N-[(4-fluorophenyl)methyl]-7',8'-dihydro-3'-hydroxy-8'-methyl-4'-oxo-spiro[cyclopentane-1,9'(6'H)-[4H]pyrazino[1,2-a]pyrimidine]-2'-carboxamide;

N-[[4-fluoro-2-(1 H-1,2,4-triazol-1-yl)phenyl]methyl]-7',8'-dihydro-3'-hydroxy-8'-methyl-4'-oxo-spiro[cyclopentane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8'-methyl-4'-oxo-spiro[cyclopentane-1,9'(6'H)-[4H]pyrazino [1,2-a]pyrimidine]-2'-carboxamide;

N-[(4-fluorophenyl)methyl]-7',8'-dihydro-3'-hydroxy-8'-methyl-4'-oxo-spiro[cyclohexane-1,9'(6'H)-[4H]pyrazino[1,2-a]pyrimidine]-2'-carboxamide;

N-[[4-fluoro-2-(1H-1,2,4-triazol-1-yl)phenyl]methyl]-7',8'-dihydro-3'-hydroxy-8'-methyl-4-oxo-spiro[cyclohexane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8'-methyl-4'-oxo-spiro[cyclohexane-1,9'(6'H)-[4H]pyrazino[1,2-a]pyrimidine]-2'-carboxamide;

N-[(4-fluorophenyl)methyl]-7',8'-dihydro-3'-hydroxy-8'-methyl-4'-oxo-spiro[cyclobutane-1,9'(6'H)-[4H]pyrazino[1,2-a]pyrimidine]-2'-carboxamide;

N-[[4-fluoro-2-(1H-1,2,4-triazol-1-yl)phenyl]methyl]-7',8'-dihydro-3'-hydroxy-8'-methyl-4-oxo-spiro[cyclobutane-1,9'(6'H)-[4H]pyrazino[1,2-a]pyrimidine]-2'-carboxamide;

N-[[4-fluoro-2-(5-methyl-1H-1,2,4-triazol-1-yl)phenyl]methyl]-7',8'-dihydro-3'-hydroxy-8-methyl-4'-oxo-spiro[cyclobutane-1,9'(6'H)-[4H]pyrazino[1,2-a]pyrimidine]-2'-carboxamide;

N-[[4-fluoro-2-(1H-1,2,3-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(4,5-dimethyl-1H-1,2,3-triazol-1-yl)-4-fluorophenyl]methyl]-6',7'-dihydro-3-hydroxy-4'-oxo-spiro[cyclobutane-1,9'(4'H)-pyrimido[2,1-c][1,4]oxazine]-2'-carboxamide;

N-[[2-[4-(1,1-dimethylethyl)-1H-1,2,3-triazol-1-yl]-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(5-methyl-1H-1,2,3-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(2-oxo-3-oxazolidinyl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[4-fluoro-2-(2-oxo-1-azetidinyl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(4,5-dimethyl-1H-1,2,3-triazol-1-yl)-4-fluorophenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[(4-fluorophenyl)methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(1H-1,2,4-triazol-1-yl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(methylsulfonyl)phenyl]methyl]-6',7'-dihydro-3'-hydroxy-4'-oxo-spiro[oxetane-3,9'(4'H)-pyrimido[2,1-c][1,4]oxazine]-2'-carboxamide;

N-[[4-fluoro-2-(1H-1,2,3-triazol-1-yl)phenyl]methyl]-2,3,5,6,6',7'-hexahydro-3'-hydroxy-4'-oxo-spiro[4H-pyran-4,9'(4'H)-pyrimido[2,1-c][1,4]oxazine]-2'-carboxamide;

N-[[4-fluoro-2-(1H-1,2,3-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[(4-fluorophenyl)methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-[(methylamino)carbonyl]phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(methylsulfonyl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

[5-fluoro-2-[[[(2,3,5,6,7',8'-hexahydro-3'-hydroxy-4'-oxospiro[4H-pyran-4,10'(4'H)-[6H]pyrimido[2,1-c][1,4]oxazepin]-2'-yl)carbonyl]amino]methyl]phenyl]-phosphonic acid, dimethyl ester;

N-[[4-fluoro-2-(1H-1,2,4-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(5-methyl-1H-1,2,4-triazol-1-yl)phenyl]methyl]-2,3,5,6,7',8'-hexahydro-3-hydroxy-4'-oxo-spiro[4H-pyran-4,10'(4'H)-[6H]pyrimido[2,1-c][1,4]oxazepine]-2'-carboxamide;

2,3,5,6,7',8'-hexahydro-3'-hydroxy-N-[[2-(3-methyl-1H-1,2,4-triazol-1-yl)phenyl]methyl]-4'-oxo-spiro[4H-pyran-4,10'(4'H)-[6H]pyrimido[2,1-c][1,4]oxazepine]-2'-carboxamide;

N-[[4-fluoro-2-(1H-1,2,3-triazol-1-yl)phenyl]methyl]-2,3,5,6,7',8'-hexahydro-3'-hydroxy-4'-oxo-spiro[4H-pyran-4,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[cyclobutane-1,9'(4'H)-pyrimido[2,1-c][1,4]oxazine]-2'-carboxamide;

6',7'-dihydro-3'-hydroxy-4'-oxo-N-[[2-(2-oxo-1-azetidinyl)phenyl]methyl]-spiro[cyclobutane-1,9'(4'H)-pyrimido[2,1-c][1,4]oxazine]-2'-carboxamide;

6',7'-dihydro-3'-hydroxy-4'-oxo-N-[[2-(2-oxo-3-oxazolidinyl)phenyl]methyl]-spiro[cyclobutane-1,9'(4'H)-pyrimido[2,1-c][1,4]oxazine]-2'-carboxamide;

N-[[2-(3,5-dimethyl-1H-1,2,4-triazol-1-yl)-4-fluorophenyl]methyl]-6',7'-dihydro-3'-hydroxy-4'-oxo-spiro[cyclobutane-1,9'(4'H)-pyrimido[2,1-c][1,4]oxazine]-2'-carboxamide;

N-[[2-(3,5-dimethyl-1H-1,2,4-triazol-1-yl)-4-fluorophenyl]methyl]-7',8'-dihydro-3'-hydroxy-4'-oxo-spiro[cyclobutane-1,10'(4'H)-[6H]pyrimido[2,1-c][1,4]oxazepine]-2'-carboxamide;

N-[[4-fluoro-2-(3-methyl-1H-1,2,4-triazol-1-yl)phenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[[2-(3,5-dimethyl-1H-1,2,4-triazol-1-yl)-4-fluorophenyl]methyl]-6',7'-dihydro-3'-hydroxy-4'-oxo-spiro[cyclopentane-1,9'(4'H)-pyrimido[2,1-c][1,4]oxazine]-2'-carboxamide;

N-[[4-fluoro-2-(1H-1,2,4-triazol-1-yl)phenyl]methyl]-7',8'-dihydro-3'-hydroxy-4'-oxo-spiro[cyclobutane-1,9'(6'H)-[4H]pyrazino[1,2-a]pyrimidine]-2'-carboxamide; and N-[(4-fluorophenyl)methyl]-7',8'-dihydro-3'-hydroxy-4'-oxo-spiro[cyclobutane-1,9'(6'H)-[4H]pyrazino[1,2-a]pyrimidine]-2'-carboxamide;

or a pharmaceutically acceptable salt or solvate thereof.

2. A composition comprising a therapeutic amount of a compound of claim 1 and a pharmaceutically acceptable carrier.

3. A method of inhibiting HIV integrase comprising contacting a compound of claim 1 with HIV integrase.

4. A method of inhibiting HIV viral DNA integration into human DNA comprising administering an effective amount of a compound of claim 1 to a patient infected with HIV.

5. A method for treating HIV infection comprising administering a therapeutically effective amount of a compound of claim 1, or a pharmaceutically acceptable salt or solvate thereof, to a patient infected with HIV.

6. The method of claim 5, further comprising a therapeutically effective amount of one or more other HIV treatment agents selected from the group consisting of HIV protease inhibitors, HIV nucleoside reverse transcriptase inhibitors, HIV non-nucleoside reverse transcriptase inhibitors, HIV-entry inhibitors, HIV integrase inhibitors, immunomodulators, or a combination thereof.

* * * * *